(12) United States Patent
Ueno et al.

(10) Patent No.: US 7,005,430 B2
(45) Date of Patent: Feb. 28, 2006

(54) FUSED PURINE DERIVATIVES

(75) Inventors: Kimihisa Ueno, Shizuoka (JP); Akira Ogawa, Shizuoka (JP); Yoshihisa Ohta, Yokohama (JP); Yuji Nomoto, Shizuoka (JP); Kotaro Takasaki, Shizuoka (JP); Hideaki Kusaka, Shizuoka (JP); Hiroshi Yano, Shizuoka (JP); Chiharu Nakagawa, Gifu (JP); Satoshi Nakanishi, Yokohama (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/149,423

(22) PCT Filed: Dec. 22, 2000

(86) PCT No.: PCT/JP00/09160

§ 371 (c)(1),
(2), (4) Date: Oct. 22, 2002

(87) PCT Pub. No.: WO01/47931

PCT Pub. Date: Jul. 5, 2001

(65) Prior Publication Data

US 2003/0176698 A1  Sep. 18, 2003

(30) Foreign Application Priority Data

Dec. 24, 1999 (JP) .................. 11-366313

(51) Int. Cl.
C07D 487/14  (2006.01)
C07D 473/24  (2006.01)
C07D 473/22  (2006.01)
A61K 31/519  (2006.01)
A61P 3/10    (2006.01)

(52) U.S. Cl. ............. 514/183; 514/220; 514/267; 514/233.3; 540/471; 540/559; 544/251; 544/115; 544/118; 544/271; 544/272; 544/276

(58) Field of Classification Search ............. None
See application file for complete search history.

(56) References Cited

U.S. PATENT DOCUMENTS

| 4,338,319 | A  |    | 7/1982  | Kjellin et al. |
| 5,064,947 | A  |    | 11/1991 | Peet et al. |
| 5,086,176 | A  |    | 2/1992  | Peet et al. |
| 5,270,316 | A  |    | 12/1993 | Suzuki et al. |
| 5,719,279 | A  |    | 2/1998  | Küfner-Mühl et al. |
| 6,306,847 | B1 | *  | 10/2001 | Tsumuki et al. ............ 514/183 |
| 6,339,072 | B1 | *  | 1/2002  | Martin et al. ............. 514/46 |
| 6,489,331 | B1 | *  | 12/2002 | Shimada et al. ........... 514/220 |
| 6,605,601 | B1 | *  | 8/2003  | Lin et al. ............... 544/251 |

FOREIGN PATENT DOCUMENTS

| EP | 256692   | 2/1988  |
| EP | 386683   | 9/1990  |
| EP | 380111   | 10/1990 |
| EP | 0390111  | 10/1990 |
| EP | 747356   | 12/1996 |
| EP | 884318   | 12/1998 |
| EP | 1092435  | 4/2001  |
| JP | 10158267 | 6/1998  |
| WO | 9815555  | 4/1998  |
| WO | 0001388  | 1/2000  |

OTHER PUBLICATIONS

35 J. Med. Chem. 3578-3581 (1992).
36 J. Med. Chem. 2508-2518 (1993).
23 J. Med. Chem. 1188-1198 (1980).
40 J. Med. Chem. 3248-3253 (1997).
30 J. Heterocycl. Chem. 241-246 (1993).
J. Chem. Soc. Perkin I 739-743 (1973).
41 Bull. Chem. Soc. Japan 1634-1638 (1968).
29 J. Org. Chem. 2658-2663 (1964).

(Continued)

Primary Examiner—Mark L. Berch
(74) Attorney, Agent, or Firm—Greenblum & Bernstein, P.L.C.

(57) ABSTRACT

A condensed purine derivative represented by Formula (I):

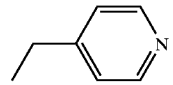

wherein X—Y-Z represents $R^1N$—C=O or N=C—W, $R^2$ represents a hydrogen atom, a substituted or unsubstituted lower alkyl group, a substituted or unsubstituted aralkyl group, a substituted or unsubstituted aryl group, a substituted or unsubstituted aromatic heterocyclic group, a substituted or unsubstituted alicyclic heterocyclic group or the like, n represents an integer of from 0 to 3, $V^1$ represents a hydrogen atom, a substituted or unsubstituted lower alkyl group, a substituted or unsubstituted aralkyl group, a substituted or unsubstituted aryl group, or a substituted or unsubstituted aromatic heterocyclic group, $V^2$ represents a substituted lower alkyl group or a substituted or unsubstituted aromatic heterocyclic group, and when $V^1$ represents a hydrogen atom, a lower alkyl group, a substituted or unsubstituted aralkyl group, or a substituted or unsubstituted aryl group, and for example, X—Y-Z represents $R^{1a}N$—C=O and $R^2$ represents a substituted lower alkyl group, a substituted or unsubstituted aralkyl group, a substituted or unsubstituted alicyclic heterocyclic group, a halogen atom, a lower alkylthio group, —$NR^7R^8$, —$CO_2H$, a lower alkoxycarbonyl group, —COHal, —$CONR^9R^{10}$ or —CHO, $V^2$ may represent a lower alkyl group, a substituted or unsubstituted aralkyl group, or a substituted or unsubstituted aryl group; or a pharmacologically acceptable salt thereof.

14 Claims, No Drawings

OTHER PUBLICATIONS

Synthesis 1144-1151 (1992).
2 J. Heterocycl. Chem. 1 (1965).
23 J. Org. Chem. 575-581 (1958).
44 Tetrahedron 5525-5540 (1988).
64 J. Org. Chem. 6411-6417 (1999).
43 J. Org. Chem. 2539-2541 (1978).
38 Tetrahedron 3597-3604 (1982).
16 (35) J. Med. Chem. 3066-3075 (1992).
32 (6) J. Med Chem. 1231-1237 (1989).
127 Endocrinology 126-31 (1990).
5 Pharmacotherapy 43-62 (1985).
7 Pharmacology and Clinic 121-129 (1997).
English Language Abstract for JP Appln. No. 10-158267.

* cited by examiner

FUSED PURINE DERIVATIVES

TECHNICAL FIELD

The present invention relates to condensed purine derivatives which have glucose concentration-dependent insulin secretion promoting action and suitable hypoglycemic action and is useful as an antidiabetic agent.

BACKGROUND ART

Diabetes is caused by metabolic abnormality mainly of glycometabolism, resulting from insufficient insulin secretion, decreased sensitivity of target cells of insulin and so forth, and principally characterized by noticeable hyperglycemia. If the hyperglycemia continues for a long period of time, serious complications arise in various organs and nerves such as retinopathy, nephropathy and neuropathy, which are caused mainly by vascular lesion. Therefore, for the treatment of diabetes, it is extremely important to control and maintain blood glucose level at a normal level, and methods for that purpose have been studied since old days.

For a type of diabetes where onset is gradual and insulin therapy is not necessarily required for life support (non-insulin dependent diabetes: NIDDM), blood glucose level can be controlled by combination of exercise therapy and drug therapy. As the drugs, insulin secretion promoters, one of orally available hypoglycemic agents, have widely been used clinically. However, since currently available insulin secretion promoters all promote insulin secretion non-dependently on glucose level, they cause problems of severe hypoglycemia or insufficient control of blood glucose if doses are not appropriate, and are not fully satisfactory drugs. If a hypoglycemic agent can be provided that is capable of promoting insulin secretion dependently on a blood glucose level, the agent is expected to be extremely useful for blood glucose control of patients suffering from diabetes because the risk of hypoglycemia due to an excess dosage can be avoided.

As condensed purine derivatives, Japanese Patent Unexamined Publication (Kokai) No. 3-204880, Journal of Medicinal Chemistry (J. Med. Chem.), 35, p. 3578, 1992, Journal of Medicinal Chemistry (J. Med. Chem.), 36, 2508, 1993, International Patent Publications WO98/15555 and WO 00/01388 disclose that the compounds represented by the following formula (A) have diuretic action, mild antiasthmatic action, antidemential action, bronchodilatation action, antiallergic action, antiulcer action, or hypoglycemic action.

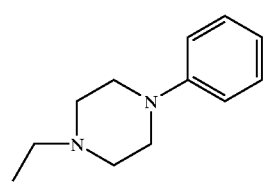

wherein $R^{1A}$ represents a hydrogen atom, a lower alkyl group, a substituted or unsubstituted aralkyl group, a substituted or unsubstituted aryl group, or a substituted or unsubstituted aromatic heterocyclic group, $R^{2A}$ represents a hydrogen atom, a lower alkyl group, a substituted or unsubstituted aryl group, or a substituted or unsubstituted aromatic heterocyclic group, $R^{3A}$ represents a hydrogen atom, a lower alkyl group, or a substituted or unsubstituted aralkyl group, $V^{1A}$ and $V^{2A}$ may be the same or different and each represents a hydrogen atom, a lower alkyl group, a substituted or unsubstituted aralkyl group, or a substituted or unsubstituted aryl group, and m represents an integer of from 0 to 3.

Journal of Medicinal Chemistry (J. Med. Chem.), 23, 1188, 1980 discloses that the compound represented by the following formula (B) has mild bronchodilatation action.

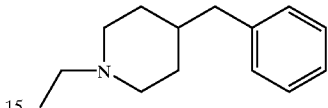

Journal of Medicinal Chemistry (J. Med. Chem.), 40, 3248, 1997 and Japanese Patent Unexamined Publication No. 10-158267 disclose that the compounds represented by the following formula (C) have type IV phosphodiesterase inhibitory action (bronchodilatation action).

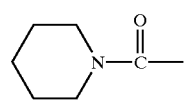

wherein $R^{1C}$, $R^{3C}$ and $R^{4C}$ may be the same or different and each represents a hydrogen atom or a $C_1$–$C_6$ alkyl group which may be substituted with a lower alkyloxy group or an acyl group, and p represents an integer of from 1 to 4.

Furthermore, EP390111A discloses that the compounds represented by the following formula (D) have adenosine antagonizing action.

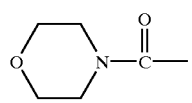

wherein $R^{4D}$ represents a hydrogen atom, a phenyl group, or β-D-ribofuranosyl group, $W^D$ represents a hydrogen atom, an alkyl group having 1 to 4 carbon atoms or an alkoxy group having 1 to 4 carbon atoms, $V^{1D}$ represents an aralkyl group, $V^{2D}$ represents a hydrogen atom or a phenyl group, and when $V^{2D}$ is a phenyl group, $V^{1D}$ may represent an alkyl group having 1 to 6 carbon atoms.

DISCLOSURE OF THE INVENTION

An object of the present invention is to provide a medicament useful for prophylactic and/or therapeutic treatment of diabetes or complications of diabetes. More specifically, the object is to provide a medicament that has a blood sugar level-dependent insulin secretion promoting action.

The inventors of the present invention conducted various researches to achieve the aforementioned object. As a result, they found that the compounds represented by the following formula (I) had an insulin secretion promoting action and were useful as an active ingredient of antidiabetic agents. The present invention was achieved on the basis of the aforementioned finding.

The present invention thus relates to the following subject matters (1) to (23).

(1) A condensed purine derivative represented by Formula (I):

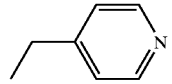

wherein X—Y-Z represents $R^1N$—C=O (in the formula, $R^1$ represents a hydrogen atom, a substituted or unsubstituted lower alkyl group, a substituted or unsubstituted aralkyl group, a substituted or unsubstituted aryl group, or a substituted or unsubstituted aromatic heterocyclic group) or N=C—W [in the formula, W represents a halogen atom, a substituted or unsubstituted aromatic heterocyclic group, a substituted or unsubstituted alicyclic heterocyclic group, —$NR^4R^5$ (in the formula, $R^4$ and $R^5$ may be the same or different and each represents a hydrogen atom, a substituted or unsubstituted lower alkyl group, a substituted or unsubstituted aryl group, or a substituted or unsubstituted aralkyl group, or $R^4$ and $R^5$ may bind to each other to form a heterocyclic group together with the adjacent nitrogen atom), —$OR^6$ (in the formula, $R^6$ represents a substituted or unsubstituted lower alkyl group, a substituted or unsubstituted aryl group, or a substituted or unsubstituted aralkyl group), —$SR^{6a}$ (in the formula, $R^{6a}$ has the same meaning as $R^6$ mentioned above), a substituted or unsubstituted lower alkyl group or a cyano group], $R^2$ represents a hydrogen atom, a substituted or unsubstituted lower alkyl group, a substituted or unsubstituted aralkyl group, a substituted or unsubstituted aryl group, a substituted or unsubstituted aromatic heterocyclic group, a substituted or unsubstituted alicyclic heterocyclic group, a halogen atom, a lower alkylthio group, —$NR^7R^8$ (in the formula, $R^7$ and $R^8$ have the same meanings as $R^4$ and $R^5$ mentioned above, respectively), —$CO_2H$, a lower alkoxycarbonyl group, —COHal (in the formula, Hal represents a halogen atom), —$CONR^9R^{10}$ (in the formula, $R^9$ and $R^{10}$ have the same meanings as $R^4$ and $R^5$ mentioned above, respectively) or —CHO, $R^3$ represents a hydrogen atom, a lower alkyl group, a substituted or unsubstituted aralkyl group, or a lower alkoxyalkyl group, n represents an integer of from 0 to 3, $V^1$ represents a hydrogen atom, a substituted or unsubstituted lower alkyl group, a substituted or unsubstituted aralkyl group, a substituted or unsubstituted aryl group, or a substituted or unsubstituted aromatic heterocyclic group, $V^2$ represents a substituted lower alkyl group, or a substituted or unsubstituted aromatic heterocyclic group, and when $V^1$ represents a hydrogen atom, a lower alkyl group, a substituted or unsubstituted aralkyl group, or a substituted or unsubstituted aryl group, and (a) X—Y-Z represents $R^{1a}N$—C=O (in the formula, $R^{1a}$ represents any of the groups in the definition of the aforementioned $R^1$ excluding a substituted lower alkyl group), and $R^2$ represents a substituted lower alkyl group, a substituted or unsubstituted aralkyl group, a substituted or unsubstituted alicyclic heterocyclic group, a halogen atom, a lower alkylthio group, —$NR^7R^8$ (in the formula, $R^7$ and $R^8$ have the same meanings as defined above, respectively), —$CO_2H$, a lower alkoxycarbonyl group, —COHal (in the formula, Hal has the same meaning as defined above), —$CONR^9R^{10}$ (in the formula, $R^9$ and $R^{10}$ have the same meanings as those defined above, respectively) or —CHO, (b) X—Y-Z represents $R^1N$—C=O (in the formula, $R^1$ has the same meaning as defined above), and $R^3$ represents a lower alkoxyalkyl group, (c) X—Y-Z represents $R^{1b}N$—C=O (in the formula, $R^{1b}$ represents a substituted lower alkyl group), (d) X—Y-Z represents N=C—W (in the formula, W has the same meaning as defined above), and $R^2$ represents a substituted or unsubstituted lower alkyl group, a substituted or unsubstituted aralkyl group, a substituted or unsubstituted aryl group, a substituted or unsubstituted aromatic heterocyclic group, a substituted or unsubstituted alicyclic heterocyclic group, a halogen atom, a lower alkylthio group, —$NR^7R^8$ (in the formula, $R^7$ and $R^8$ have the same meanings as defined above, respectively), —$CO_2H$, a lower alkoxycarbonyl group, —COHal (in the formula, Hal has the same meaning as defined above), —$CONR^9R^{10}$ (in the formula, $R^9$ and $R^{10}$ have the same meanings as defined above, respectively) or —CHO, or (e) X—Y-Z represents N=C—W (in the formula, W has the same meaning as defined above), and $R^3$ represents a lower alkyl group, a substituted or unsubstituted aralkyl group, or a lower alkoxyalkyl group, $V^2$ may represent a lower alkyl group, a substituted or unsubstituted aralkyl group, or a substituted or unsubstituted aryl group; or a pharmacologically acceptable salt thereof.

(2) The condensed purine derivative or a pharmacologically acceptable salt thereof according to the aforementioned (1), wherein X—Y-Z represents $R^1N$—C=O (in the formula, $R^1$ has the same meaning as defined above).

(3) The condensed purine derivative or a pharmacologically acceptable salt thereof according to the aforementioned (2), wherein $R^1$ and $R^2$ represent a substituted or unsubstituted lower alkyl group and $R^3$ represents a hydrogen atom.

(4) The condensed purine derivative or a pharmacologically acceptable salt thereof according to the aforementioned (2) or (3), wherein at least one of $V^1$ and $V^2$ represents a substituted lower alkyl group.

(5) The condensed purine derivative or a pharmacologically acceptable salt thereof according to the aforementioned (2) or (3), wherein at least one of $V^1$ and $V^2$ represents a substituted or unsubstituted aralkyl group.

(6) The condensed purine derivative or a pharmacologically acceptable salt thereof according to the aforementioned (1), wherein X—Y-Z represents N=C—W (in the formula, W has the same meaning as defined above).

(7) The condensed purine derivative or a pharmacologically acceptable salt thereof according to the aforementioned (6), wherein $R^2$ represents a substituted or unsubstituted lower alkyl group.

(8) The condensed purine derivative or a pharmacologically acceptable salt thereof according to the aforementioned (6) or (7), wherein at least one of $V^1$ and $V^2$ represents a substituted or unsubstituted aralkyl.

(9) The condensed purine derivative or a pharmacologically acceptable salt thereof according to any one of the aforementioned (1) to (8), wherein n is 0.

(10) A pharmaceutical composition which comprises the condensed purine derivative or a pharmacologically acceptable salt thereof according to any one of the aforementioned (1) to (9) as an active ingredient.

(11) An agent for prophylactic and/or therapeutic treatment of diabetes, which comprises the condensed purine derivative or a pharmacologically acceptable salt thereof according to any one of the aforementioned (1) to (9) as an active ingredient.

(12) An agent for prophylactic and/or therapeutic treatment of a complication of diabetes, which comprises the condensed purine derivative or a pharmacologically acceptable salt thereof according to any one of the aforementioned (1) to (9) as an active ingredient.

(13) A hypoglycemic agent which comprises the condensed purine derivative or a pharmacologically acceptable salt thereof according to any one of the aforementioned (1) to (9) as an active ingredient.

(14) An insulin secretion promoter which comprises the condensed purine derivative or a pharmacologically acceptable salt thereof according to any one of the aforementioned (1) to (9) as an active ingredient.

(15) Use of the condensed purine derivative or a pharmacologically acceptable salt thereof according to any one of the aforementioned (1) to (9) for the manufacture of a pharmaceutical composition.

(16) Use of the condensed purine derivative or a pharmacologically acceptable salt thereof according to any one of the aforementioned (1) to (9) for the manufacture of an agent for prophylactic and/or therapeutic treatment of diabetes.

(17) Use of the condensed purine derivative or a pharmacologically acceptable salt thereof according to any one of the aforementioned (1) to (9) for the manufacture of an agent for prophylactic and/or therapeutic treatment of a complication of diabetes.

(18) Use of the condensed purine derivative or a pharmacologically acceptable salt thereof according to any one of the aforementioned (1) to (9) for the manufacture of a hypoglycemic agent.

(19) Use of the condensed purine derivative or a pharmacologically acceptable salt thereof according to any one of the aforementioned (1) to (9) for the manufacture of an insulin secretion promoter.

(20) A method for prophylactic and/or therapeutic treatment of diabetes, which comprises a step of administering an effective amount of the condensed purine derivative or a pharmacologically acceptable salt thereof according to any one of the aforementioned (1) to (9).

(21) A method for prophylactic and/or therapeutic treatment of a complication of diabetes, which comprises a step of administering an effective amount of the condensed purine derivative or a pharmacologically acceptable salt thereof according to any one of the aforementioned (1) to (9).

(22) A method for decreasing blood sugar level, which comprises a step of administering an effective amount of the condensed purine derivative or a pharmacologically acceptable salt thereof according to any one of the aforementioned (1) to (9).

(23) A method for promoting insulin secretion, which comprises a step of administering an effective amount of the condensed purine derivative or a pharmacologically acceptable salt thereof according to any one of the aforementioned (1) to (9).

The aforementioned medicaments are preferably provided in the form of a pharmaceutical composition comprising a condensed purine derivative represented by Formula (I) or a pharmacologically acceptable salt thereof and one or more additives for pharmaceutical preparations.

Hereinafter, the compounds represented by Formula (I) are referred to as Compound (I). The same shall apply to the compounds of the other formula numbers.

In the definition of each group in Formula (I), a lower alkyl moiety of a lower alkyl group, a lower alkylthio group, a lower alkoxycarbonyl group, and a lower alkoxyalkyl group includes a straight, branched, and cyclic alkyl groups as well as a combination thereof, which have about 1 to 10 carbon atoms. The cyclic lower alkyl may have one or more rings. Examples of the straight or branched lower alkyl group include, for example, a methyl group, an ethyl group, a n-propyl group, an isopropyl group, a n-butyl group, an isobutyl group, a sec-butyl group, a tert-butyl group, a n-pentyl group, a neopentyl group, a n-hexyl group, a n-heptyl group, a n-octyl group, a n-nonyl group, a n-decyl group and the like. Examples of the cyclic lower alkyl include, for example, a cyclopropyl group, a cyclopropylmethyl group, a cyclobutyl group, a cyclopentyl group, a cyclohexyl group, a cycloheptyl group, a cyclooctyl group, a 1-methylcyclohexyl group, a 4-methylcyclohexyl group, a noradamantyl group, an adamantyl group, a bicyclo[2.2.1]heptyl group, a bicyclo[2.2.2]octyl group, a bicyclo[3.3.0]octyl group, a bicyclo[3.3.1]nonyl group and the like.

An alkylene moiety of the lower alkoxyalkyl group and the aralkyl group corresponds to that obtained by eliminating one hydrogen atom from the straight or branched lower alkyl mentioned above.

An aryl moiety of the aryl group and the aralkyl group consists of a monocyclic ring or two or more condensed rings. Examples thereof include those having about 6 to 14 ring-constituting carbon atoms, for example, a phenyl group, a naphthyl group, an indenyl group, an anthranyl group and the like.

Examples of the aromatic heterocyclic group include, for example, 5- or 6-membered monocyclic aromatic heterocyclic groups containing at least one atom selected from a nitrogen atom, an oxygen atom, and a sulfur atom, bicyclic or a tricyclic condensed aromatic heterocyclic groups comprising 3- to 8-membered rings and containing at least one atom selected from a nitrogen atom, an oxygen atom, and a sulfur atom and the like. More specific examples include those having 5 to 14 ring-constituting atoms such as a furyl group, a thienyl group, a pyrrolyl group, an imidazolyl group, a pyrazolyl group, a triazolyl group, a tetrazolyl group, an oxazolyl group, a thiazolyl group, a pyridyl group, a pyrazinyl group, a pyrimidinyl group, a pyridazinyl group, a triazinyl group, an indolyl group, an indazolyl group, a benzimidazolyl group, a benzoxazolyl group, a benzothiazolyl group, a quinolyl group, an isoquinolyl group, a phthalazinyl group, a naphthylidinyl group, a quinoxalinyl group, a quinazolinyl group, a cinnolinyl group, a purinyl group and the like.

Examples of the alicyclic heterocyclic group include, for example, 5- or 6-membered monocyclic alicyclic heterocyclic groups containing at least one atom selected from a nitrogen atom, an oxygen atom, and a sulfur atom, bicyclic or tricyclic condensed alicyclic heterocyclic groups comprising 3- to 8-membered rings and containing at least one atom selected from a nitrogen atom, an oxygen atom, and a sulfur atom. More specific examples include a pyrrolidinyl group, a 2,5-dioxopyrrolidinyl group, a thiazolidinyl group, an oxazolidinyl group, a 2-oxooxazolidinyl group, a piperidinyl group, a piperazinyl group, a homopiperazinyl group, a morpholinyl group, a thiomorpholinyl group, a tetrahydropyranyl group, a tetrahydrothiopyranyl group, a tetrahydrofuryl group, a tetrahydroquinolyl group, a tetrahydroisoquinolyl group, a tetrahydroquinoxalinyl group, an octahydroquinolyl group, a dihydroindolyl group, a 1,3-dioxoisoindolinyl group, a 1,3-dioxolanyl group, a 1,3-dioxolane-2-spirocyclopentyl group and the like.

Examples of the heterocyclic group formed together with the adjacent nitrogen atom include, for example, 5- or 6-membered monocyclic heterocyclic groups containing at least one nitrogen atom (said monocyclic heterocyclic group may contain a nitrogen atom other than the above, an oxygen atom, or a sulfur atom), bicyclic or tricyclic condensed heterocyclic groups comprising 3- to 8-membered rings and containing at least one nitrogen atom (said condensed heterocyclic group may contain a nitrogen atom other than the above, an oxygen atom, or a sulfur atom). More specific examples include a pyrrolidinyl group, a thiazolidinyl group, an oxazolidinyl group, a piperidino group, a homopiperidino group, a piperazinyl group, a homopiperazinyl group, a morpholino group, a thiomorpholino group, a tetrahydroquinolyl group, a tetrahydroisoquinolyl group, an octahydroquinolyl group, a benzimidazolyl group, an indazolyl group, an indolyl group, an isoindolyl group, a purinyl group, a dihydroindolyl group, a pyrrolyl group, a pyrazolyl group, a triazolyl group, a tetrazolyl group, an imidazolyl group and the like.

Examples of the halogen atom include a fluorine atom, a chlorine atom, a bromine atom and an iodine atom.

Examples of substituents of the substituted aryl group, the substituted aralkyl group, the substituted aromatic heterocyclic group, and the substituted alicyclic heterocyclic group, which may be the same or different and in number of 1 to 3, include a substituted or unsubstituted lower alkyl group, a substituted or unsubstituted aryl group, a substituted or unsubstituted aryloxy group, a substituted or unsubstituted aroyl group, a substituted or unsubstituted aralkyl group, a substituted or unsubstituted aralkyloxy group, a substituted or unsubstituted lower alkenyl group, a substituted or unsubstituted lower alkynyl group, a substituted or unsubstituted lower alkoxy group, a substituted or unsubstituted lower alkoxycarbonyl group, a substituted or unsubstituted lower alkylthio group, a substituted or unsubstituted lower alkylsulfonyl group, a substituted or unsubstituted lower alkanoyl group, a mono- or di-lower alkyl-substituted carbamoyl group, a mono- or di-lower alkyl-substituted amino group, a halogen atom, a carboxyl group, a hydroxyl group, a nitro group, an amino group, a cyano group and the like. Examples of the lower alkenyl group used herein include a straight and branched alkenyl groups having 2 to 6 carbon atoms such as a vinyl group, an allyl group, a 1-propenyl group, a methacryl group, a butenyl group, a crotyl group, a pentenyl group, and a hexenyl group, and examples of the lower alkynyl group used herein include a straight and branched alkynyl groups having 2 to 6 carbon atoms such as an ethynyl group, a propynyl group, a butynyl group, a pentynyl group, and a hexynyl group. Numbers of unsaturated bond in the lower alkenyl group and the lower alkynyl group are not particularly limited, and they preferably contain one unsaturated bond. Each lower alkyl moiety of the lower alkyl group, the lower alkoxy group, the lower alkoxycarbonyl group, the lower alkylthio group, the lower alkylsulfonyl group, the lower alkanoyl group, the mono- or di-lower alkyl-substituted carbamoyl group, and the mono- or di-lower alkyl-substituted amino group has the same meaning as the aforementioned lower alkyl group. Each alkylene moiety of the aralkyl group and the aralkyloxy group has the same meaning as the aforementioned alkylene moiety. Each aryl moiety of the aryl group, the aryloxy group, and the aroyl group has the same meaning as the aforementioned aryl group. The halogen atom has the same meaning as the aforementioned halogen atom. Examples of substituents of the substituted lower alkyl group, the substituted aryl group, the substituted aryloxy group, the substituted aroyl group, the substituted aralkyl group, the substituted aralkyloxy group, the substituted lower alkenyl group, the substituted lower alkynyl group, the substituted lower alkoxy group, the substituted lower alkoxycarbonyl group, the substituted lower alkylthio group, the substituted lower alkylsulfonyl group, and the substituted lower alkanoyl group, which may be the same or different and in number of 1 to 3, include a hydroxyl group, a halogen atom having the same meaning as defined above, a carboxyl group, a sulfo group, a phosphono group, an ester derived from any of these acidic groups (e.g., a lower alkyl ester, an aralkyl ester, an aryl ester and the like: the lower alkyl moiety, the aralkyl moiety, and the aryl moiety of these esters have the same meanings as those defined above, respectively). In the di-lower alkyl-substituted carbamoyl group and the di-lower alkyl-substituted amino group, two of the lower alkyl groups which bind to a carbamoyl group or an amino group may be the same or different.

Examples of substituents of the substituted lower alkyl, which may be the same or different and in number of 1 to 3, include a lower alkoxy group, a hydroxyl group, a cyano group, an azido group, a carboxyl group, a phosphono group, an ester group derived from any of these acidic groups (e.g., a lower alkyl ester, an aralkyl ester, an aryl ester and the like: the lower alkyl moiety, the aralkyl moiety, and the aryl moiety of these esters have the same meanings as those defined above, respectively), a lower alkylthio group, a lower alkylaminocarbonyl group, a lower alkoxycarbonyl group, a substituted or unsubstituted aromatic heterocyclic group, a substituted or unsubstituted alicyclic heterocyclic group, —$NR^{11}R^{12}$ (in the formula, $R^{11}$ and $R^{12}$ may be the same or different and each represents a hydrogen atom, a lower alkyl group, a lower alkanoyl group, an aryl group, an aralkyl group, or an aralkyloxy group, or $R^{11}$ and $R^{12}$ may bind to each other to form a heterocyclic group together with the adjacent nitrogen atom), a halogen atom, an arylsulfonyloxy group which may be substituted with a lower alkyl group, a lower alkylsulfonyl group, a lower alkylsulfonyloxy group, a trifluoromethanesulfonyloxy group and the like. Each lower alkyl moiety of the lower alkyl group, the lower alkoxy group, the lower alkylthio group, the lower alkylaminocarbonyl group, the lower alkoxycarbonyl group, the lower alkanoyl group, the arylsulfonyloxy group which may be substituted with a lower alkyl group, the lower alkylsulfonyl group, and the lower alkylsulfonyloxy group has the same meaning as the aforementioned lower alkyl group. Each aryl moiety of the aryl group, the aralkyl group, the aralkyloxy group, and the arylsulfonyloxy group has the same meaning as the aforementioned aryl group. An alkylene moiety of the aralkyl has the same meaning as the aforementioned alkylene moiety. The halogen atom, the aromatic heterocyclic group, the alicyclic heterocyclic group, and the heterocyclic group formed together with the adjacent nitrogen atom have the same meanings as defined above, respectively. Substituents of the substituted aromatic heterocyclic group and the substituted alicyclic heterocyclic group have the same meanings as those mentioned above.

Further, in Formula (I), the substituting position of $V^1$ or $V^2$ is not particularly limited, and each of them may substitute at any position on the ring. When $V^1$ or $V^2$ is a substituent other than a hydrogen atom, the stereochemistry of the carbon atom to which it binds may be either in S- or R-configuration. Symbol "n" is preferably 0.

Examples of pharmacologically acceptable salts of Compound (I) include acid addition salts such as inorganic acid salts and organic acid salts, base addition salts such as metal salts, ammonium salts, and organic ammonium salts, amino acid addition salts and the like. Examples of the pharmacologically acceptable acid addition salts include, for example, inorganic acid salts such as hydrochlorides, sulfates, and phosphates, organic acid salts such as acetates, maleates, fumarates, tartrates, and citrates. Examples of the pharmacologically acceptable metal salts include, for example, alkali metal salts such as sodium salts and potassium salts, alkaline earth metal salts such as magnesium salts and calcium salts, as well as aluminum salts, zinc salts and the like. Examples of the pharmacologically acceptable organic ammonium salts include, for example, addition salts of an organic amine such as morpholine or piperidine. Examples of the pharmacologically acceptable amino acid addition salts include, for example, addition salts of lysine, glycine, phenylalanine or the like.

The present invention also provides a condensed purine derivative represented by Formula (I):

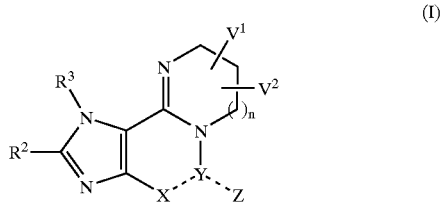

(I)

wherein X—Y-Z represents $R^1N$—C=O (in the formula, $R^1$ represents a hydrogen atom, a substituted or unsubstituted lower alkyl group, a substituted or unsubstituted cyclic lower alkyl group, a substituted or unsubstituted cyclic lower alkyl-substituted lower alkyl group, a substituted or unsubstituted aralkyl group, a substituted or unsubstituted aryl group, or a substituted or unsubstituted aromatic heterocyclic group) or N=C—W [in the formula, W represents a halogen atom, a substituted or unsubstituted aromatic heterocyclic group, a substituted or unsubstituted alicyclic heterocyclic group, —$NR^4R^5$ (in the formula, $R^4$ and $R^5$ may be the same or different and each represents a hydrogen atom, a substituted or unsubstituted lower alkyl group, a substituted or unsubstituted cyclic lower alkyl group, a substituted or unsubstituted cyclic lower alkyl-substituted lower alkyl group, a substituted or unsubstituted aryl group, or a substituted or unsubstituted aralkyl group, or $R^4$ and $R^5$ may bind to each other to form a heterocyclic group together with the adjacent nitrogen atom), —$OR^6$ (in the formula, $R^6$ represents a substituted or unsubstituted lower alkyl group, a substituted or unsubstituted cyclic lower alkyl group, a substituted or unsubstituted cyclic lower alkyl-substituted lower alkyl group, a substituted or unsubstituted aryl group, or a substituted or unsubstituted aralkyl group), —$SR^{6a}$ (in the formula, $R^{6a}$ has the same meaning as $R^6$ mentioned above), a substituted or unsubstituted lower alkyl group, a substituted or unsubstituted cyclic lower alkyl group, a substituted or unsubstituted cyclic lower alkyl-substituted lower alkyl group, or a cyano group], $R^2$ represents a substituted or unsubstituted lower alkyl group, a substituted or unsubstituted cyclic lower alkyl group, a substituted or unsubstituted cyclic lower alkyl-substituted lower alkyl group, a substituted or unsubstituted aralkyl group, a substituted or unsubstituted aryl group, a substituted or unsubstituted aromatic heterocyclic group, a substituted or unsubstituted alicyclic heterocyclic group, a halogen atom, a lower alkylthio group, —$NR^7R^8$ (in the formula, $R^7$ and $R^8$ have the same meanings as $R^4$ and $R^5$ mentioned above, respectively), —$CO_2H$, a lower alkoxycarbonyl group, —COHal (in the formula, Hal represents a halogen atom), —$CONR^9R^{10}$ (in the formula, $R^9$ and $R^{10}$ have the same meanings as $R^4$ and $R^5$ mentioned above, respectively) or —CHO, $R^3$ represents a hydrogen atom, a lower alkyl group, cyclic lower alkyl group, a cyclic lower alkyl-substituted lower alkyl group, a substituted or unsubstituted aralkyl group, or a lower alkoxyalkyl group, n represents an integer of from 0 to 3, $V^1$ represents a hydrogen atom, a substituted or unsubstituted lower alkyl group, a substituted or unsubstituted cyclic lower alkyl group, a substituted or unsubstituted cyclic lower alkyl-substituted lower alkyl group, a substituted or unsubstituted aralkyl group, a substituted or unsubstituted aryl group, or a substituted or unsubstituted aromatic heterocyclic group, $V^2$ represents a substituted lower alkyl group, a substituted cyclic lower alkyl group, a substituted cyclic lower alkyl-substituted lower alkyl group, or a substituted or unsubstituted aromatic heterocyclic group, and when $V^1$ represents a hydrogen atom, a lower alkyl group, a cyclic lower alkyl group, a cyclic lower alkyl-substituted lower alkyl group, a substituted or unsubstituted aralkyl group, or a substituted or unsubstituted aryl group, and (a) X—Y-Z represents $R^{1a}N$—C=O (in the formula, $R^{1a}$ represents any of the groups in the definition of the aforementioned $R^1$ excluding a substituted lower alkyl group, a substituted cyclic lower alkyl group and a substituted cyclic lower alkyl-substituted lower alkyl group), and $R^2$ represents a substituted lower alkyl group, a substituted cyclic lower alkyl group, a substituted or unsubstituted aralkyl group, a substituted or unsubstituted alicyclic heterocyclic group, a halogen atom, a lower alkylthio group, —$NR^7R^8$ (in the formula, $R^7$ and $R^8$ have the same meanings as defined above, respectively), —$CO_2H$, a lower alkoxycarbonyl group, —COHal (in the formula, Hal has the same meaning as defined above), —$CONR^9R^{10}$ (in the formula, $R^9$ and $R^{10}$ have the same meanings as those defined above, respectively) or —CHO, (b) X—Y-Z represents $R^1N$—C=O (in the formula, $R^1$ has the same meaning as defined above), and $R^3$ represents a lower alkoxyalkyl group, (c) X—Y-Z represents $R^{1b}N$—C=O (in the formula, $R^{1b}$ represents a substituted lower alkyl group, a substituted cyclic lower alkyl group or a substituted cyclic lower alkyl-substituted lower alkyl group), (d) X—Y-Z represents N=C—W (in the formula, W has the same meaning as defined above), and $R^2$ represents a substituted or unsubstituted lower alkyl group, a substituted or unsubstituted cyclic lower alkyl group, a substituted or unsubstituted cyclic lower alkyl-substituted lower alkyl group, a substituted or unsubstituted aralkyl group, a substituted or unsubstituted aryl group, a substituted or unsubstituted aromatic heterocyclic group, a substituted or unsubstituted alicyclic heterocyclic group, a halogen atom, a lower alkylthio group, —$NR^7R^8$ (in the formula, $R^7$ and $R^8$ have the same meanings as defined above, respectively), —$CO_2H$, a lower alkoxycarbonyl group, —COHal (in the formula, Hal has the same meaning as defined above), —$CONR^9R^{10}$ (in the formula, $R^9$ and $R^{10}$ have the same meanings as defined above, respectively) or —CHO, or (e) X—Y-Z represents N=C—W (in the formula, W has the same meaning as defined above), and $R^3$ represents a lower alkyl group, a cyclic lower alkyl group, a cyclic lower alkyl-substituted lower alkyl group, a substituted or unsubstituted aralkyl group, or a lower alkoxyalkyl group, $V^2$ may represent a lower alkyl group, a cyclic lower alkyl group, a cyclic lower alkyl-substituted lower alkyl group, a substituted or unsubstituted aralkyl group, or a substituted or unsubstituted aryl group; or a pharmacologically acceptable salt thereof wherein the substituent(s) of the substituted aryl group, the substituted aralkyl group, the substituted aromatic heterocyclic group, and the substituted alicyclic heterocyclic group may be the same or different in number of 1 to 3, and are selected from a group consisting of a substituted or unsubstituted lower alkyl group, a substituted or unsubstituted cyclic lower alkyl group, a substituted or unsubstituted aryl group, a substituted or unsubstituted aryloxy group, a substituted or unsubstituted aroyl group, a substituted or unsubstituted aralkyl group, a substituted or unsubstituted aralkyloxy group, a substituted or unsubstituted lower alkenyl group, a substituted or unsubstituted lower alkynyl group, a substituted or unsubstituted lower alkoxy group, a substituted or unsubstituted lower alkoxycarbonyl group, a substituted or unsubstituted lower alkylthio group, a substituted or unsubstituted lower alkylsulfonyl group, a substituted or unsubstituted lower alkanoyl group, a mono- or di-lower alkyl-substituted carbamoyl group, a mono- or di-lower alkyl-substituted amino group, a halogen atom, a carboxyl group, a hydroxyl group, a nitro group, an amino group and a cyano group; wherein the substituent(s) of the substituted lower alkyl group, the substituted cyclic lower alkyl group, the substituted aryl group, the substituted aryloxy group, the substituted aroyl group, the substituted aralkyl group, the substituted aralkyloxy group, the substituted lower alkenyl group, the substituted lower alkynyl group, the substituted lower alkoxy group, the substituted lower alkoxycarbonyl group, the substituted lower alkylthio group, the substituted lower alkylsulfonyl group and the substituted lower alkanoyl group may be the same or different in number of 1 to 3, and are selected from a group consisting of a hydroxyl group, a halogen atom, a carboxyl group, a sulfo group, a phosphono group, and an ester derived from any of these acidic groups; and the substituent(s) of the substituted lower alkyl, the substituted cyclic lower alkyl and the substituted cyclic lower alkyl-substituted lower alkyl group may be the same or different in number of 1 to 3, and are selected from a group consisting of a lower alkoxy group, a hydroxyl group, a cyano group, an azido group, a carboxyl group, a phosphono group, an ester derived from any of these acidic groups, a lower alkylthio group, a lower alkylaminocarbonyl group, a lower alkoxycarbonyl group, a substituted or unsubstituted aromatic heterocyclic group, a substituted or unsubstituted alicyclic heterocyclic group, —NR$^{11}$R$^{12}$ (in the formula, R$^{11}$ and R$^{12}$ may be the same or different and each represents a hydrogen atom, a lower alkyl group, a cyclic lower alkyl group, a lower alkanoyl group, an aryl group, an aralkyl group or an aralkyloxy group, or R$^{11}$ and R$^{12}$ may bind to each other to form a heterocyclic group together with the adjacent nitrogen atom), a halogen atom, an arylsulfonyloxy group which may be substituted with a lower alkyl group, a cyclic lower alkyl group, a lower alkylsulfonyl group, a lower alkylsulfonyloxy group and a trifluoromethanesulfonyloxy group; wherein the substituent(s) of the substituted aromatic heterocyclic group and the substituted alicyclic heterocyclic group have the same meanings as those mentioned above.

Compound (I) or a pharmacologically acceptable salt thereof may exist in the form of a hydrate or a solvate, and these adducts also fall within the scope of the present invention. A type of a solvent that forms the solvate is not particularly limited so long as the solvent is pharmacologically acceptable. For example, ethanol, acetone or the like can be used. Compound (I) may sometimes have one or more asymmetric carbons, and any of optical isomers and diastereoisomers in a pure form, any mixtures of these isomers, racemates and the like fall within the scope of the present invention. When Compound (I) contains a double bond, the bond may be either in Z- or E-configuration. When a tautomer of Compound (I) exists, the tautomer may be in any form of tautomerism and any possible isomers and mixtures thereof fall within the scope of the present invention.

Methods for producing Compound (I) will be explained below.

When any defined group changes under a given reaction condition or is not suitable for carrying out a reaction process in the schemes mentioned below, preparation may be readily carried out by applying methods commonly used in the filed of synthetic organic chemistry such as protection and deprotection of a functional group [see, for example, T. W. Greene, Protective Groups in Organic Synthesis, John Wiley & Sons, Inc. (1981) and the like].

Preparation method 1:

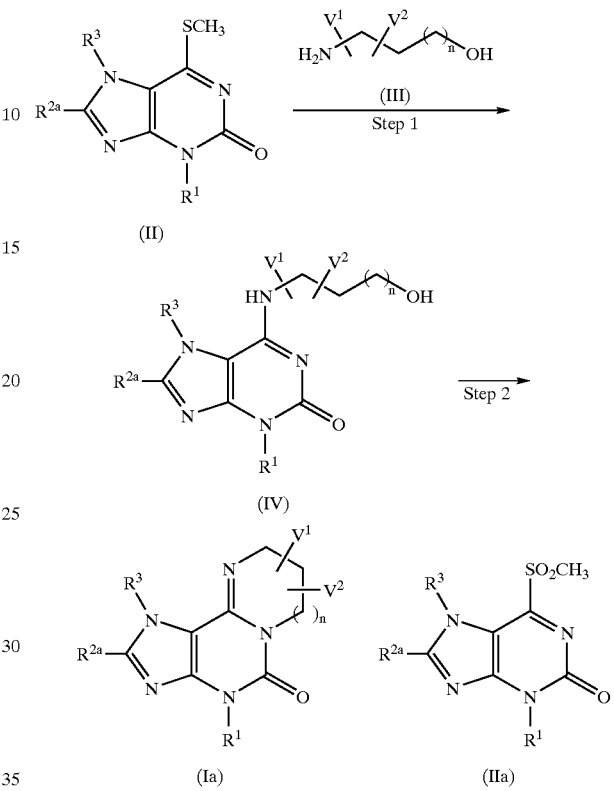

(In the formulas, R$^{2a}$ represents a hydrogen atom, a substituted or unsubstituted lower alkyl group, a substituted or unsubstituted aralkyl group, a substituted or unsubstituted aryl group, or a substituted or unsubstituted aromatic heterocyclic group, and n, R$^1$, R$^3$, V$^1$ and V$^2$ have the same meanings as those defined above, respectively. The lower alkyl group, the aralkyl group, the aryl group, the aromatic heterocyclic group, and substituents of the substituted lower alkyl group, the substituted aralkyl group, the substituted aryl group and the substituted aromatic heterocyclic group have the same meanings as those defined above, respectively.)

Compound (Ia), which corresponds to Compound (I) wherein X—Y-Z is R$^1$N—C═O (in the formula, R$^1$ has the same meaning as defined above), R$^2$ is a hydrogen atom, a substituted or unsubstituted lower alkyl group, a substituted or unsubstituted aralkyl group, a substituted or unsubstituted aryl group, or a substituted or unsubstituted aromatic heterocyclic group, can be produced through Steps 1 and 2 described below from Compound (II), which is a known compound or a compound that can be obtained by a method similar to the known one in a method similar to that described in International Patent Publication WO98/15555, Japanese Patent Unexamined Publication No. 3-204480, Journal of Medicinal Chemistry (J. Med. Chem.), 35, p. 3578, 1992, Journal of Medicinal Chemistry (J. Med. Chem.), 36, p. 2508, 1993, Journal of Heterocyclic Chemistry (J. Heterocycl. Chem.), 30, p. 241, 1993 or the like. According to the methods disclosed in the above references or preparation methods specifically described in the present specification, or with suitable changes of regents and reaction starting materials as well as with optional modifications or alterations of the methods, those skilled in the art can produce Compound (I).

Step 1

Compound (IV) can be obtained by reacting Compound (II) with 1 to 10 equivalents, preferably 2 to 5 equivalents, of Compound (III) without a solvent or in a suitable solvent. Examples of the solvent include, for example, alcohols such as methanol, ethanol, and isopropanol, aromatic hydrocarbons such as toluene and xylene, halogenated hydrocarbons such as dichloroethane, 1,1,2,2-tetrachloroethane and dichlorobenzene, pyridine, N,N-dimethylformamide, N,N-dimethylacetamide, 1-methyl-2-pyrrolidinone, N,N'-dimethylimidazolidin-2-one, dimethyl sulfoxide and so forth, and these solvents are used each alone or as a mixture thereof. The reaction is performed at a temperature between 30° C. and a boiling point of the solvent used and finishes in 5 minutes to 24 hours.

Compound (IV) can also be produced by the following method.

Compound (IV) can be obtained by oxidizing Compound (II) into a sulfone compound (IIa) by treating it with a mono persulfate compound or the like in a suitable solvent, and then removing the solvent, and further reacting the sulfone compound with 1 to 10 equivalents, preferably 2 to 5 equivalents, of Compound (III). Examples of the solvent for the oxidation reaction include, for example, ketones such as acetone and methyl ethyl ketone, alcohols such as methanol and ethanol, halogenated hydrocarbons such as chloroform and dichloroethane, aromatic hydrocarbons such as toluene, ethyl acetate, water and so forth, and these solvents are used each alone or as a mixture thereof. When a two-phase system is used, the reaction may be performed by mixing a phase transfer catalyst. Examples of the phase transfer catalyst include tetrabutylammonium chloride, benzyltributylammonium chloride, tetrabutylammonium hydrogensulfate and so forth, and the reaction is performed at a temperature between 0° C. and room temperature and finishes in 1 to 12 hours. Examples of the solvent for the amination include, for example, aromatic hydrocarbons such as toluene and xylene, halogenated hydrocarbons such as dichloroethane, 1,1,2,2-tetrachloroethane and dichlorobenzene, pyridine, N,N-dimethylformamide, N,N-dimethylacetamide, 1-methyl-2-pyrrolidinone, N,N'-dimethylimidazolidin-2-one, dimethyl sulfoxide and so forth, and these solvents are used each alone or as a mixture thereof. The reaction is performed at a temperature between room temperature and a boiling point of the solvent used and finishes in 1 to 24 hours.

Compound (II) as a starting material can be obtained according to a known method [Journal of Chemical Society Perkin I (J. Chem. Soc. Perkin I), p. 739, 1973 or Journal of Heterocyclic Chemistry (J. Heterocycl. Chem.), 30, p. 241, 1993] or a similar method thereto.

Compound (III) as a starting material can be obtained by, for example, treating a known amino acid derivative with 1 to 10 equivalents, preferably 2 to 5 equivalents, of a reducing agent, for example, a metal hydrogen complex compound such as lithium aluminum hydride, sodium borohydride or lithium borohydride, diborane or the like in a suitable solvent. Examples of the solvent include, for example, diethyl ether, tetrahydrofuran, diethylene glycol dimethyl ether and so forth. The reaction is performed at a temperature between 0° C. and a boiling point of the solvent used and finishes in 30 minutes to 24 hours. When the amino group of the starting amino acid derivative is protected, its deprotection can be carried out by using a method usually used in the filed of synthetic organic chemistry.

Step 2

Compound (Ia) can be obtained by treatment of Compound (IV) with 1 equivalent to large excess, preferably large excess, of a halogenating agent such as thionyl chloride or phosphorus oxychloride, or with an inorganic acid such as hydrochloric acid, hydrobromic acid, hydroiodic acid or phosphoric acid, or alternatively, with 1 to 5 equivalents, preferably 1 to 2 equivalents, of a sulfonylating agent such as benzenesulfonyl chloride, p-toluenesulfonyl chloride, methanesulfonyl chloride or trifluoromethanesulfonyl chloride in the presence of 1 to 10 equivalents, preferably 1 to 5 equivalents, of an organic base such as triethylamine, diisopropylethylamine or pyridine or an inorganic base such as potassium carbonate, sodium carbonate, potassium hydrogen carbonate, sodium hydrogen carbonate, potassium hydroxide, or sodium hydroxide, without a solvent or in a suitable solvent. Examples of the solvent include, for example, halogenated hydrocarbons such as methylene chloride, chloroform and dichloroethane, tetrahydrofuran, N,N-dimethylformamide, dimethyl sulfoxide and so forth, and these solvents are used each alone or as a mixture thereof. The reaction is performed at a temperature between −10° C. and 150° C., preferably at a temperature between 50° C. and 70° C., and finishes in 5 minutes to 24 hours.

Preparation method 2:

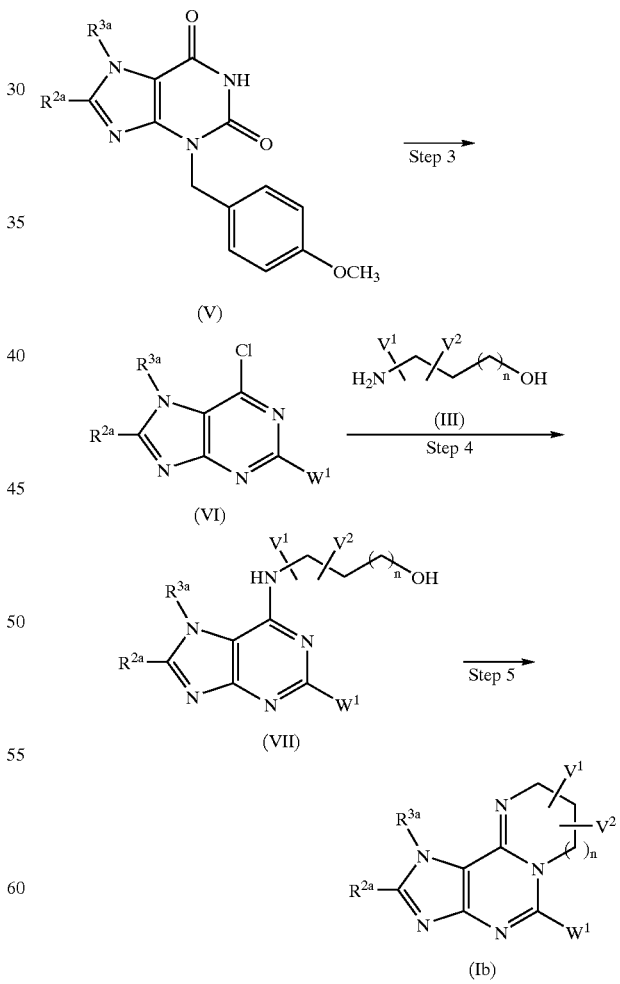

(In the formulas, $R^{3a}$ represents a lower alkyl group or a substituted or unsubstituted aralkyl group, $W^1$ represents a halogen atom, and n, $R^{2a}$, $V^1$, and $V^2$ have the same meanings as those defined above, respectively. The lower alkyl group, the aralkyl group, the halogen atom, and the substituents of the substituted aralkyl group have the same meanings as those defined above, respectively.)

Compound (Ib), which corresponds to Compound (I) wherein X—Y-Z is N=C—$W^1$ (in the formula, $W^1$ has the same meaning as defined above), $R^2$ is a hydrogen atom, a substituted or unsubstituted lower alkyl group, a substituted or unsubstituted aralkyl group, a substituted or unsubstituted aryl group, or a substituted or unsubstituted aromatic heterocyclic group, and $R^3$ is a lower alkyl group or a substituted or unsubstituted aralkyl group, can be produced through Steps 3 to 5 from Compound (V) which can be obtained by a known method (Japanese Patent Unexamined Publication No. 8-500344) or a similar method thereto.

Step 3

Compound (VI) can be obtained by treatment of Compound (V) with 1 equivalent to large excess, preferably large excess, of a halogenating agent, used alone or in combination, such as phosphorus pentachloride or phosphorus oxychloride without a solvent or in a suitable solvent, optionally with addition of 1 to 10 equivalents, preferably 1 to 3 equivalents, of a tertiary amine such as triethylamine or diisopropylethylamine. Examples of the solvent include, for example, halogenated hydrocarbons such as chloroform and dichloroethane. The reaction is performed at a temperature between 70° C. and 150° C., preferably at a temperature between 100° C. and 130° C., and finishes in 1 to 24 hours.

Step 4

Compound (VII) can be obtained by reacting Compound (VI) with 2 to 20 equivalents, preferably 2 to 5 equivalents, of Compound (III) in a suitable solvent, optionally in the presence of 1 to 10 equivalents, preferably 1 to 3 equivalents, of a tertiary amine such as triethylamine or diisopropylethylamine or an inorganic base such as sodium carbonate, cesium carbonate, or sodium hydrogen carbonate. Examples of the solvent include, for example, N,N-dimethylformamide, dimethyl sulfoxide, 1-methyl-2-pyrrolidinone, acetonitrile and so forth, and these solvents are used each alone or as a mixture thereof. The reaction is performed at a temperature between 0° C. and a boiling point of the solvent used, preferably at a temperature between 0° C. and room temperature, and finishes in 1 to 24 hours, preferably in 1 to 5 hours.

Step 5

Compound (Ib) can be produced from Compound (VII) in a manner similar to that of Step 2.

Preparation method 3:

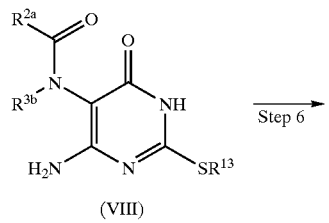

(VIII)

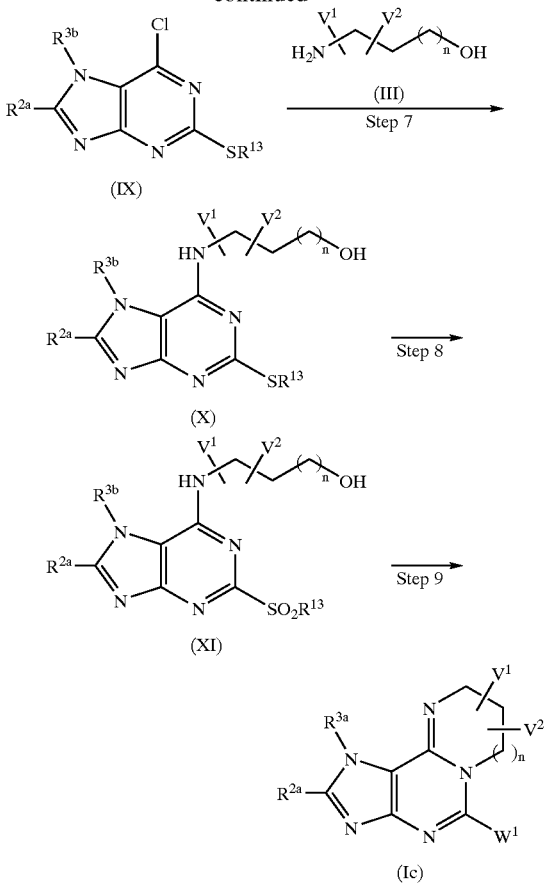

(In the formulas, $R^{3b}$ represents a hydrogen atom, a lower alkyl group, or a substituted or unsubstituted aralkyl group, $R^{13}$ represents a lower alkyl group, and n, $R^{2a}$, $V^1$, $V^2$, and $W^1$ have the same meanings as those defined above, respectively. The lower alkyl group, the aralkyl group, and the substituents of the substituted aralkyl group have the same meanings as those defined above, respectively.)

Compound (Ic), which corresponds to Compound (I) wherein X—Y-Z is N=C—$W^1$ (in the formula, $W^1$ has the same meaning as defined above), $R^2$ is a hydrogen atom, a substituted or unsubstituted lower alkyl group, a substituted or unsubstituted aralkyl group, a substituted or unsubstituted aryl group, or a substituted or unsubstituted aromatic heterocyclic group, and $R^3$ is a hydrogen atom, a lower alkyl group, or a substituted or unsubstituted aralkyl group, can be produced through Steps 6 to 9.

Step 6

Compound (IX) can be produced from Compound (VIII) in a manner similar to that of Step 3.

Step 7

Compound (X) can be obtained by reacting Compound (IX) with 1 to 10 equivalents, preferably 2 to 5 equivalents, of Compound (III) in a suitable solvent, optionally in the presence of 1 to 10 equivalents, preferably 1 to 3 equivalents, of a tertiary amine such as triethylamine or diisopropylethylamine or inorganic base such as sodium carbonate, cesium carbonate or sodium hydrogen carbonate. Examples of the solvent include, for example, alcohols such as n-propanol, isopropanol and n-butanol, aromatic hydrocarbons such as toluene and xylene, halogenated hydrocarbons such as dichloroethane, 1,1,2,2-tetrachloroethane and dichlorobenzene, pyridine, N,N-dimethylformamide, N,N-dimethylacetamide, 1-methyl-2-pyrrolidinone, N,N'-dimethylimidazolidin-2-one, dimethyl sulfoxide and so forth, and these solvents are used each alone or as a mixture thereof. The reaction is performed at a temperature between 80° C. and 150° C. and finishes in 2 to 12 hours.

Step 8

Compound (XI) can be obtained by oxidizing Compound (X) with 1 to 10 equivalents, preferably 2 to 5 equivalents, of a monopersulfate compound in a suitable solvent, optionally in the presence of 0.1 to 0.5 equivalent of a phase transfer catalyst such as tetrabutylammonium chloride, benzyltributylammonium chloride or tetrabutylammonium hydrogensulfate. Examples of the solvent include, for example, ketones such as acetone and methyl ethyl ketone, alcohols such as methanol and ethanol, water and so forth, and these solvents are used each alone or as a mixture thereof. The reaction is performed at a temperature between 0° C. and room temperature and finishes in 1 to 12 hours.

Step 9

Compound (Ic) can be produced from Compound (XI) in a manner similar to that of Step 2.

Further, Compound (Ic) obtained by the aforementioned preparation method can also be used as a synthetic intermediate and converted into another Compound (I).

Step 10

Compound (Iaa), which corresponds to Compound (Ia) wherein $V^1$ or $V^2$ is a lower alkyl group substituted with —$NR^{11}R^{12}$ (in the formula, $R^{11}$ and $R^{12}$ have the same meanings as defined above, respectively), can be obtained by reacting Compound (Iab), which corresponds to Compound (Ia) wherein $V^1$ or $V^2$ is a substituted lower alkyl group having a suitable leaving group such as a halogen atom, a methanesulfonyloxy group, a toluenesulfonyloxy group, or a trifluoromethanesulfonyloxy group, with 2 to 20 equivalents, preferably 5 to 10 equivalents, of $HNR^{11}R^{12}$ in a suitable solvent, optionally in the presence of 1 to 10 equivalents, preferably 1 to 3 equivalents, of a tertiary amine such as triethylamine or diisopropylethylamine or an inorganic base such as sodium carbonate, cesium carbonate or sodium hydrogen carbonate. Examples of the solvent include, for example, water, alcohols such as methanol and ethanol, halogenated hydrocarbons such as methylene chloride, acetonitrile, tetrahydrofuran, N,N-dimethylformamide, dimethyl sulfoxide and so forth, and these solvents are used each alone or as a mixture thereof. The reaction is performed at a temperature between 0° C. and a boiling point of the solvent used, preferably at a temperature between 0° C. and room temperature, and finishes in 1 to 24 hours, preferably in 1 to 5 hours.

Further, Compound (Iaa1), which corresponds to Compound (Iaa) wherein each of $R^{11}$ and $R^{12}$ represents a hydrogen atom, can also be produced by the method described below.

Preparation method 4:

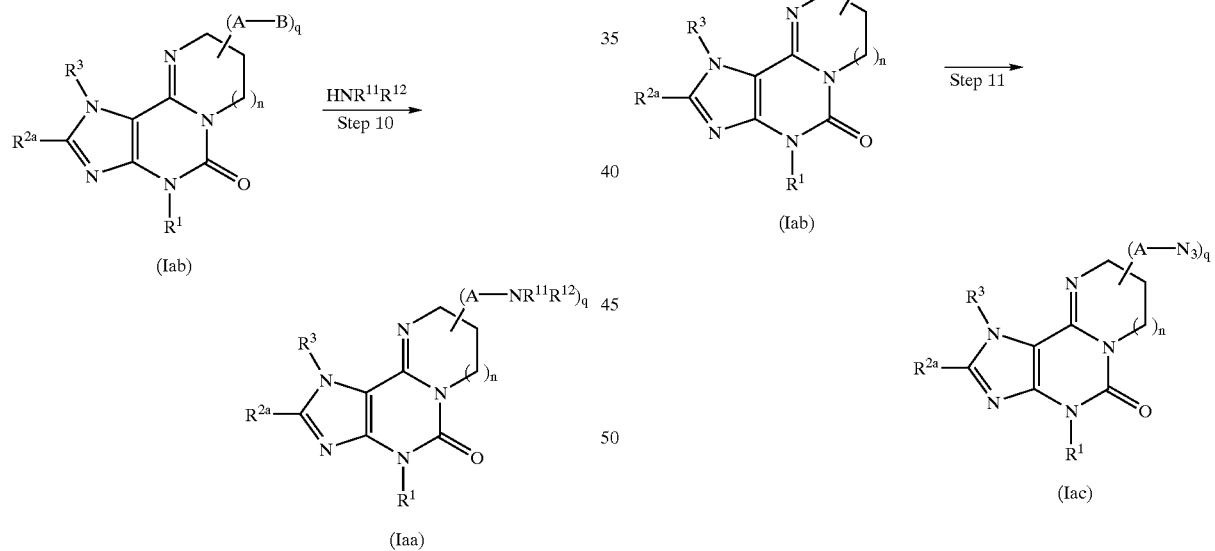

(In the formulas, A represents a lower alkylene group, B represents a suitable leaving group such as a halogen atom, a methanesulfonyloxy group, a toluenesulfonyloxy group, or a trifluoromethanesulfonyloxy group, q represents 1 or 2, and n, $R^1$, $R^{2a}$, $R^3$, $R^{11}$ and $R^{12}$ have the same meanings as those defined above, respectively. The lower alkylene group has the same meaning as the aforementioned alkylene moiety, and the halogen atom has the same meaning as defined above. When q is 2, two of A-B or A-$NR^{11}R^{12}$ may be the same or different, and the same shall apply to the following description.)

(In the formulas, A, B, n, q, $R^1$, $R^{2a}$ and $R^3$ have the same meanings as those defined above, respectively.)

Step 11

Compound (Iab) can be reacted with 1 to 5 equivalents of a suitable azidating agent such as sodium azide, potassium azide, lithium azide, or trimethylsilyl azide in a suitable solvent to obtain corresponding Azide compound (Iac). Examples of the solvent include, for example, water, alcohols such as methanol and ethanol, tetrahydrofuran, diethylene glycol dimethyl ether, N,N-dimethylformamide and so forth, and these solvents are used each alone or as a mixture thereof. The reaction is performed at a temperature between 0° C. and 160° C., preferably at a temperature between room temperature and 100° C., and finishes in 1 to 72 hours, preferably in 1 to 24 hours.

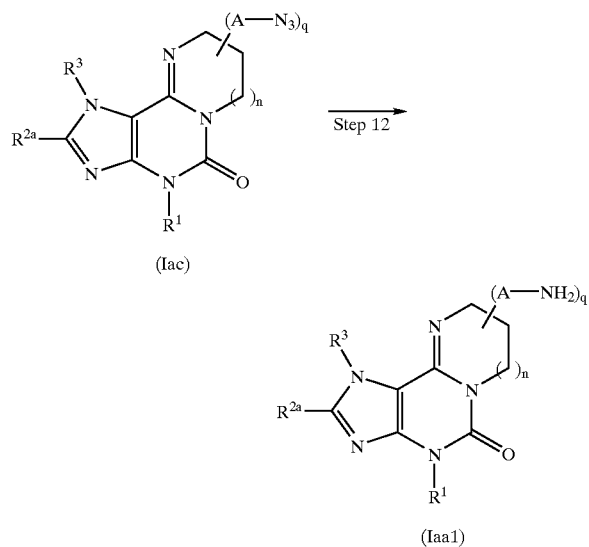

(Iac)

(Iaa1)

(In the formulas, A, n, q, $R^1$, $R^{2a}$ and $R^3$ have the same meanings as those defined above, respectively.)

Step 12

Compound (Iaa1) can be obtained by reducing Azide Compound (Iac) obtained in Step 11 in a suitable solvent under ordinary pressure or positive pressure of hydrogen flow in the presence of a catalyst such as palladium, nickel or platinum, optionally in the presence of an inorganic base such as calcium carbonate. Examples of the solvent include, for example, alcohols such as methanol and ethanol, tetrahydrofuran and so forth, and these solvents are used each alone or as a mixture thereof. The reaction is performed at a temperature between room temperature and a boiling point of the solvent used and finishes in 1 to 24 hours, preferably in 1 to 6 hours.

Compound (Iaa1) can also be obtained by treating Azide Compound (Iac) mentioned above in a solvent such as water, methanol, ethanol, toluene, or diethyl ether in the presence of a reducing agent such as sodium borohydride, lithium aluminum hydride, borane, or triphenylphosphine at a temperature between 0° C. and a boiling point of the solvent used for 1 to 24 hours, preferably for 1 to 6 hours.

Furthermore, Compound (Iaa1) can also be produced by the method described below.

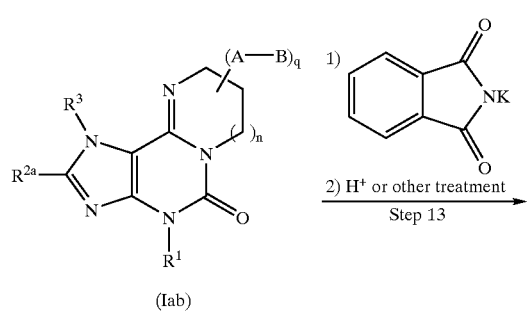

(Iab)

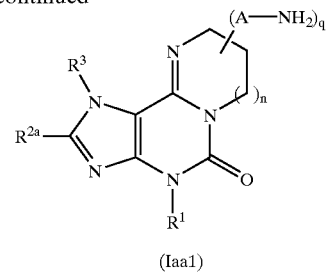

(Iaa1)

(In the formulas, A, B, n, q, $R^1$, $R^{2a}$ and $R^3$ have the same meanings as those defined above, respectively.)

Step 13

Compound (Iab) can be reacted with 1 to 5 equivalents of phthalimide potassium salt in a suitable solvent to obtain a corresponding N-substituted phthalimide compound. Examples of the solvent include tetrahydrofuran, diethylene glycol dimetyl ether, N,N-dimethylformamide and so forth, and these solvents are used each alone or as a mixture thereof. The reaction is performed at a temperature between 0° C. and 160° C., preferably at a temperature between room temperature and 120° C., and finishes in 1 to 72 hours, preferably in 1 to 6 hours. Subsequently, the obtained N-substituted phthalimide compound can be hydrolyzed with an acid by using hydrochloric acid, sulfuric acid or the like, or reacted with large excess of hydrazine in a suitable solvent to obtain Compound (Iaa1). Examples of the solvent include, for example, chloroform, methanol, ethanol, tetrahydrofuran and so forth, and these solvents are used each alone or as a mixture thereof. The reaction is performed at a temperature between room temperature and a boiling point of the solvent used and finishes in 1 to 24 hours, preferably in 1 to 12 hours.

Compound (Iaa2), which corresponds to Compound (Iaa) wherein $R^{11}$ and $R^{12}$ form a heterocyclic group together with the adjacent nitrogen atom can also be produced by the method described below.

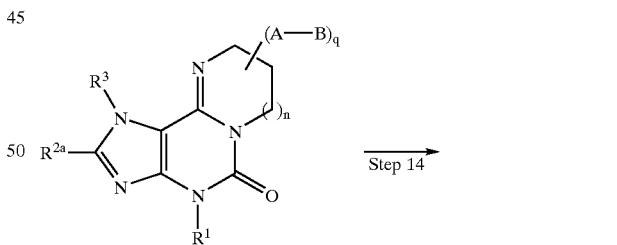

(Iab)

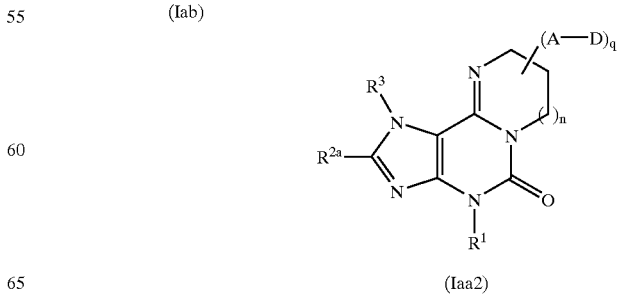

(Iaa2)

(In the formulas, D represents a heterocyclic group formed together with the adjacent nitrogen atom, and A, B, n, q, $R^1$, $R^{2a}$ and $R^3$ have the same meanings as those defined above, respectively. The heterocyclic group formed together with the adjacent nitrogen atom has the same meaning as defined above.)

Step 14

Compound (Iaa2) can also be obtained by reacting Compound (Iab) with a corresponding heterocyclic compound in a suitable solvent in the presence of an inorganic base such as potassium carbonate, sodium carbonate, or cesium carbonate, or with a metal salt of a corresponding heterocyclic compound, which is prepared by using a metal hydride such as sodium hydride or potassium hydride or a metal lower alkoxide such as sodium methoxide, sodium ethoxide, or potassium tert-butoxide. Examples of the solvent include ethers such as 1,4-dioxane and tetrahydrofuran, alcohols such as methanol and ethanol, N,N-dimethylformamide, dimethyl sulfoxide and so forth, and these solvents are used each alone or as a mixture thereof. The reaction is performed at a temperature between 0° C. and a boiling point of the solvent used and finishes in 1 to 24 hours, preferably in 1 to 6 hours.

Compound (Iaa2) can also be produced by converting an amino group of Compound (Iaa1) into a heterocyclic group formed together with the adjacent nitrogen atom.

Preparation Method 5:

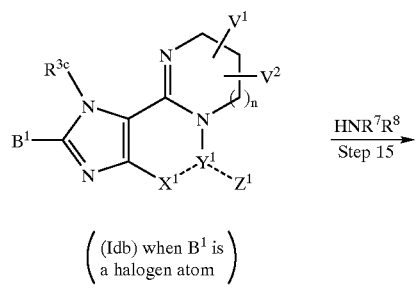

(Idb) when $B^1$ is a halogen atom

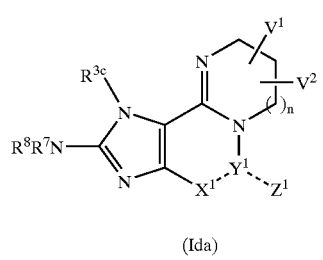

(Ida)

[In the formulas, $R^{3c}$ represents a lower alkyl group, a substituted or unsubstituted aralkyl group, or a lower alkoxyalkyl group, $X^1$—$Y^1$-$Z^1$ represents $R^1$N—C=O (in the formula, $R^1$ has the same meaning as defined above) or N=C—$W^2$ (in the formula, $W^2$ represents a group defined for the aforementioned W excluding a halogen atom, $B^1$ has the same meaning as the aforementioned B, and n, $R^7$, $R^8$, $V^1$ and $V^2$ have the same meanings as those defined above, respectively. The lower alkyl group, the aralkyl group, the lower alkoxyalkyl group, the halogen atom, and the substituents of the substituted aralkyl group have the same meanings as those defined above, respectively.)

Step 15

In Compound (Id) which corresponds to Compound (I) wherein X—Y-Z is $R^1$N—C=O (in the formula, $R^1$ has the same meaning as defined above) or N=C—$W^2$ (in the formula, $W^2$ has the same meaning as defined above), and $R^3$ is a lower alkyl group, a substituted or unsubstituted aralkyl group, or a lower alkoxyalkyl group, Compound (Ida), which corresponds to Compound (Id) wherein $R^2$ is —NR$^7$R$^8$ (in the formula, $R^7$ and $R^8$ have the same meanings as those defined above, respectively), can be obtained by reacting Compound (Idb) which corresponds to Compound (Id) wherein $R^2$ is a halogen atom, or said compound in which the halogen atom is replaced with a suitable leaving group such as a methanesulfonyloxy group, a toluenesulfonyloxy group, or a trifluoromethanesulfonyloxy group, with HNR$^7$R$^8$ (in the formula, $R^7$ and $R^8$ have the same meanings as those defied above, respectively) in a manner similar to that of Step 10.

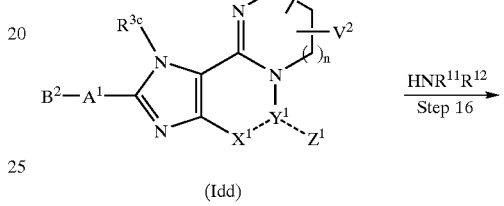

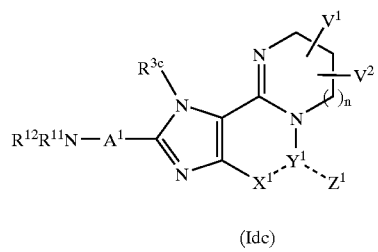

(In the formula, $A^1$ has the same meaning as the aforementioned A, $B^2$ has the same meaning as the aforementioned B, and n, $R^{3c}$, $R^{11}$, $R^{12}$, $V^1$, $V^2$ and $X^1$—$Y^1$-$Z^1$ have the same meanings as those defined above, respectively.)

Step 16

Compound (Idc), which corresponds to Compound (Id) wherein $R^2$ is a lower alkyl group substituted with —NR$^{11}$R$^{12}$ (in the formula, $R^{11}$ and $R^{12}$ have the same meanings as those defined above, respectively), can be obtained by reacting Compound (Idd), which corresponds to Compound (Id) wherein $R^2$ is a lower alkyl group substituted with a suitable leaving group such as a halogen atom, a methanesulfonyloxy group, a toluenesulfonyloxy group, or a trifluoromethanesulfonyloxy group, with HNR$^{11}$R$^{12}$ (in the formula, $R^{11}$ and $R^{12}$ have the same meanings as those defined above, respectively) in a manner similar to that of Step 10.

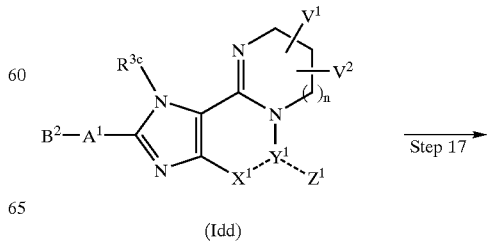

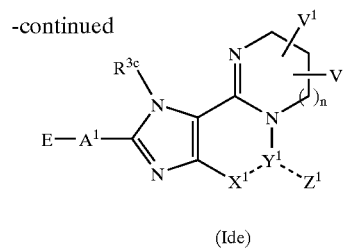

(Ide)

(In the formulas, E represents a lower alkoxy group, and $A^1$, $B^2$, n, $R^{3c}$, $V^1$, $V^2$ and $X^1$—$Y^1$-$Z^1$ have the same meanings as those defined above, respectively. The lower alkoxy group has the same meaning as defined above.)

Step 17

Compound (Ide), which corresponds to Compound (Id) wherein $R^2$ is a lower alkyl group substituted with a lower alkoxy group, can be obtained by treating Compound (Idd) in a lower alcoholic solution of a metal salt of a corresponding lower alcohol prepared with metallic sodium or a metal hydride such as sodium hydride or potassium hydride. The reaction is performed at a temperature between 0° C. and a boiling point of the solvent used and finishes in 1 to 24 hours, preferably in 1 to 6 hours.

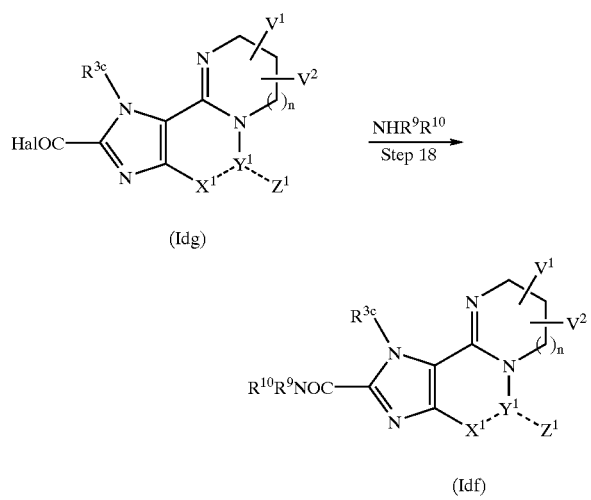

(In the formulas, Hal, n, $R^{3c}$, $R^9$, $R^{10}$, $V^1$, $V^2$ and $X^1$—$Y^1$-$Z^1$ have the same meanings as those defined above, respectively.)

Step 18

Compound (Idf), which corresponds to Compound (Id) wherein $R^2$ is —$CONR^9R^{10}$ (in the formula, $R^9$ and $R^{10}$ have the same meanings as those defined above, respectively), can be obtained by reacting Compound (Idg), which corresponds to Compound (Id) wherein $R^2$ is —COHal (in the formula, Hal has the same meaning as defined above), with 2 to 20 equivalents, preferably 5 to 10 equivalents, of $HNR^9R^{10}$ (in the formula, $R^9$ and $R^{10}$ have the same meanings as defined above, respectively) without a solvent or in a suitable solvent. Examples of the solvent include, for example, N,N-dimethylformamide, dimethyl sulfoxide and so forth. The reaction is performed at a temperature between 0° C. and room temperature, preferably at room temperature, and finishes in 12 to 48 hours, preferably in 24 hours.

Preparation method 6:

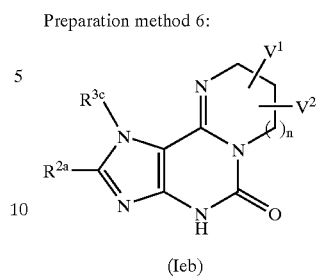

(Ieb)

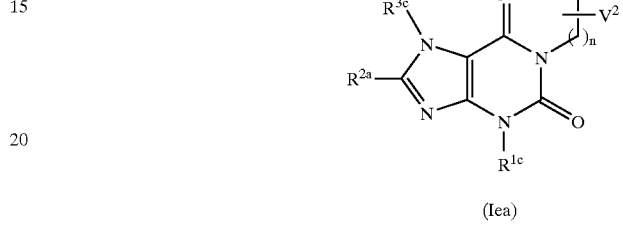

(Iea)

(In the formulas, $R^{1c}$ represents a group defined for $R^1$ excluding a hydrogen atom, and n, $R^{2a}$, $R^{3c}$, $V^1$ and $V^2$ have the same meanings as those defined above, respectively.)

Step 19

In Compound (Ie) which corresponds to Compound (I) wherein X—Y-Z is $R^1N$—C=O (in the formula, $R^1$ has the same meaning as defined above), $R^2$ is a hydrogen atom, a substituted or unsubstituted lower alkyl group, a substituted or unsubstituted aralkyl group, a substituted or unsubstituted aryl group, or a substituted or unsubstituted aromatic heterocyclic group, and $R^3$ is a lower alkyl group, a substituted or unsubstituted aralkyl group, or a lower alkoxyalkyl group, Compound (Iea), which corresponds to Compound (Ie) wherein $R^1$ is a substituted or unsubstituted lower alkyl group, a substituted or unsubstituted aralkyl group, a substituted or unsubstituted aryl group, or a substituted or unsubstituted aromatic heterocyclic group, can be obtained by reacting Compound (Ieb), which corresponds to Compound (Ie) wherein $R^1$ is hydrogen atom, with a substituted or unsubstituted lower alkyl group, a substituted or unsubstituted aralkyl group, a substituted or unsubstituted aryl group, or a substituted or unsubstituted aromatic heterocyclic ring which is substituted with a suitable leaving group such as a halogen atom, a methanesulfonyloxy group, a toluenesulfonyloxy group, or a trifluoromethanesulfonyloxy group in a suitable solvent in the presence of an inorganic base such as potassium carbonate, sodium carbonate or cesium carbonate. The reaction is performed at a temperature between 0° C. and a boiling point of the solvent used, preferably at room temperature, and finishes in 1 to 24 hours, preferably in 1 to 6 hours.

Preparation method 7:

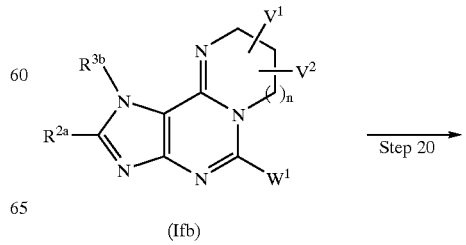

(Ifb)

-continued

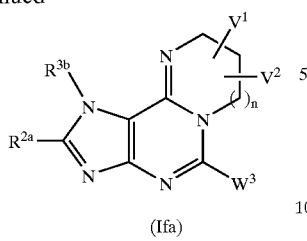

(Ifa)

[In the formulas, $W^3$ represents a substituted or unsubstituted alicyclic heterocyclic group, —$NR^4R^5$ (in the formula, $R^4$ and $R^5$ have the same meanings as those defined above, respectively), —$OR^6$ (in the formula, $R^6$ has the same meaning as defined above), —$SR^{6a}$ (in the formula, $R^{6a}$ has the same meaning as defined above), a substituted or unsubstituted lower alkyl group, or a cyano group, and n, $R^{2a}$, $R^{3a}$, $V^1$, $V^2$ and $W^1$ have the same meanings as those defined above, respectively. The alicyclic heterocyclic group, the lower alkyl group, and the substituents of the substituted alicyclic heterocyclic group and the substituted lower alkyl group have the same meanings as those defined above, respectively.]

Step 20

In Compound (If) which corresponds to Compound (I) wherein X—Y-Z is N=C—W (in the formula, W has the same meaning as defined above), $R^2$ is a hydrogen atom, a substituted or unsubstituted lower alkyl group, a substituted or unsubstituted aralkyl group, a substituted or unsubstituted aryl group, or a substituted or unsubstituted aromatic heterocyclic group, and $R^3$ is a hydrogen atom, a lower alkyl group, or a substituted or unsubstituted aralkyl group, Compound (Ifa), which corresponds to Compound (If) wherein W represents a substituted or unsubstituted alicyclic heterocyclic group, —$NR^4R^5$ (in the formula, $R^4$ and $R^5$ have the same meanings as those defined above, respectively), —$OR^6$ (in the formula, $R^6$ has the same meaning as defined above), —$SR^{6a}$ (in the formula, $R^{6a}$ has the same meaning as defined above), a substituted or unsubstituted lower alkyl group, or a cyano group, can be obtained by reacting Compound (Ifb) which corresponds to Compound (If) wherein W is a halogen atom in a suitable solvent with (a) $HNR^4R^5$ (in the formula, $R^4$ and $R^5$ have the same meanings as those defined above, respectively) or an alicyclic heterocyclic ring in the presence of an inorganic base such as potassium carbonate, sodium carbonate, or cesium carbonate, or a metal salt of $HNR^4R^5$ (in the formula, $R^4$ and $R^5$ have the same meanings as those defined above, respectively) or an alicyclic heterocyclic ring prepared by using a metal hydride such as sodium hydride or potassium hydride or a metal lower alkoxide such as sodium methoxide, sodium ethoxide, or potassium tert-butoxide, (b) a metal salt of $R^6OH$ (in the formula, $R^6$ has the same meaning as defined above) or $R^{6a}SH$ (in the formula, $R^{6a}$ has the same meaning as defined above) prepared with metallic sodium or a metal hydride such as sodium hydride or potassium hydride, (c) an alkylating agent such as a substituted or unsubstituted lower alkyl lithium, or a substituted or unsubstituted lower alkyl magnesium bromide, or (d) a cyanating agent such as sodium cyanide or potassium cyanide. Examples of the solvent include, for example, methanol, ethanol, acetonitrile, tetrahydrofuran, diethyl ether, 1,4-dioxane, N,N-dimethylformamide, dimethyl sulfoxide and so forth, and these solvents are used each alone or as a mixture thereof. The reaction is performed at a temperature between 0° C. and a boiling point of the solvent used, preferably at a temperature between 0° C. and 100° C., and finishes in 1 to 24 hours, preferably in 1 to 5 hours.

Intermediate compounds and target compounds obtained in the aforementioned preparation methods can be isolated and purified by purification methods ordinarily used in the field of synthetic organic chemistry, for example, neutralization, filtration, extraction, washing, drying, concentration, recrystallization, various chromatography techniques and or the like. Intermediate compounds may also be used for subsequent reactions without particular purification. For the preparation of salts of Compound (I), a compound in a free form can be dissolved or suspended in a suitable solvent, followed by addition of a suitable acid or a base to form a salt, which may be separated and purified as required. It is also possible to convert a target substance obtained in a form of a salt into a compound in a free form and then convert the resulting product into a desired salt.

Specific examples of Compound (I) obtainable by the aforementioned preparation methods are shown in Table 1.

TABLE 1 (1)

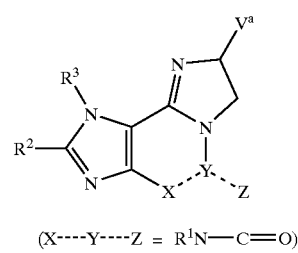

(I)

(X----Y----Z = $R^1N$—C=O)

| Compound No. | $R^1$ | $R^2$ | $R^3$ | $V^a$ |
|---|---|---|---|---|
| 1 | $CH_3(CH_2)_2$ | cyclopentyl | H | 4-pyridyl |
| 2 | $CH_3(CH_2)_2$ | cyclopentyl | H | 4-pyridyl |
| 3 | $CH_3(CH_2)_2$ | cyclopentyl | H | 2-pyridyl |
| 4 | $CH_3(CH_2)_2$ | cyclopentyl | H | 3-pyridyl |
| 5 | $CH_3(CH_2)_2$ | cyclopentyl | H | 2-methylthiazolyl |
| 6 | $CH_3(CH_2)_2$ | cyclopentyl | H | pyrazinyl |
| 7 | $CH_3(CH_2)_2$ | cyclopentyl | H | pyrimidinyl |

TABLE 1 (1)-continued
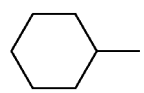
(X----Y----Z = R¹N—C=O)
| Compound No. | R¹ | R² | R³ | V$^a$ |
|---|---|---|---|---|
| 8 | $CH_3(CH_2)_2$ | $CH_3(CH_2)_2$ | H |  |
| 9 | $CH_3(CH_2)_2$ | 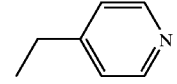 | H | 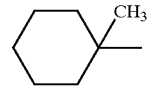 |
| 10 | $CH_3(CH_2)_2$ | 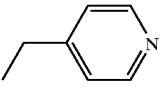 | H | 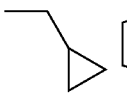 |
TABLE 1 (1)-continued
(X----Y----Z = R¹N—C=O)
| Compound No. | R¹ | R² | R³ | V$^a$ |
|---|---|---|---|---|
| 11 | $CH_3(CH_2)_2$ | $(CH_3)_3C$ | H | 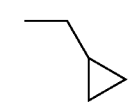 |
| 12 | $CH_3(CH_2)_2$ | 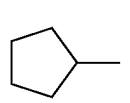 | H | 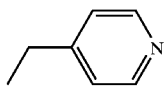 |
| 13 | $CH_3(CH_2)_2$ | H | H | |
TABLE 1 (2)
(I)
(X----Y----Z = R¹N—C=O)
| Compound No. | R¹ | R² | R³ | V$^a$ |
|---|---|---|---|---|
| 14 | | | H | |
| 15 | | $(CH_3)_3C$ | H | |
| 16 | $CH_2CH_3$ | | H | |

TABLE 1 (2)-continued

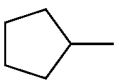

(X----Y----Z = R¹N—C=O)

| Compound No. | R¹ | R² | R³ | Vᵃ |
|---|---|---|---|---|
| 17 | (CH₂)₂CH₃ | cyclopentyl-CH₂- | -CH₂-C₆H₅ | -CH₂CH₂-O-S(O)₂-CH₃ |
| 18 | (CH₂)₂CH₃ | cyclopentyl-CH₂- | -CH₂CH₂-OCH₃ | -CH₂CH₂-O-S(O)₂-CH₃ |
| 19 | (CH₂)₂CH₃ | cyclopentyl-CH₂- | -CH₂CH₂-OCH₃ | -CH₂CH₂-phthalimide |
| 20 | (CH₂)₂CH₃ | cyclopentyl-CH₂- | H | -CH₂CH₂-NH₂ |
| 21 | (CH₂)₂CH₃ | cyclopentyl-CH₂- | H | -CH₂CH₂-pyrazol-1-yl |
| 22 | (CH₂)₂CH₃ | cyclopentyl-CH₂- | H | -CH₂CH₂-imidazol-1-yl |
| 23 | (CH₂)₂CH₃ | cyclopentyl-CH₂- | H | -CH₂CH₂-1,2,4-triazol-1-yl |
| 24 | (CH₂)₂CH₃ | cyclopentyl-CH₂- | H | -CH₂CH₂-pyrrol-1-yl |
| 25 | (CH₂)₂CH₃ | cyclopentyl-CH₂- | H | -CH₂CH₂-benzimidazol-1-yl |

TABLE 1 (3)

(I)

(X----Y----Z = R¹N—C=O)

| Compound No. | R¹ | R² | R³ | Vᵃ |
|---|---|---|---|---|
| 26 | (CH₂)₂CH₃ | cyclopentyl | H | -CH₂CH₂Cl |
| 27 | (CH₂)₂CH₃ | cyclopentyl | H | -CH₂-NH-phenyl |
| 28 | (CH₂)₂CH₃ | cyclopentyl | H | -CH₂-piperidinyl |
| 29 | (CH₂)₂CH₃ | cyclopentyl | H | -CH₂-pyrrolidinyl |
| 30 | (CH₂)₂CH₃ | cyclopentyl | H | -CH₂-morpholinyl |
| 31 | (CH₂)₂CH₃ | cyclopentyl | H | -CH₂-(4-benzylpiperazin-1-yl) |
| 32 | (CH₂)₂CH₃ | cyclopentyl | H | -CH₂-(4-phenylpiperazin-1-yl) |
| 33 | (CH₂)₂CH₃ | cyclopentyl | H | -CH₂-(4-benzylpiperidin-1-yl) |
| 34 | (CH₂)₂CH₃ | cyclopentyl | H | -CH₂-N(H)-CH₂-phenyl |

TABLE 1 (3)-continued
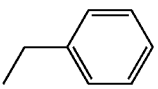
(X----Y----Z = R¹N—C=O)
| Compound No. | R¹ | R² | R³ | Vᵃ |
|---|---|---|---|---|
| 35 | CH₃(CH₂)₂ | Br | 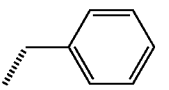 | 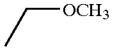 |
| 36 | CH₃(CH₂)₂ | SCH₃ | 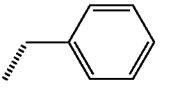 | 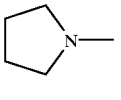 |
| 37 | CH₃(CH₂)₂ | 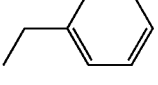 | 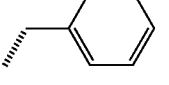 | 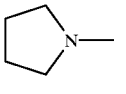 |
TABLE 1 (4)
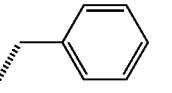
(X----Y----Z = R¹N—C=O)
| Compound No. | R¹ | R² | R³ | Vᵃ |
|---|---|---|---|---|
| 38 | (CH₂)₂CH₃ | 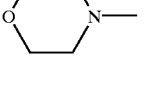 | H | 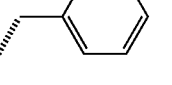 |
| 39 | (CH₂)₂CH₃ | 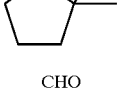 | H | 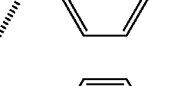 |
| 40 | (CH₂)₂CH₃ | 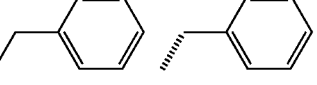 | H | 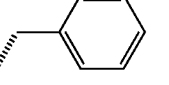 |
| 41 | (CH₂)₂CH₃ | CHO | 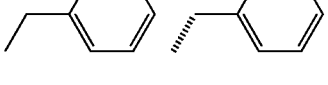 | 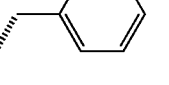 |
| 42 | (CH₂)₂CH₃ | ClCH₂ | | |

TABLE 1 (4)-continued
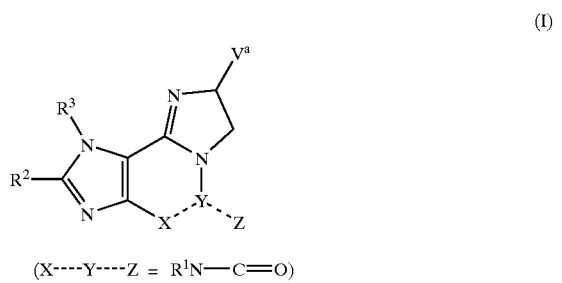
(X----Y----Z = R¹N—C=O)
| Compound No. | R¹ | R² | R³ | Vᵃ |
|---|---|---|---|---|
| 43 | (CH₂)₂CH₃ | (CH₃)₂NHCH₂ | H | benzyl |
| 44 | (CH₂)₂CH₃ | piperidin-1-ylmethyl | H | benzyl |
| 45 | (CH₂)₂CH₃ | CH₃CH₂OCH₂ | H | benzyl |
| 46 | (CH₂)₂CH₃ | (4,5-dimethyl-1,3-dioxolan-2-yl) | H | benzyl |
| 47 | (CH₂)₂CH₃ | CO₂CH₃ | benzyl | benzyl |
| 48 | (CH₂)₂CH₃ | HO—C(CH₃)₂— | benzyl | benzyl |
| 49 | (CH₂)₂CH₃ | piperidin-1-ylcarbonyl | H | benzyl |
| 50 | (CH₂)₂CH₃ | morpholin-4-ylcarbonyl | H | benzyl |

TABLE 1 (5)

(I)

(X----Y----Z = R¹N—C=O)

| Compound No. | R¹ | R² | R³ | Vᵃ |
|---|---|---|---|---|
| 51 | CH₃(CH₂)₂ | 2-methyltetrahydrofuran | H | benzyl |
| 52 | CH₃(CH₂)₂ | CH₃CH₂-O-CH(CH₃)₂ | H | benzyl |
| 53 | CH₃(CH₂)₂ | 4-methyltetrahydropyran | H | benzyl |
| 54 | CH₃(CH₂)₂ | trans-4-methyl-1-hydroxycyclohexyl | H | benzyl |
| 55 | CH₃(CH₂)₂ | 6-methyl-1,4-dioxaspiro[4.4]nonane | H | benzyl |
| 56 | CH₃(CH₂)₂ | PhCH₂-O-CH₂CH₃ | H | benzyl |
| 57 | CH₃(CH₂)₂ | 1-methoxy-1-phenylethyl | H | benzyl |
| 58 | CH₃(CH₂)₂ | H₃C-O-CH₂CH₂CH₂- | H | benzyl |
| 59 | CH₃(CH₂)₂ | HOOC-CH₂CH₂CH₂- | H | benzyl |

TABLE 1 (6)
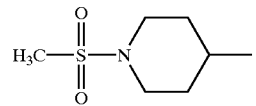
(X----Y----Z = R¹N—C=O)                                    (I)
| Compound No. | R¹ | R² | R³ | Vᵃ |
|---|---|---|---|---|
| 60 | CH₃(CH₂)₂ | 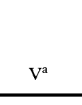 | H | C(CH₃)₃ |
| 61 | CH₃(CH₂)₂ | 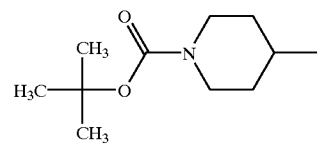 | H | 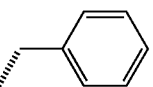 |
| 62 | CH₃(CH₂)₂ | 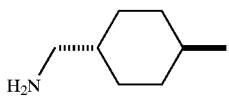 | H | 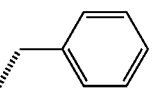 |
| 63 | CH₃(CH₂)₂ | 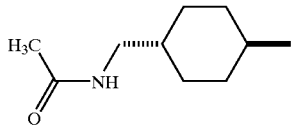 | H | 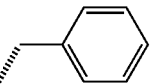 |
| 64 | CH₃(CH₂)₂ | CH₃CH₂SCH₂ | H | 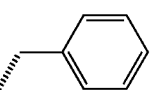 |
| 65 | CH₃(CH₂)₂ | 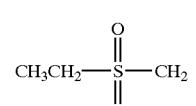 | H | 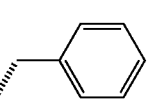 |
TABLE 1 (7)
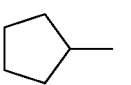
(X----Y----Z = N=C—W)                                       (I)
| Compound No. | W | R² | R³ | Vᵃ |
|---|---|---|---|---|
| 66 | Cl | 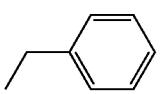 | 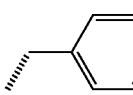 |  |

TABLE 1 (7)-continued

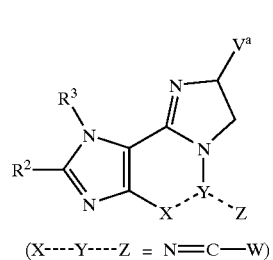

(X----Y----Z = N═C—W)

| Compound No. | W | R² | R³ | Vᵃ |
|---|---|---|---|---|
| 67 | CH₃NHCH₂CH₃ (methylaminoethyl) | cyclopentyl | H | benzyl |
| 68 | CH₃NH-CH₂CH₂-piperidinyl | cyclopentyl | H | benzyl |
| 69 | N-methylpyrrolidinyl | cyclopentyl | H | benzyl |
| 70 | CH₃OCH₂CH₃ | (CH₃)₃C | H | benzyl |
| 71 | CH₃O-CH₂CH₂CH₂-SCH₃ | cyclopentyl | H | benzyl |
| 72 | CH₃O-CH₂CH₂CH₂-S(O)₂CH₃ | cyclopentyl | H | benzyl |
| 73 | SCH₃ | (CH₃)₃C | H | benzyl |
| 74 | CH₂CH₃ | cyclopentyl | H | benzyl |
| 75 | C≡N | cyclopentyl | H | benzyl |
| 76 | 1H-tetrazol-5-yl | cyclopentyl | H | benzyl |

TABLE 1 (8)

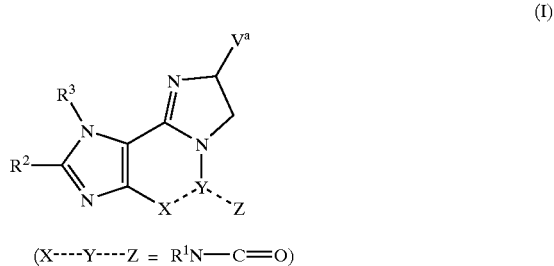

(X----Y----Z = R¹N—C=O)

| Compound No. | R¹ | R² | R³ | Vª |
|---|---|---|---|---|
| 77 | HO-C(=O)-CH2CH2- | cyclopentyl | H | benzyl |
| 78 | H3C-CH2-NH-C(=O)-CH2CH2- | cyclopentyl | H | benzyl |
| 79 | 2-oxo-oxazolidin-3-yl-butyl | cyclopentyl | H | benzyl |
| 80 | HO-CH2CH2CH2- | cyclopentyl | H | 4-fluorobenzyl |
| 81 | HO-C(CH3)2-CH2CH3 | cyclopentyl | H | benzyl |
| 82 | HO-CH2CH2CH2CH2- | cyclopentyl | H | benzyl |
| 83 | HO-CH2CH2CH2CH2- | (CH3)3C | H | benzyl |
| 84 | 2-methyl-1,3-dioxolan-2-yl-propyl | cyclopentyl | H | benzyl |
| 85 | (CH3)2C(OH)-CH2CH2CH3 | cyclopentyl | H | benzyl |
| 86 | (CH3)2C(OH)-CH2CH2CH3 | (CH3)3C | H | benzyl |

TABLE 1 (9)

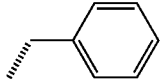

(X----Y----Z = R¹N—C=O)

| Compound No. | R¹ | R² | R³ | V¹ | V² |
|---|---|---|---|---|---|
| 87 | $CH_3(CH_2)_2$ | $CH_3CH_2OCH_2$ | H | 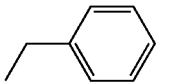 | H |
| 88 | $CH_3(CH_2)_2$ | $CH_3CH_2OCH_2$ | H | H | 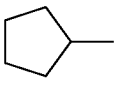 |
| 89 | $CH_3(CH_2)_2$ | 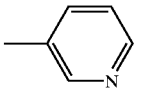 | H | H | (pyridyl) |

Compound (I) or a pharmacologically acceptable salt thereof has insulin secretion promoting action in cultured β-cells and hypoglycemic action in rats, and accordingly, the substance is useful as an active ingredient of a medicament for prophylactic and/or therapeutic treatment of diabetes. Further, the substance is also useful as an active ingredient of a medicament for prophylactic and/or therapeutic treatment of various complications of diabetes, for example, retinopathy, nephropathy, neurosis or the like. As the active ingredient of these medicaments, one or more substances selected from the group consisting of Compound (I) and pharmacologically acceptable salts thereof, and hydrates thereof and solvates thereof can be used. Although the aforementioned substance, per se, can also be administered, it is generally desirable to provide the medicament in a form of a pharmaceutical composition comprising the aforementioned substance as the active ingredient and one or more additives for pharmaceutical preparations. These medicaments can be administered to humans and mammals other than human.

The form of the pharmaceutical composition is not particularly limited, and an appropriate form most suitable for a purpose of therapeutic or prophylactic treatment can be selected from forms of pharmaceutical preparations for oral or parenteral administration. Examples of pharmaceutical preparations suitable for oral administration include, for example, tablets, powders, granules, syrups and the like. Example of pharmaceutical preparations suitable for parenteral administration include, for example, injections and the like. However, the preparations are not limited to these examples.

Liquid preparations suitable for oral administration such as syrups can be prepared by using water, saccharides such as sucrose, sorbitol, or fructose, glycols such as polyethylene glycol or propylene glycol, oils such as sesame oil, olive oil, or soybean oil, preservatives such as p-hydroxybenzoic acid esters, flavors such as strawberry flavor or peppermint or the like. For the preparation of solid preparations such as tablets, powders, and granules, excipients such as lactose, glucose, sucrose, or mannitol, disintegrating agents such as starch or sodium alginate, lubricants such as magnesium stearate or talc, binders such as polyvinyl alcohol, hydroxypropylcellulose, or gelatin, surface active agents such as fatty acid esters, plasticizers such as glycerin or the like may be used.

Pharmaceutical preparations for injection, which are suitable for parenteral administration, contain the aforementioned substance as the active ingredient preferably in a sterilized aqueous medium isotonic with blood of a recipient in a dissolved or suspended state. For example, as for injections, a solution can be prepared by using an aqueous medium consisting of saline, a glucose solution, a mixture of saline and a glucose solution or the like. To these pharmaceutical preparations for parenteral administration, one or more auxiliary ingredients selected from glycols, oils, flavors, preservatives, excipients, disintegrating agents, lubricants, binders, surface active agents, plasticizers and the like may also be, added.

Dose and frequency of administration of Compound (I) may preferably be increased or decreased depending on various factors such as type and severity of diseases, dosage form, conditions of patients such as age and body weight, and presence or absence of complications. In general, Compound (I) may preferably be administered in an amount of 1 to 1000 mg/kg per day for an adult dividedly as three or four times of administrations.

Although Compound (I) or a pharmacologically acceptable salt thereof is useful as an active ingredient of a medicament, for example, use of Compound (I) or a pharmacologically acceptable salt thereof is not limited to this particular purpose.

BEST MODE FOR CARRYING OUT THE INVENTION

The present invention will be more specifically explained with reference to the following examples. However, the scope of the present invention is not limited to the following examples.

REFERENCE EXAMPLE 1

(S)-N-Benzoyl-β-(4-pyridyl)-α-alanine methyl ester (Compound A1)

Methanol (8 mL) was cooled to −5° C., thionyl chloride (685 μL, 9.39 mmol, 5.0 equivalents) was dropwise added thereto and the mixture was stirred for 30 minutes. To the mixture was added (S)-N-(tert-butoxycarbonyl)-β-(4-pyridyl)-α-alanine (500 mg, 1.88 mmol), and the mixture was stirred at the same temperature for 2 hours, then warmed to room temperature and stirred for 12 hours. After the solvent was evaporated under reduced pressure, the resulting residue was dissolved in methylene chloride (15 mL) and to the mixture was added benzoyl chloride (240 μL, 1.88 mmol, 1.0 equivalent) and triethylamine (1.05 mL, 7.52 mmol, 4.0 equivalents). The reaction mixture was stirred for 45 minutes under ice cooling, then warmed to room temperature and stirred for further 4 hours. To the reaction mixture was further added benzoyl chloride (120 μL, 0.940 mmol, 0.5 equivalent), the mixture was stirred for 2 hours, then water (20 mL) was added to the mixture, and the mixture was extracted with methylene chloride. The resulting organic layer was washed with saturated aqueous sodium hydrogen carbonate and saturated aqueous sodium chloride and dried over anhydrous magnesium sulfate. After the solvent was evaporated, the resulting residue was purified by silica gel column chromatography (chloroform:methanol=100:0 to 98:2) to obtain the title compound (520 mg, 97%).

$^1$H-NMR (270 MHz, CDCl$_3$) δ 3.17 (dd, 1H, J=14.0, 6.8 Hz), 3.30 (dd, 1H, J=14.0, 5.8 Hz), 3.72 (s, 3H), 5.09 (m, 1H), 5.15 (brs, 1H), 7.11 (d, 2H, J=5.9 Hz), 7.32–7.52 (m, 3H), 7.74 (d, 2H, J=7.3 Hz), 8.42 (d, 2H, J=5.9 Hz).

REFERENCE EXAMPLE 2

(S)-2-(N-Benzoylamino)-3-(4-pyridyl)-1-propanol (Compound A2)

Compound A1 (870 mg, 3.06 mmol) obtained in Reference Example 1 was dissolved in ethanol (8 mL) and water (8 mL). To the solution was added sodium borohydride (289 mg, 7.65 mmol, 2.5 equivalents), and the mixture was stirred for 2 hours under ice cooling. The reaction mixture was warmed to room temperature, then stirred for 24 hours and adjusted to pH 7 with 4 mol/L hydrochloric acid. The reaction mixture was concentrated to an about half volume and then extracted with chloroform, and the resulting organic layer was dried over anhydrous magnesium sulfate. The solvent was evaporated to obtain the title compound (550 mg, 70%).

$^1$H-NMR (270 MHz, CDCl$_3$) δ 3.02 (dd, 2H, J=7.4, 1.8 Hz), 3.67 (dd, 1H, J=11.2, 4.3 Hz), 3.77 (dd, 1H, J=11.2, 3.8 Hz), 4.41 (m, 1H), 6.67 (brd, 1H, J=7.9 Hz), 7.22 (d, 2H, J=4.4 Hz), 7.36–7.52 (m, 3H), 7.67–7.71 (m, 2H), 8.47 (d, 2H, J=4.4 Hz).

REFERENCE EXAMPLE 3

(S)-2-Amino-3-(4-pyridyl)-1-propanol (Compound A3)

To Compound A2 (550 mg, 2.15 mmol) obtained in Reference Example 2 was added concentrated hydrochloric acid (10 mL), and the mixture was stirred with heating for 7 hours. After the reaction mixture was cooled and the deposited solid was removed by filtration, the filtrate was concentrated under reduced pressure. The resulting oil was dissolved in methanol (20 mL) and water (1 mL), and to the solution was added BioRad AG-X8 (hydroxide form) until the solution became alkaline. After the resin was removed by filtration, the filtrate was concentrated under reduced pressure to obtain the title compound (310 mg, 95%).

$^1$H-NMR (270 MHz, CDCl$_3$) δ 2.55 (dd, 1H, J=13.5, 8.6 Hz), 2.81 (dd, 1H, J=13.5, 5.3 Hz), 3.17 (m, 1H), 3.41 (dd, 1H, J=10.6, 6.9 Hz), 3.63 (dd, 1H, J=10.6, 4.0 Hz), 7.15 (d, 2H, J=5.6 Hz), 8.52 (d, 2H, J=5.6 Hz).

REFERENCE EXAMPLE 4

2-Amino-3-(2-pyridyl)-1-propanol (Compound A5)

The title compound was obtained in a manner similar to that in Reference Examples 1 to 3 by using N-(tert-butoxycarbonyl)-β-(2-pyridyl)-α-alanine as a starting material, which was derived from β-(2-pyridyl)-α-alanine obtained by the method described in Bulletin Chemical Society Japan (Bull. Chem. Soc. Japan), 41, p. 1634, 1968.

$^1$H-NMR (270 MHz, CDCl$_3$) δ 2.79 (dd, 1H, J=13.5, 7.6 Hz), 2.97 (dd, 1H, J=13.5, 5.6 Hz), 3.26 (m, 1H), 3.45 (m, 1H), 3.57 (dd, 1H, J=11.2, 4.3 Hz), 7.17–7.25 (m, 2H), 7.68 (dt, 1H, J=7.6, 2.0 Hz), 8.50 (d, 1H, J=5.0 Hz).

FAB-MS: m/z 153 (M$^+$+1).

REFERENCE EXAMPLE 5

2-Amino-3-(3-pyridyl)-1-propanol (Compound A6)

The title compound was obtained in a manner similar to that in Reference Examples 1 to 3 by using N-(tert-butoxycarbonyl)-β-(3-pyridyl)-α-alanine as a starting material, which was derived from β-(3-pyridyl)-α-alanine obtained by the method described in Journal of Organic Chemistry (J. Org. Chem.), 29, p. 2658, 1964.

$^1$H-NMR (270 MHz, CDCl$_3$) δ 2.55 (dd, 1H, J=13.5, 8.3 Hz), 2.81 (dd, 1H, J=13.5, 5.3 Hz), 3.09 (m, 1H), 3.40 (m, 1H), 3.57 (dd, 1H, J=10.6, 4.3 Hz), 7.26 (dd, 1H, J=7.9, 5.0 Hz), 7.58 (d, 1H, J=7.9 Hz), 8.45–8.47 (m, 2H).

FAB-MS: m/z 153 (M$^+$+1).

REFERENCE EXAMPLE 6

2-Amino-3-(2-methylthiazol-4-yl)-1-propanol (Compound A7)

The title compound was obtained in a manner similar to that in Reference Examples 1 to 3 by using N-(tert-butoxycarbonyl)-β-(2-methylthiazol-4-yl)-α-alanine as a starting material, which was derived from β-(2-methylthiazol-4-yl)-α-alanine obtained by the method described in Synthesis, p. 1145, 1992.

$^1$H-NMR (270 MHz, CDCl$_3$) δ 2.69 (s, 3H), 2.77 (dd, 1H, J=13.9, 7.6 Hz), 2.88 (dd, 1H, J=13.9, 5.4 Hz), 3.25 (m, 1H), 3.46 (dd, 1H, J=10.9, 5.9 Hz), 3.57 (dd, 1H, J=10.9, 4.6 Hz), 6.82 (s, 1H).

FAB-MS: m/z 173 (M$^+$+1).

REFERENCE EXAMPLE 7

2-Amino-3-(2-pyrazinyl)-1-propanol (Compound A8)

The title compound was obtained in a manner similar to that in Reference Examples 1 to 3 by using N-(tert-butoxycarbonyl)-β-(2-pyrazinyl)-α-alanine as a starting material, which was derived from β-(2-pyrazinyl)-α-alanine obtained by the method described in Journal of Heterocyclic Chemistry (J. Heterocycl. Chem.), 2, p. 1, 1965.

$^1$H-NMR (270 MHz, CDCl$_3$) δ 2.84 (dd, 1H, J=13.8, 4.9 Hz), 2.99 (dd, 1H, J=13.8, 5.4 Hz), 3.36 (m, 1H), 3.46 (m, 1H), 3.62 (dd, 1H, J=10.8, 4.1 Hz), 8.45–8.55 (m, 3H).

FAB-MS: m/z 154 (M$^+$+1).

REFERENCE EXAMPLE 8

2-Amino-3-(4-pyrimidinyl)-1-propanol (Compound A9)

The title compound was obtained in a manner similar to that in Reference Examples 1 to 3 by using N-(tert-butoxycarbonyl)-β-(4-pyrimidinyl)-α-alanine as a starting material, which was derived from β-(4-pyrimidinyl)-α-alanine obtained by the method described in Journal of Heterocyclic Chemistry (J. Heterocycl. Chem.), 2, p. 1, 1965.

$^1$H-NMR (270 MHz, CDCl$_3$) δ 2.80 (dd, 1H, J=13.8, 7.8 Hz), 2.95 (dd, 1H, J=13.8, 4.6 Hz), 3.38 (m, 1H), 3.48 (m, 1H), 3.61 (dd, 1H, J=10.5, 4.3 Hz), 7.23 (d, 1H, J=5.4 Hz), 8.64 (d, 1H, J=5.4 Hz), 9.14 (s, 1H).

FAB-MS: m/z 154 (M$^+$+1).

REFERENCE EXAMPLE 9

2-Amino-3-(4-pyridyl)-1-propanol (Compound A10)

The title compound was obtained in a manner similar to that in Reference Examples 1 to 3 by using N-(tert-butoxycarbonyl)-β-(4-pyridyl)-α-alanine as a starting material, which was derived from β-(4-pyridyl)-α-alanine obtained by the method described in Journal of Organic Chemistry (J. Org. Chem.), 23, p. 575, 1958.

$^1$H-NMR (270 MHz, CDCl$_3$) δ 2.55 (dd, 1H, J=13.2, 8.6 Hz), 2.81 (dd, 1H, J=13.2, 5.3 Hz), 3.15 (m, 1H), 3.40 (dd, 1H, J=10.6, 6.9 Hz), 3.47 (s, 1H), 3.62 (dd, 1H, J=10.6, 4.0 Hz), 7.16 (d, 2H, J=5.9 Hz), 8.53 (d, 2H, J=5.9 Hz).

FAB-MS: m/z 153 (M$^+$+1).

REFERENCE EXAMPLE 10

(R)-2-Amino-3-(4-fluorophenyl)-1-propanol (Compound A11)

The title compound was obtained in a manner similar to that in Reference Examples 1 to 3 by using (R)-N-(tert-butoxycarbonyl)-4-fluorophenylalanine as a starting material, which was derived from (R)-4-fluorophenylalanine.

$^1$H-NMR (270 MHz, CDCl$_3$) δ 2.51 (dd, 1H, J=13.5, 8.5 Hz), 2.77 (dd, 1H, J=13.5, 5.3 Hz), 3.09 (m, 1H), 3.37 (dd, 1H, J=10.5, 6.9 Hz), 3.62 (dd, 1H, J=10.5, 4.0 Hz), 6.96–7.06 (m, 2H), 7.12–7.22 (m, 2H).

REFERENCE EXAMPLE 11

(R)-3-Amino-4-phenyl-1-butanol (Compound A12)

To a solution (70 mL) of lithium aluminum hydride (1.50 g, 39.5 mmol, 3.0 equivalents) in tetrahydrofuran was added dropwise a solution of (R)-N-(benzoyloxy-carbonyl)-3-amino-4-phenylbutanoic acid (4.84 g, 13.1 mmol), which was obtained by the method described in Tetrahedron, 44, p. 5525, 1988 and Journal of Organic Chemistry (J. Org. Chem.), 64, p. 6411, 1999, in tetrahydrofuran (30 mL) under ice cooling, and the mixture was stirred at room temperature for 30 minutes. After the reaction solution was cooled on ice, excess lithium aluminum hydride was decomposed with ethyl acetate and water. The deposited solid was removed by filtration using a filtration aid, and the filtrate was extracted with chloroform. The organic layer was washed with saturated aqueous sodium chloride and dried over anhydrous sodium sulfate, and the solvent was evaporated. After the resulting residue was purified by silica gel column chromatography (ethyl acetate:n-hexane=50:50), the resulting (R)-N-(benzyloxycarbonyl)-3-amino-4-phenyl-1-butanol (1.37 g, 5.09 mmol) was dissolved in methanol (30 mL), and to the solution were added 20% palladium hydroxide/carbon (200 mg) and ammonium formate (1.30 g, 20.6 mmol, 4.1 equivalents), and then the mixture was stirred for 1 hour with heating. After the catalyst was removed by using a filtration aid, the solvent was evaporated. To the residue was added ethyl acetate, and the deposited solid was collected by filtration to obtain the title compound (730 mg, 87%).

$^1$H-NMR (270 MHz, DMSO-d$_6$) δ 1.61 (q, 2H, J=6.3 Hz), 2.77 (dd, 1H, J=13.5, 8.4 Hz), 3.00 (dd, 1H, J=13.5, 5.7 Hz), 3.41 (m, 1H), 3.49 (dt, 2H, J=10.8, 4.6 Hz), 7.22–7.36 (m, 5H).

REFERENCE EXAMPLE 12

3-Amino-2-benzyl-1-propanol (Compound A13)

The title compound (1.29 g, 59%) was obtained by the method described in Journal of Organic Chemistry (J. Org. Chem.), 43, p. 2539, 1978 using 2-benzyl-3-oxopropionic acid ethyl ester (2.73 g, 13.3 mmol) as a starting material, which was obtained by the method described in Tetrahedron, 38, p. 3597, 1982.

$^1$H-NMR (270 MHz, CDCl$_3$) δ 1.99 (m, 1H), 2.48 (dd, 1H, J=13.6, 7.3 Hz), 2.59 (dd, 1H, J=13.6, 7.3 Hz), 2.75 (dd, 1H, J=12.2, 8.6 Hz), 3.07 (ddd, 1H, J=12.2, 3.6, 1.3 Hz), 3.66 (dd, 1H, J=10.6, 7.6 Hz), 3.81 (ddd, 1H, J=10.6, 3.3, 1.3 Hz), 7.15–7.31 (m, 5H).

REFERENCE EXAMPLE 13

3-Amino-2-(3-pyridyl)-1-propanol (Compound A14)

The title compound (1.17 g, 39%) was obtained by the method described in Journal of Organic Chemistry (J. Org. Chem.), 43, p. 2539, 1978 using 3-pyridylacetic acid ethyl ester (2.50 g, 15.1 mmol) as a starting material, which was obtained by the method described in Journal of Organic Chemistry (J. Org. Chem.), 43, 2539, 1978.

$^1$H-NMR (270 MHz, DMSO-d$_6$) δ 2.71 (dt, 2H, J=13.5, 7.0 Hz), 2.89 (quin, 1H, J=5.1 Hz), 3.58 (dd, 1H, J=10.5, 6.2 Hz), 3.67 (dd, 1H, J=10.5, 6.2 Hz), 7.29 (dd, 1H, J=7.8, 5.4 Hz), 7.61 (dt, 1H, J=5.4, 2.2 Hz), 8.37–8.41 (m, 2H).

REFERENCE EXAMPLE 14

6-Methylthio-3,8-dipropyl-7H-purin-2(3H)-one (Compound B2)

3,8-Dipropylxanthine (12.3 g, 52.2 mmol), which was obtained by the method described in Journal of Medicinal Chemistry (J. Med. Chem.), 16 (35), p. 3066, 1992, was dissolved in pyridine (185 mL). To the solution was added phosphorus pentasulfide (16.4 g, 73.7 mmol, 1.4 equivalents), and the mixture was stirred with heating at 130° C. for 5 hours. After the reaction solution was poured into ice water and the mixture was extracted with chloroform, the organic layer was washed with saturated aqueous sodium chloride and dried over anhydrous sodium sulfate, and the solvent was evaporated. The residue was purified by silica gel column chromatography (chloroform:methanol=95:5) to obtain a thione compound (8.80 g, 67%). The thione compound (8.80 g, 34.7 mmol) was dissolved in a mixture of 0.5 mol/L aqueous sodium hydroxide (120 mL) and ethanol (40 mL) and the mixture was stirred at room temperature for 30 minutes. To the reaction mixture was added methyl iodide (4.00 mL, 64.2 mmol, 1.9 equivalents), and the mixture was stirred at room temperature for 1 hour. The reaction solution was neutralized with 2 mol/L aqueous hydrochloric acid, and the deposited crystals were collected by filtration to obtain the title compound (7.40 g, 80%).

$^1$H-NMR (270 MHz, CDCl$_3$) δ 0.98 (t, 3H, J=7.3 Hz), 1.02 (t, 3H, J=7.3 Hz), 1.85 (m, 4H), 2.50 (s, 3H), 2.89 (t, 2H, J=7.3 Hz), 4.22 (t, 2H, J=7.6 Hz), 13.9 (brs, 1H).

REFERENCE EXAMPLE 15

8-Cyclohexyl-6-methylthio-3-(n-propyl)-7H-purin-2(3H)-one (Compound B3)

Phosphorus pentasulfide (27.1 g, 122 mmol, 1.5 equivalents) was suspended in pyridine (150 mL) and the mixture was heated to 100° C. To the suspension was gradually added 5,6-diamino-1-propyluracil (15.0 g, 81.3 mmol), which was obtained by the method described in Journal of Medicinal Chemistry (J. Med. Chem.), 32 (6), p. 1231, 1989, with heating and stirring, and then the mixture was stirred for 7 hours. After the reaction solution was cooled on ice, the deposited solid was separated by filtration using a filtration aid and washed with pyridine. The filtrate was concentrated, to the residue was added water (90 mL), and the mixture was stirred under reflux with heating for about 40 minutes until intense foaming ceased. The reaction mixture was cooled on ice and then further stirred overnight at room temperature. The deposited yellowish green ocher solid was collected by filtration, sufficiently washed with water and dried under reduced pressure to obtain 5,6-diamino-1,2-dihydro-4-mercapto-2-oxo-1-propylpyrimidine (Compound B4, 11.3 g, 69%). Compound B4 (10.0 g, 50.0 mmol) was suspended in 1,4-dioxane (200 mL) and water (100 mL), to the suspension were added cyclohexanecarboxylic acid (8.06 mL, 65.0 mmol, 1.3 equivalents) and 1-ethyl-3-(3-dimethylaminopropyl)carbodiimide hydrochloride (16.3 g, 85.0 mmol, 1.7 equivalents) at room temperature, and then the mixture was stirred overnight. To the reaction mixture was added 2 mol/L aqueous sodium hydroxide (100 mL), and the mixture was stirred with heating for 2.5 hours. The reaction mixture was cooled on an ice bath, adjusted to pH 6 with 4 mol/L hydrochloric acid and extracted with chloroform. The organic layer was dried over anhydrous magnesium sulfate, and the solvent was evaporated. The residue was dissolved in 0.5 mol/L aqueous sodium hydroxide (150 mL), and to the solution was added methyl iodide (4.70 mL, 75.0 mmol, 1.5 equivalents) and the mixture was stirred overnight at room temperature. The reaction mixture was cooled on an ice bath, adjusted to pH 6.5 with 4 mol/L aqueous hydrochloric acid and extracted with chloroform. The organic layer was dried over anhydrous magnesium sulfate, and the solvent was evaporated. Then, the residue was purified by silica gel column chromatography (chloroform:methanol=100:0 to 96:4) to obtain the title compound (11.8 g, 78%).

$^1$H-NMR (270 MHz, CDCl$_3$) δ 0.98 (t, 3H, J=7.3 Hz), 1.85–2.11 (m, 8H), 2.32 (s, 3H), 2.33–2.62 (m, 4H), 3.77 (m, 1H), 4.16 (t, 2H, J=7.6 Hz).

REFERENCE EXAMPLE 16

8-Cyclobutyl-6-methylthio-3-(n-propyl)-7H-purin-2(3H)-one (Compound B5)

8-Cyclobutyl-3-(n-propyl)-6-thioxanthine (1.00 g, 3.79 mmol), which was obtained by the method described in EP 256692A, was dissolved in 0.5 mol/L aqueous sodium hydroxide (15 mL), and the solution was stirred at room temperature for 30 minutes. To the reaction mixture was added methyl iodide (350 μL, 5.71 mmol, 1.5 equivalents), and the mixture was stirred at room temperature for 18 hours. The reaction solution was neutralized with 4 mol/L aqueous hydrochloric acid, and the deposited crystals were collected by filtration to obtain the title compound (910 mg, 86%).

$^1$H-NMR (270 MHz, CDCl$_3$) δ 0.98 (t, 3H, J=7.3 Hz), 1.85–2.11 (m, 4H), 2.08 (s, 3H), 2.33–2.62 (m, 4H), 3.76 (m, 1H), 4.25 (t, 2H, J=7.4 Hz).

REFERENCE EXAMPLE 17

8-(tert-Butyl)-6-methylthio-3-(n-propyl)-7H-purin-2(3H)-one (Compound B6)

Compound B4 (7.00 g, 35.2 mmol) was dissolved in pyridine (70 mL). To the solution was added pivaloyl chloride (4.74 mL, 38.5 mmol, 1.1 equivalents), and the mixture was stirred at room temperature for 18 hours. The reaction mixture was concentrated, to the residue was added 2 mol/L aqueous sodium hydroxide (100 mL), and the mixture was stirred with heating for 2 hours. The reaction mixture was adjusted to pH 6.5 with 4 mol/L aqueous hydrochloric acid under ice cooling and extracted with chloroform. After the organic layer was dried over anhydrous magnesium sulfate and the solvent was evaporated, water was added to the residue. The deposited solid was collected by filtration and dried under reduced pressure to obtain a thione compound (9.21 g, 99%). Then, the title compound (9.65 g, 100%) was obtained in a manner similar to that in Reference Example 16.

$^1$H-NMR (270 MHz, CDCl$_3$) δ 0.96 (t, 3H, J=7.5 Hz), 1.46 (s, 9H), 1.83–1.91 (m, 2H), 2.12 (s, 3H), 4.24 (t, 2H, J=7.3 Hz), 12.3 (brs, 1H).

REFERENCE EXAMPLE 18

8-(1-Methylcyclohexyl)-6-methylthio-3-(n-propyl)-7H-purin-2(3H)-one (Compound B7)

The title compound (1.73 g, 54%) was obtained from Compound B4 (2.00 g, 10.0 mmol) and 1-methylcyclohexanecarbonyl chloride (2.27 g, 14.1 mmol, 1.4 equivalents) in a manner similar to that in Reference Example 17.

$^1$H-NMR (270 MHz, CDCl$_3$) δ 0.95 (t, 3H, J=7.4 Hz), 1.35 (s, 3H), 1.44–1.61 (m, 8H), 1.82–1.90 (m, 2H), 2.18–2.26 (m, 2H), 2.26 (s, 3H), 4.23 (t, 2H, J=7.1 Hz), 11.4 (brs, 1H).

REFERENCE EXAMPLE 19

8-Cyclopentyl-3-cyclopropylmethyl-6-methylthio-7H-purin-2(3H)-one (Compound B9)

5,6-Diamino-1-cyclopropylmethyluracil (3.00 g, 15.3 mmol), which was obtained by the method described in EP386683A, was suspended in a mixed solvent of 1,4-dioxane (50 mL) and water (25 mL). To the suspension were added cyclopentanecarboxylic acid (2.16 mL, 19.9 mmol, 1.3 equivalents) and 1-ethyl-3-(3-dimethylaminopropyl)carbodiimide hydrochloride (5.00 g, 26.0 mmol, 1.7 equivalents), and the mixture was stirred overnight at room temperature. To the reaction mixture was added 2 mol/L aqueous sodium hydroxide (20 mL), and the mixture was refluxed with heating for 5 hours. The reaction solution was cooled on ice, and adjusted to pH 6.5 with addition of 4 mol/L aqueous hydrochloric acid. The deposited solid was collected by filtration, washed with water and diisopropyl alcohol and dried under reduced pressure to obtain a xanthine compound. Phosphorus pentasulfide (2.53 g, 11.4 mmol) was dissolved in pyridine (33 mL), to the solution was added the xanthine compound, and then the mixture was stirred at 100° C. for 4 hours. After the solvent was evaporated under reduced pressure, ice was added to the resulting residue to triturate the solid, and the solid was collected by filtration and dried under reduced pressure to obtain a thione compound. The thione compound was dissolved in 0.5 mol/L aqueous sodium hydroxide (50 mL), to the solution was added methyl iodide (1.04 mL, 16.7 mmol) under ice cooling, and the mixture was stirred at room temperature for 18 hours. The reaction mixture was adjusted to pH 6.5 with 4 mol/L aqueous hydrochloric acid and then extracted with chloroform. After the resulting organic layer was dried over anhydrous magnesium sulfate, the solvent was evaporated under reduced pressure, and the residue was purified by silica gel column chromatography (chloroform:methanol=100:0 to 98:2) to obtain the title compound (1.66 g, 37%).

$^1$H-NMR (270 MHz, CDCl$_3$) δ 0.44–0.57 (m, 4H), 1.26–2.17 (m, 9H), 2.00 (s, 3H), 3.31 (quin, 1H, J=8.2 Hz), 4.17 (d, 2H, J=7.3 Hz), 13.6 (brs, 1H).

REFERENCE EXAMPLE 20

8-(tert-Butyl)-3-cyclopropylmethyl-6-methylthio-7H-purin-2(3H)-one (Compound B10)

5,6-Diamino-1-cyclopropylmethyluracil (3.00 g, 15.3 mmol), which was obtained by the method described in EP386683A, was dissolved in pyridine (60 mL), to the solution was added pivaloyl chloride (2.07 mL, 16.8 mmol, 1.1 equivalents), and the mixture was stirred at room temperature for 18 hours. The reaction solution was concentrated under reduced pressure, to the concentrate was added 2 mol/L aqueous sodium hydroxide (20 mL), and the mixture was stirred with heating for 4 hours. The reaction mixture was adjusted to pH 6.5 with 4 mol/L aqueous hydrochloric acid under ice cooling, and the deposited solid were collected by filtration, washed with water and dried under reduced pressure to obtain a xanthine compound. Then, the title compound (3.28 g, 73%) was obtained in a manner similar to that in Reference Example 16.

$^1$H-NMR (270 MHz, DMSO-d$_6$) δ 0.42–0.44 (m, 4H), 1.31 (m, 1H), 1.37 (s, 9H), 2.51 (s, 3H), 3.90 (d, 2H, J=6.9 Hz), 12.8 (brs, 1H).

REFERENCE EXAMPLE 21

8-Cyclopentyl-3-ethyl-6-methylthio-7H-purin-2(3H)-one (Compound B11)

In a manner similar to that in Reference Example 15, the title compound (3.49 g, 81%) was obtained from 5,6-diamino-1-ethyl-1,2-dihydro-4-mercapto-2-oxopyrimidine (5.85 g, 31.5 mmol), which was synthesized from 5,6-diamino-1-ethyluracil obtained by the method described in U.S. Pat. No. 4,338,319.

$^1$H-NMR (270 MHz, DMSO-d$_6$) δ 1.21 (t, 3H, J=6.9 Hz), 1.55–2.09 (m, 8H), 2.56 (s, 3H), 3.19 (quin, 1H, J=8.2 Hz), 4.04 (q, 2H, J=7.0 Hz).

REFERENCE EXAMPLE 22

8-Ethoxymethyl-6-methylthio-3-(n-propyl)-7H-purin-2(3H)-one (Compound B12)

The title compound was obtained from Compound B4 and ethoxy acetic acid in a manner similar to that in Reference Example 15.

$^1$H-NMR (270 MHz, CDCl$_3$) δ 0.97 (t, 3H, J=7.3 Hz), 1.29 (t, 3H, J=6.9 Hz), 1.85 (q, 2H, J=7.3 Hz), 2.61 (s, 3H), 3.69 (q, 2H, J=6.9 Hz), 4.17 (t, 2H, J=7.3 Hz), 4.71 (s, 2H), 10.6 (br, 1H).

REFERENCE EXAMPLE 23

6-Methylthio-3-(n-propyl)-2-(tetrahydrofuran-2-yl)-7H-purin-2(3H)-one (Compound B13)

The title compound was obtained from Compound B4 and 2-tetrahydrofurancarboxylic acid in a manner similar to that in Reference Example 15.

$^1$H-NMR (270 MHz, CDCl$_3$) δ 0.97 (t, 3H, J=7.4 Hz), 1.78–1.91 (m, 2H), 1.94–2.08 (m, 2H), 2.24 (m, 1H), 2.45 (m, 1H), 2.53 (s, 3H), 3.96 (m, 1H), 4.07–4.20 (m, 3H), 5.16 (dd, 1H, J=7.7, 5.8 Hz), 11.1 (brs, 1H).

REFERENCE EXAMPLE 24

8-(1-Ethoxymethyl)-6-methylthio-3-(n-propyl)-7H-purin-2(3H)-one (Compound B14)

To an ethanol solution of sodium ethoxide, which was prepared by adding metallic sodium to anhydrous ethanol, was added 2-bromopropionic acid, and the mixture was stirred with heating for 90 minutes. After the ethanol was evaporated, a saturated ammonium chloride solution was added to the residue and the mixture was extracted with chloroform. The organic layer was dried over anhydrous sodium sulfate, and the solvent was evaporated. The resulting residue was condensed with Compound B4 in a manner similar to that in Reference Example 15 to obtain the title compound.

$^1$H-NMR (270 MHz, CDCl$_3$) δ 0.98 (t, 3H, J=7.3 Hz), 1.29 (t, 3H, J=7.0 Hz), 1.58 (d, 3H, J=6.6 Hz), 1.85 (q, 2H,

J=7.3 Hz), 2.66 (s, 3H), 3.57 (m, 1H), 3.66 (m, 1H), 4.17 (t, 2H, J=7.3 Hz), 4.72 (q, 1H, J=6.6 Hz), 9.96 (brs, 1H).

REFERENCE EXAMPLE 25

6-Methylthio-3-(n-propyl)-2-(tetrahydropyran-4-yl)-7H-purin-2(3H)-one (Compound B15)

In a manner similar to that in Reference Example 15, the title compound was obtained from Compound B4 and 4-tetrahydropyrancarboxylic acid, which was obtained by the method described in Hervetica Chemica Acta (Helv. Chem. Acta), 80, p. 1528, 1997.
$^1$H-NMR (270 MHz, CDCl$_3$) δ 0.97 (t, 3H, J=7.4 Hz), 1.81–1.90 (m, 2H), 1.98–2.15 (m, 4H), 2.04 (s, 3H), 3.20 (m, 1H), 3.52 (dt, 2H, J=11.8, 3.0 Hz), 4.02–4.14 (m, 2H), 4.26 (t, 2H, J=7.3 Hz).

REFERENCE EXAMPLE 26

6-Methylthio-8-(4-oxocyclohexyl)-3-(n-propyl)-7H-purin-2(3H)-one (Compound B16)

In a manner similar to that in Reference Example 15, the title compound was obtained from Compound B4 and 4-oxocyclohexanecarboxylic acid, which was derived from 4-oxocyclohexanecarboxylic acid ethyl ester.
$^1$H-NMR (270 MHz, CDCl$_3$) δ 0.97 (t, 3H, J=7.3 Hz), 1.83–2.60 (m, 10H), 2.12 (s, 3H), 3.48 (m, 1H), 4.25 (t, 2H, J=7.3 Hz).

REFERENCE EXAMPLE 27

8-(1,3-Dioxolane-2-spirocyclopentan-2'-yl)-6-methylthio-3-(n-propyl)-7H-purin-2(3H)-one (Compound B17)

In a manner similar to that in Reference Example 15, the title compound was obtained from Compound B4 and 1,3-dioxolane-2-spirocyclopentane, which was derived from 2-oxocyclopentanecarboxylic acid.
$^1$H-NMR (270 MHz, CDCl$_3$) δ 0.97 (t, 3H, J=7.4 Hz), 1.73–2.04 (m, 8H), 2.39 (s, 3H), 3.51 (t, 1H, J=8.6 Hz), 3.75–3.94 (m, 4H), 4.22 (t, 2H, J=7.3 Hz).

REFERENCE EXAMPLE 28

8-Benzyloxymethyl-6-methylthio-3-(n-propyl)-7H-purin-2(3H)-one (Compound B18)

The title compound was obtained from Compound B4 and benzyloxyacetic acid in a manner similar to that in Reference Example 15.
$^1$H-NMR (270 MHz, CDCl$_3$) δ 0.97 (t, 3H, J=7.4 Hz), 1.83 (q, 2H, J=7.4 Hz), 2.57 (s, 3H), 4.15 (t, 2H, J=7.3 Hz), 4.69 (s, 2H), 4.76 (s, 2H), 7.32–7.38 (m, 5H), 10.9 (brs, 1H).

REFERENCE EXAMPLE 29

8-(α-Methoxybenzyl)-6-methylthio-3-(n-propyl)-7H-purin-2(3H)-one (Compound B19)

The title compound was obtained from Compound B4 and α-methoxyphenylacetic acid in a manner similar to that in Reference Example 15.
$^1$H-NMR (270 MHz, CDCl$_3$) δ 0.93 (t, 3H, J=7.3 Hz), 1.83 (q, 2H, J=7.3 Hz), 2.20 (s, 3H), 3.44 (s, 3H), 4.19 (t, 2H, J=7.3 Hz), 5.52 (s, 1H), 7.21–7.30 (m, 3H), 7.42–7.47 (m, 2H).

REFERENCE EXAMPLE 30

8-(2-Methoxyethyl)-6-methylthio-3-(n-propyl)-7H-purin-2(3H)-one (Compound B20)

The title compound was obtained from Compound B4 and 3-methoxypropionic acid in a manner similar to that in Reference Example 15.
$^1$H-NMR (270 MHz, CDCl$_3$) δ 0.98 (t, 3H, J=7.4 Hz), 1.78–1.92 (m, 2H), 2.56 (s, 3H), 3.14 (t, 2H, J=5.9 Hz), 3.44 (s, 3H), 3.79 (t, 2H, J=5.9 Hz), 4.15–4.20 (m, 2H), 10.9 (brs, 1H).

REFERENCE EXAMPLE 31

8-(2-Carboxyethyl)-6-methylthio-3-(n-propyl)-7H-purin-2(3H)-one (Compound B21)

The title compound was obtained from Compound B4 and succinic acid monoethyl ester in a manner similar to that in Reference Example 15.
$^1$H-NMR (270 MHz, DMSO-d$_6$) δ 0.87 (t, 3H, J=7.6 Hz), 1.63–1.71 (m, 2H), 2.56 (s, 3H), 2.74 (t, 2H, J=6.9 Hz), 2.97 (t, 2H, J=6.9 Hz), 3.96 (t, 2H, J=7.3 Hz).

REFERENCE EXAMPLE 32

8-(1-Methylsulfonylpiperidin-4-yl)-6-methylthio-3-(n-propyl)-7H-purin-2(3H)-one (Compound B22)

In a manner similar to that in Reference Example 15, the title compound was obtained from Compound B4 and N-methylsulfonylisonipecotinic acid, which was derived from isonipecotinic acid.
$^1$H-NMR (270 MHz, DMSO-d$_6$) δ 0.88 (t, 3H, J=7.2 Hz), 1.65–1.91 (m, 4H), 1.97–2.09 (m, 2H), 2.57 (s, 3H), 2.89 (s, 3H), 2.90–3.01 (m, 3H), 3.57–3.66 (m, 2H), 3.84–4.01 (m, 2H), 13.1 (brs, 1H).

REFERENCE EXAMPLE 33

2-[1-(tert-Butoxycarbonyl)piperidin-4-yl]-6-methylthio-3-(n-propyl)-7H-purin-2(3H)-one (Compound B23)

In a manner similar to that in Reference Example 15, the title compound was obtained from Compound B4 and N-(tert-butoxycarbonyl)isonipecotinic acid, which was derived from isonipecotinic acid.
$^1$H-NMR (270 MHz, CDCl$_3$) δ 0.97 (t, 3H, J=7.4 Hz), 1.46 (s, 9H), 1.83–2.04 (m, 6H), 2.09 (s, 3H), 2.83–2.92 (m, 2H), 3.14 (m, 1H), 4.14–4.27 (m, 4H).

REFERENCE EXAMPLE 34

8-[trans-4-(Benzyloxycarbonylaminomethyl)cyclohexyl]-6-methylthio-3-(n-propyl)-7H-purin-2(3H)-one (Compound B24)

In a manner similar to that in Reference Example 15, the title compound was obtained from Compound B4 and trans- 4-(benzyloxycarbonylaminomethyl)-cyclohexanecarboxylic acid, which was derived from trans-4-(aminomethyl)-cyclohexanecarboxylic acid.

$^1$H-NMR (270 MHz, CDCl$_3$) δ 0.95 (t, 3H, J=7.4 Hz), 1.04–1.12 (m, 4H), 1.43–1.99 (m, 7H), 2.11 (s, 3H), 2.85 (m, 1H), 3.05–3.15 (m, 2H), 4.16–4.24 (m, 2H), 4.86 (m, 1H), 5.09 (s, 2H), 7.30–7.36 (m, 5H).

REFERENCE EXAMPLE 35

8-Ethylthiomethyl-6-methylthio-3-(n-propyl)-7H-purin-2(3H)-one (Compound B25)

The title compound was obtained from Compound B4 and ethyl thioacetate in a manner similar to that in Reference Example 15.

$^1$H-NMR (270 MHz, CDCl$_3$) δ 0.98 (t, 3H, J=7.6 Hz), 1.26 (t, 3H, J=7.4 Hz), 1.88 (q, 2H, J=7.4 Hz), 2.51 (s, 3H), 2.62 (q, 2H, J=7.6 Hz), 3.93 (s, 2H), 4.20 (q, 2H, J=7.0 Hz), 11.6 (br, 1H).

REFERENCE EXAMPLE 36

7-Benzyl-2,6-dichloro-8-cyclopentylpurine (Compound C1)

To 7-benzyl-8-cyclopentyl-3-(4-methoxybenzyl)xanthine (6.81 g, 15.8 mmol), which was obtained by the method described in International Patent Publication in Japanese (Kohyo) No. 8-500344, was added phosphorus oxychloride (60.0 mL, 644 mmol, 41 equivalents), and the mixture was refluxed with heating for 6 hours. The reaction solution was concentrated under reduced pressure and the solvent was further azeotroped with toluene. To the residue was carefully added ethyl acetate and saturated aqueous sodium hydrogen carbonate, and the mixture was stirred at room temperature for 30 minutes. The organic layer was extracted with ethyl acetate, the extract was washed with saturated aqueous sodium chloride and dried over anhydrous sodium sulfate, and then the solvent was evaporated. The residue was purified by silica gel column chromatography (ethyl acetate: n-hexane=33:67) to obtain the title compound (4.94 g, 90%).

$^1$H-NMR (270 MHz, CDCl$_3$) δ 1.56–1.70 (m, 2H), 1.88–2.09 (m, 6H), 3.23 (quin, 1H, J=7.9 Hz), 5.70 (s, 2H), 6.94–6.97 (m, 2H), 7.32–7.37 (m, 3H).

REFERENCE EXAMPLE 37

(R)-7-Benzyl-2-chloro-8-cyclopentyl-6-(1-hydroxy-3-phenylpropan-2-ylamino)purine (Compound C2)

Compound C1 (1.64 g, 4.72 mmol) was dissolved in N,N-dimethylformamide (15 mL), and to the solution were added (R)-phenylalaminol (1.07 g, 7.08 mmol, 1.5 equivalents) and diisopropylethylamine (1.64 mL, 9.41 mmol, 2.0 equivalents), and then the mixture was stirred at room temperature for 24 hours. After the reaction solution was concentrated under reduced pressure, ethyl acetate and water were added to the residue and the deposited solid (1.14 g) was collected by filtration. The filtrate was extracted with ethyl acetate, the organic layer was washed with saturated aqueous sodium chloride and dried over anhydrous sodium sulfate, and then the solvent was evaporated. The residue was purified by silica gel column chromatography (chloroform:methanol=90:10) to obtain the title compound (1.88 g, 86% in total).

$^1$H-NMR (270 MHz, CDCl$_3$) δ 1.48–1.73 (m, 2H), 1.76–2.07 (m, 6H), 2.67–2.75 (m, 2H), 3.08 (dd, 1H, J=13.3, 8.5 Hz), 3.11 (quin, 1H, J=8.4 Hz), 3.31 (dd, 1H, J=13.3, 4.8 Hz), 4.37 (m, 1H), 5.55 (d, 1H, J=15.9 Hz), 5.65 (d, 1H, J=15.9 Hz), 7.10–7.38 (m, 10H).

REFERENCE EXAMPLE 38

(R)-7-Benzyl-2-chloro-8-cyclopentyl-6-[3-(4-fluorophenyl)-1-hydroxypropan-2-ylamino]purine (Compound C3)

The title compound (1.75 g, 77%) was obtained from Compound C1 (1.64 g, 4.72 mmol) and Compound A11 (1.20 g, 7.09 mmol, 1.5 equivalents) in a manner similar to that in Reference Example 37.

$^1$H-NMR (270 MHz, CDCl$_3$) δ 1.53–1.62 (m, 2H), 1.80–2.02 (m, 6H), 2.61–2.73 (m, 2H), 3.04 (dd, 1H, J=13.6, 7.6 Hz), 3.11–3.31 (m, 2H), 4.38 (m, 1H), 5.52 (d, 1H, J=15.8 Hz), 5.62 (d, 1H, J=15.8 Hz), 6.84–7.41 (m, 9H).

REFERENCE EXAMPLE 39

6-Amino-5-benzylamino-1-(4-methoxybenzyl)uracil (Compound C4)

5,6-Diamino-1-(4-methoxybenzyl)uracil (15.1 g, 57.5 mmol), which was obtained by the method described in International Patent Publication in Japanese No. 8-500344, was dissolved in acetic acid (25 mL) and water (100 mL). To the solution was added benzaldehyde (7.00 mL, 68.9 mmol, 1.2 equivalents), and the mixture was stirred at room temperature for 90 minutes. To the reaction solution was added water (100 mL), and the deposited imine compound (17.4 g, 86%) was collected by filtration. The imine compound was dissolved in methanol (250 mL) and dichloromethane (250 mL), to the solution were added sodium cyanoborohydride (4.28 g, 63.7 mmol, 1.2 equivalents) and then acetic acid (3.0 mL), and the mixture was stirred at room temperature for 12 hours. After the reaction solution was concentrated, methanol was added to the residue, and the deposited solid was collected by filtration, washed with methanol and dried to obtain the title compound (10.2 g, 58%).

$^1$H-NMR (270 MHz, DMSO-d$_6$) δ 3.73 (s, 3H), 3.84 (s, 2H), 4.94 (s, 2H), 6.36 (brs, 2H), 6.87 (d, 2H, J=8.6 Hz), 7.05 (d, 2H, J=8.6 Hz), 7.24–7.34 (m, 5H).

REFERENCE EXAMPLE 40

7-Benzyl-8-(tert-butyl)-3-(4-methoxybenzyl)xanthine (Compound C5)

Compound C4 (10.2 g, 29.0 mmol) was dissolved in pyridine (10 mL), to the solution was added pivaloyl chloride (3.50 mL, 30.5 mmol, 1.1 equivalents), and then the mixture was stirred at room temperature for 24 hours. After the reaction solution was concentrated, ethyl acetate was added to the resulting residue, and the deposited solid (7.51 g, 59%) was collected by filtration. The resulting solid was dissolved in 2 mol/L aqueous sodium hydroxide (50 mL), the mixture was refluxed with heating for 1 hour, and the reaction mixture was adjusted to pH 6 with 4 mol/L hydrochloric acid under ice cooling. The deposited solid was collected by filtration and dried under reduced pressure to obtain the title compound (6.61 g, 92%).

¹H-NMR (270 MHz, DMSO-$d_6$) δ 1.28 (s, 9H), 3.72 (s, 3H), 5.02 (s, 2H), 5.75 (brs, 2H), 6.88 (d, 2H, J=8.6 Hz), 6.95 (d, 2H, J=7.3 Hz), 7.22–7.33 (m, 3H), 7.38 (d, 2H, J=8.6 Hz).

REFERENCE EXAMPLE 41

(R)-7-Benzyl-8-(tert-butyl)-2-chloro-6-(1-hydroxy-3-phenylpropan-2-ylamino)purine (Compound C6)

7-Benzyl-8-(tert-butyl)-2,6-dichloropurine (2.18 g, 41%) was obtained from Compound C5 (6.61 g, 15.8 mmol) in a manner similar to that in Reference Example 36, and the title compound was obtained in a manner similar to that in Reference Example 37.
¹H-NMR (270 MHz, CDCl₃) δ 1.51 (s, 9H), 2.52–2.61 (m, 2H), 3.28 (dd, 1H, J=13.5, 8.6 Hz), 3.42 (dd, 1H, J=13.5, 4.9 Hz), 4.36 (m, 1H), 4.75 (brd, 1H, J=8.5 Hz), 5.46 (d, 1H, J=15.7 Hz), 5.68 (d, 1H, J=15.7 Hz), 6.93–6.97 (m, 2H), 7.08 (d, 2H, J=7.6 Hz), 7.22–7.41 (m, 6H).

REFERENCE EXAMPLE 42

8-(tert-Butyl)-6-chloro-2-methylthiopurine (Compound C7)

4,5-Diamino-6-hydroxy-2-mercaptopyrimidine (15.0 g, 94.8 mmol) was dissolved in pyridine (200 mL), to the solution was added pivaloyl chloride (14.0 mL, 0.11 mol, 1.2 equivalents), and then the mixture was stirred at room temperature for 12 hours. After the reaction solution was concentrated, to the residue was added acetone, and the deposited solid (18.5 g, 81%) was collected by filtration. The resulting solid was dissolved in 0.5 mol/L aqueous sodium hydroxide (150 mL), to the solution was added methyl iodide (5.30 mL, 85.1 mmol, 1.1 equivalents), and the mixture was stirred overnight at room temperature. After the reaction mixture was cooled on an ice bath and adjusted to pH 6.5 with 4 mol/L hydrochloric acid, the deposited solid (19.6 g, 99%) was collected by filtration. To the resulting solid was added phosphorus oxychloride (60 mL, 0.643 mol, 8.4 equivalents) and the mixture was refluxed with heating for 5 hours. After the reaction solution was concentrated under reduced pressure and the solvent was azeotroped with toluene, ethyl acetate and saturated aqueous sodium hydrogen carbonate were carefully added to the residue, and then the mixture was stirred at room temperature for 30 minutes. The reaction mixture was extracted with ethyl acetate, the organic layer was washed with saturated aqueous sodium chloride and dried over anhydrous sodium sulfate, and then the solvent was evaporated. The residue was purified by silica gel column chromatography (chloroform:methanol=95:5) to obtain the title compound (16.7 g, 90%).
¹H-NMR (270 MHz, CDCl₃) δ 1.55 (s, 9H), 2.59 (s, 3H), 9.86 (br, 1H).

REFERENCE EXAMPLE 43

(R)-8-(tert-Butyl)-6-(1-hydroxy-3-phenylpropan-2-ylamino)-2-methylsulfonyl-7H-purine (Compound C8)

Compound C7 (16.7 g, 62.1 mmol) was dissolved in n-butanol (50 mL), to the solution were added (R)-phenylalaminol (14.0 g, 92.6 mmol, 1.5 equivalents) and diisopropylethylamine (16.4 mL, 94.1 mmol, 1.5 equivalents), and the mixture was stirred at 150° C. for 1 hour. The reaction solution was concentrated under reduced pressure, to the concentrate were added saturated aqueous ammonium chloride and the mixture was extracted with ethyl acetate. The organic layer was washed with saturated aqueous sodium chloride and dried over anhydrous sodium sulfate, and the solvent was evaporated. The residue was purified by silica gel column chromatography (chloroform:methanol=95:5) to obtain (R)-8-(tert-butyl)-6-(1-hydroxy-3-phenylpropan-2-ylamino)-2-methylthio-7H-purine (Compound C9, 9.50 g, 39%). Compound C9 (5.63 g, 15.8 mmol) was dissolved in methanol (200 mL) and water (50 mL), to the solution was added a monopersulfate compound (19.4 g, 31.5 mmol, 2.0 equivalents), and then the mixture was stirred at room temperature for 2 hours. After the reaction solution was concentrated, the resulting residue was extracted with chloroform, the organic layer was washed with saturated aqueous sodium chloride and dried over anhydrous sodium sulfate, and the solvent was evaporated. The residue was purified by silica gel column chromatography (chloroform:methanol=95:5) to obtain the title compound (7.89 g, 96%).
¹H-NMR (270 MHz, DMSO-$d_6$) δ 2.06 (s, 9H), 2.86–3.00 (m, 2H), 3.38 (s, 3H), 3.51–3.62 (m, 2H), 4.42 (br, 1H), 4.82 (m, 1H), 7.10–7.34 (m, 5H), 7.90 (br, 1H), 12.9 (br, 1H).

REFERENCE EXAMPLE 44

(R)-8-Cyclopentyl-6-(1-hydroxy-3-phenylpropan-2-ylamino)-2-methylsulfonyl-7H-purine (Compound C10)

The title compound was obtained from 4,5-diamino-6-hydroxy-2-mercaptopyrimidine and cyclopentylcarbonyl chloride in a manner similar to that in Reference Examples 42 and 43.
¹H-NMR (270 MHz, DMSO-$d_6$) δ 1.68–2.08 (m, 8H), 2.86–2.97 (m, 2H), 3.25 (m, 1H), 3.33 (s, 3H), 3.50–3.62 (m, 2H), 4.48 (br, 1H), 4.87 (m, 1H), 7.13–7.28 (m, 5H), 7.84 (br, 1H), 13.1 (br, 1H).

EXAMPLE 1

(S)-2-Cyclopentyl-7,8-dihydro-8-(4-picolyl)-4-(n-propyl)-1H-imidazo[2,1-i]purin-5(4H)-one (Compound 1)

8-Cyclopentyl-6-methylthio-3-(n-propyl)-7H-purin-2(3H)-one (Compound B1, 576 mg, 1.97 mmol), which was obtained by the method described in Journal of Heterocyclic Chemistry (J. Heterocycl. Chem.), 30, p. 241, 1993, and Compound A3 (300 mg, 1.97 mmol, 1.0 equivalent) obtained in Reference Examples 1–3 were stirred in pyridine (1 mL) at 150° C. for 5 hours. The solvent was evaporated under reduced pressure, and the resulting residue was purified by silica gel column chromatography (chloroform:methanol=100:0 to 90:10) to obtain (S)-8-cyclopentyl-6-[1-hydroxy-3-(4-pyridyl)propan-2-ylamino]-3-(n-propyl)-7H-purin-2(3H)-one (Compound 1a, 578 mg, 74%).
To Compound 1a (578 mg, 1.46 mmol) was added thionyl chloride (5.0 mL, 68.5 mmol, 47 equivalents) and the mixture was stirred at 60° C. for 2 hours. Excess thionyl chloride was evaporated, to the resulting residue were added chloroform (10 mL) and saturated aqueous sodium hydrogen carbonate (10 mL), and the mixture was stirred at room temperature for 12 hours. The reaction mixture was extracted with chloroform, the organic layer was washed with saturated aqueous sodium chloride and dried over anhydrous magnesium sulfate, and the solvent was evaporated under reduced pressure. The residue was purified by silica gel column chromatography (chloroform:methanol=98:2), and chloroform and methanol were added to the residue. The deposited crystals were collected by filtration to obtain the title compound (310 mg, 56%) as a white solid.

Compound 1a was also obtained by the method described below.

OXONE® (Aldrich, 2.46 g, 4.00 mmol, 4.0 equivalents), water (10 mL) and chloroform (10 mL) were mixed and cooled to 0–5° C. To the reaction mixture were added Compound B1 (292 mg, 1.00 mmol) and then tetrabutylammonium hydrogensulfate (136 mg, 0.40 mmol, 0.4 equivalents), and the mixture was stirred at the same temperature for 2 hours. Phase separation was carried out by using chloroform, and the resulting organic layer was dried over anhydrous magnesium sulfate and filtered. To the filtrate were added Compounds A3 (152 mg, 1.00 mmol, 1.0 equivalent) obtained in Reference Examples 1–3 and N,N-diisopropylethylamine (178 μL, 1.00 mmol, 1.0 equivalent), and the mixture was concentrated. To the resulting residue was added pyridine (4 mL), and the mixture was stirred at 50° C. for 4 hours. To the reaction mixture was further added Compound A3 (76 mg, 0.50 mmol, 0.5 equivalent), and the mixture was stirred for 3 hours. After the reaction mixture was concentrated, the residue was purified by silica gel column chromatography (ethyl acetate:methanol) to obtain Compound 1a (300 mg, 76%).

Melting point: 256–257° C. (chloroform/methanol)
$^1$H-NMR (270 MHz, DMSO-$d_6$) δ 0.83 (t, 3H, J=7.4 Hz), 1.57–1.95 (m, 10H), 2.88 (d, 2H, J=7.3 Hz), 3.06 (m, 1H), 3.55 (m, 1H), 3.79 (t, 2H, J=7.3 Hz), 3.91 (t, 1H, J=10.4 Hz), 4.53 (m, 1H), 7.32 (d, 2H, J=5.6 Hz), 8.45 (d, 2H, J=5.6 Hz).
IR (KBr): 1693, 1656, 1009, 744 cm$^{-1}$
TOF-MS: m/z 379 (M$^+$+1).
Elemental Analysis for $C_{21}H_{26}N_6O$
Calculated (%): C, 66.64; H, 6.92; N, 22.21. Found (%): C, 66.71; H, 7.00; N, 22.14.

EXAMPLE 2

(R)-2-Cyclopentyl-7,8-dihydro-8-(4-picolyl)-4-(n-propyl)-1H-imidazo[2,1-i]purin-5(4H)-one D-tartrate (Compound 2)

In a manner similar to that in Example 1, the title compound in the free form (Compound 2a, 20.4 g, 51%) was obtained from Compound B1 (30.7 g, 105 mmol) and (R)-2-amino-3-(4-pyridyl)-1-propanol (Compound A4, 16.0 g, 105 mmol, 1.0 equivalent), which was obtained from (R)-N-(tert-butoxycarbonyl)-β-(4-pyridyl)-α-alanine in a manner similar to that in Reference Examples 1–3. To Compound 2a (18.0 g, 47.6 mmol) was added D-tartaric acid (7.14 g, 47.6 mmol, 1.0 equivalent) and recrystallization was performed from ethanol and water to obtain the title compound (23.5 g, 92%) as a white solid.

Melting point: 223–224° C. (ethanol/water)
$^1$H-NMR (270 MHz, DMSO-$d_6$) δ 0.85 (t, 3H, J=7.4 Hz), 1.59–2.02 (m, 10H), 2.93 (d, 2H, J=6.9 Hz), 3.23 (m, 1H), 3.60 (dd, 1H, J=10.9, 6.9 Hz), 3.82 (t, 2H, J=7.1 Hz), 3.98 (t, 1H, J=10.4 Hz), 4.27 (s, 2H), 4.58 (m, 1H), 7.37 (d, 2H, J=5.6 Hz), 8.47 (d, 2H, J=5.6 Hz).
IR (KBr): 1716, 1679, 1577 cm$^{-1}$
TOF-MS: m/z 379 (M$^+$+1).
Elemental Analysis for $C_{21}H_{26}N_6O \cdot C_4H_6O_6 \cdot 0.5H_2O$
Calculated (%): C, 55.86; H, 6.19; N, 15.63. Found (%): C, 56.03; H, 6.06; N, 15.45.

EXAMPLE 3

2-Cyclopentyl-7,8-dihydro-8-(2-picolyl)-4-(n-propyl)-1H-imidazo[2,1-i]purin-5(4H)-one (Compound 3)

In a manner similar to that in Example 1, the title compound (103 mg, 20%) was obtained as a white solid from Compound B1 (483 mg, 1.64 mmol) and Compound A5 (505 mg, 3.28 mmol, 2.0 equivalents) prepared in Reference Example 4.

Melting point: 147–150° C. (methanol/chloroform)
$^1$H-NMR (270 MHz, CDCl$_3$) δ 0.98 (t, 3H, J=7.3 Hz), 1.63–1.89 (m, 8H), 1.98–2.08 (m, 2H), 3.01–3.19 (m, 3H), 3.87 (dd, 1H, J=11.2, 6.8 Hz), 4.04 (t, 2H, J=7.2 Hz), 4.16 (t, 1H, J=10.0 Hz), 4.70 (m, 1H), 7.09–7.16 (m, 2H), 7.53 (dt, 1H, J=8.0, 1.7 Hz), 8.53 (d, 1H, J=4.6 Hz).
IR (CHCl$_3$): 1693, 1655 cm$^{-1}$
EI-MS: m/z 378 (M$^+$).

EXAMPLE 4

2-Cyclopentyl-7,8-dihydro-8-(3-picolyl)-4-(n-propyl)-1H-imidazo[2,1-i]purin-5(4H)-one (Compound 4)

In a manner similar to that in Example 1, the title compound (51 mg, 14%) was obtained from Compound B1 (290 mg, 0.99 mmol) and Compound A6 (300 mg, 1.97 mmol, 2.0 equivalents) prepared in Reference Example 5.

Melting point: 247–250° C. (ethyl acetate/diethyl ether)
$^1$H-NMR (270 MHz, DMSO-$d_6$) δ 0.90 (t, 3H, J=7.6 Hz), 1.67–1.76 (m, 8H), 2.08 (m, 2H), 3.29–3.31 (m, 3H), 3.98–4.08 (m, 3H), 4.31 (t, 1H, J=10.5 Hz), 4.85 (m, 1H), 8.02 (t, 1H, J=6.0 Hz), 8.53 (d, 1H, J=7.8 Hz), 8.85 (d, 1H, J=5.2 Hz), 8.90 (s, 1H).
IR (CHCl$_3$): 1718, 1678 cm$^{-1}$
FAB-MS: m/z 379 (M$^+$+1).

EXAMPLE 5

2-Cyclopentyl-7,8-dihydro-8-(2-methylthiazol-4-ylmethyl)-4-(n-propyl)-1H-imidazo[2,1-i]purin-5(4H)-one hydrochloride (Compound 5)

In a manner similar to that in Example 1, the title compound in the free form was obtained from Compound B1 (450 mg, 1.53 mmol) and Compound A7 (526 mg, 3.06 mmol, 2.0 equivalents) prepared in Reference Example 6, and then it was converted into hydrochloride with 4 mol/L hydrogen chloride in dioxane to obtain the title compound (100 mg, 15%) as a white solid.

Melting point: 125–128° C. (ethanol)
$^1$H-NMR (270 MHz, DMSO-$d_6$) δ 0.89 (t, 3H, J=7.2 Hz), 1.65–1.77 (m, 8H), 2.01–2.11 (m, 2H), 2.64 (s, 3H), 3.15 (d, 2H, J=6.6 Hz), 3.31 (m, 1H), 3.98 (t, 2H, J=7.3 Hz), 4.07 (dd, 1H, J=11.3, 6.3 Hz), 4.29 (t, 1H, J=11.3 Hz), 4.76 (m, 1H), 7.34 (s, 1H), 10.6 (brs, 1H).
IR (CHCl$_3$): 1716, 1676, 1584 cm$^{-1}$
FAB-MS: m/z 399 (M$^+$+1).

EXAMPLE 6

2-Cyclopentyl-7,8-dihydro-4-(n-propyl)-8-(2-pyrazinylmethyl)-1H-imidazo[2,1-i]purin-5(4H)-one (Compound 6)

In a manner similar to that in Example 1, the title compound (130 mg, 10%) was obtained as a white solid from Compound B1 (954 mg, 3.27 mmol) and Compound A8 (500 mg, 3.27 mmol, 1.0 equivalent) prepared in Reference Example 7.

Melting point: 225–228° C. (methanol/chloroform)

$^1$H-NMR (270 MHz, CDCl$_3$) δ 0.98 (t, 3H, J=7.6 Hz), 1.71–1.93 (m, 8H), 2.12–2.21 (m, 2H), 3.22–3.32 (m, 2H), 3.49 (dd, 1H, J=15.7, 5.9 Hz), 4.11 (t, 2H, J=7.6 Hz), 4.22 (dd, 1H, J=11.9, 6.8 Hz), 4.51 (dd, 1H, J=11.9, 10.3 Hz), 4.98 (m, 1H), 8.52 (d, 1H, J=2.2 Hz), 8.56 (s, 1H), 8.58 (d, 1H, J=2.2 Hz).

IR (CHCl$_3$): 1716, 1684, 1587 cm$^{-1}$

FAB-MS: m/z 380 (M$^+$+1).

EXAMPLE 7

2-Cyclopentyl-7,8-dihydro-4-(n-propyl)-8-(4-pyrimidinylmethyl)-1H-imidazo[2,1-i]purin-5(4H)-one (Compound 7)

In a manner similar to that in Example 1, the title compound (32 mg, 3%) was obtained as a white solid from Compound B1 (954 mg, 3.27 mmol) and Compound A9 (500 mg, 3.27 mmol, 1.0 equivalent) prepared in Reference Example 8.

Melting point: 255–260° C. (methanol/ethyl acetate)

$^1$H-NMR (270 MHz, CDCl$_3$) δ 0.97 (t, 3H, J=7.3 Hz), 1.67–1.82 (m, 8H), 1.99–2.09 (m, 2H), 3.02–3.22 (m, 3H), 3.88 (dd, 1H, J=11.6, 4.1 Hz), 4.01 (t, 2H, J=7.6 Hz), 4.21 (t, 1H, J=11.6 Hz), 4.80 (m, 1H), 7.23 (d, 1H, J=5.1 Hz), 8.62 (d, 1H, J=5.1 Hz), 9.13 (s, 1H).

IR (CHCl$_3$): 1690, 1655, 1591 cm$^{-1}$

FAB-MS: m/z 380 (M$^+$+1).

EXAMPLE 8

7,8-Dihydro-8-(4-picolyl)-2,4-dipropyl-1H-imidazo[2,1-i]purin-5(4H)-one (Compound 8)

In a manner similar to that in Example 1, the title compound (195 mg, 55%) was obtained as a white solid from Compound B2 (266 mg, 1.00 mmol) prepared in Reference Example 14 and Compound A10 (304 mg, 2.00 mmol, 2.0 equivalents) prepared in Reference Example 9.

Melting point: 270–274° C. (ethyl acetate/diethyl ether)

$^1$H-NMR (270 MHz, CDCl$_3$) δ 0.95–1.02 (m, 6H), 1.71–1.87 (m, 4H), 2.69–2.75 (m, 2H), 2.83–2.93 (m, 2H), 3.72 (dd, 1H, J=11.2, 6.6 Hz), 4.01 (t, 2H, J=5.9 Hz), 4.10 (t, 1H, J=11.2 Hz), 4.35 (m, 1H), 7.25 (d, 2H, J=4.6 Hz), 8.55 (d, 2H, J=4.6 Hz).

IR (CHCl$_3$): 1690, 1653 cm$^{-1}$

EI-MS: m/z 352 (M$^+$).

Elemental Analysis for C$_{19}$H$_{24}$N$_6$O

Calculated (%): C, 64.75; H, 6.86; N, 23.85. Found (%): C, 64.80; H, 7.00; N, 24.02.

EXAMPLE 9

(R)-2-Cyclohexyl-7,8-dihydro-8-(4-picolyl)-4-(n-propyl)-1H-imidazo[2,1-i]purin-5(4H)-one (Compound 9)

In a manner similar to that in Example 1, the title compound (510 mg, 40%) was obtained as a white solid from Compound B3 (1.00 g, 3.27 mmol) prepared in Reference Example 15 and Compound A4 (750 mg, 4.93 mmol, 1.5 equivalents).

Melting point: 262–263° C. (ethanol)

$^1$H-NMR (270 MHz, CDCl$_3$) δ 0.96 (t, 3H, J=7.5 Hz), 1.20–1.58 (m, 6H), 1.70–1.86 (m, 4H), 2.01–2.05 (m, 2H), 2.76 (m, 1H), 2.88 (dd, 1H, J=13.3, 5.8 Hz), 2.95 (dd, 1H, J=13.2, 7.6 Hz), 3.69 (dd, 1H, J=11.2, 6.9 Hz), 3.98 (t, 2H, J=7.5 Hz), 4.07 (t, 1H, J=10.6 Hz), 4.49 (m, 1H), 7.24 (d, 2H, J=4.6 Hz), 8.55 (d, 2H, J=4.6 Hz).

IR (KBr): 2929, 1687, 1660, 746 cm$^{-1}$

TOF-MS: m/z 393 (M$^+$+1).

Elemental Analysis for C$_{22}$H$_{28}$N$_6$O

Calculated (%): C, 67.32; H, 7.19; N, 21.41. Found (%): C, 67.85; H, 7.54; N, 21.57.

EXAMPLE 10

(R)-2-Cyclobutyl-7,8-dihydro-8-(4-picolyl)-4-(n-propyl)-1H-imidazo[2,1-i]purin-5(4H)-one D-tartrate (Compound 10)

In a manner similar to that in Example 1, the title compound in the free form (Compound 10a, 100 mg, 11%) was obtained from Compound B5 (700 mg, 2.52 mmol) prepared in Reference Example 16 and Compound A4 (570 mg, 3.75 mmol, 1.5 equivalents). To a solution (1 mL) of Compound 10a (100 mg, 0.27 mmol) in methanol was added a solution (1 mL) of D-tartaric acid (83 mg, 0.27 mmol, 1.0 equivalent) in methanol, and the mixture was concentrated. Then the resulting solid was recrystallized from ethanol and water to obtain the title compound (60 mg, 43%) as a white solid.

Melting point: 203–204° C. (ethanol/water)

$^1$H-NMR (270 MHz, CDCl$_3$) δ 0.86 (t, 3H, J=7.6 Hz), 1.60–1.68 (m, 2H), 1.85–2.02 (m, 2H), 2.25–2.35 (m, 4H), 2.94 (d, 2H, J=7.0 Hz), 3.54 (m, 1H), 3.62 (dd, 1H, J=10.3, 7.0 Hz), 3.84 (t, 2H, J=7.6 Hz), 3.99 (t, 1H, J=10.5 Hz), 4.59 (m, 1H), 7.33 (d, 2H, J=5.9 Hz), 8.47 (d, 2H, J=5.9 Hz).

IR (KBr): 1714, 1681, 1585 cm$^{-1}$

TOF-MS: m/z 365 (M$^+$+1).

Elemental Analysis for C$_{20}$H$_{24}$N$_6$O.C$_4$H$_6$O$_6$.0.25H$_2$O

Calculated (%): C, 55.53; H, 5.92; N, 16.19. Found (%): C, 55.48; H, 5.89; N, 16.12.

EXAMPLE 11

2-(tert-Butyl)-7,8-dihydro-8-(4-picolyl)-4-(n-propyl)-1H-imidazo[2,1-i]purin-5(4H)-one (Compound 11)

In a manner similar to that in Example 1, the title compound (231 mg, 63%) was obtained as a white solid from Compound B6 (280 mg, 1.00 mmol) prepared in Reference Example 17 and Compound A10 (304 mg, 2.00 mmol, 2.0 equivalents) prepared in Reference Example 9.

Melting point: 293–295° C. (ethyl acetate/diethyl ether)

$^1$H-NMR (270 MHz, CDCl$_3$) δ 0.97 (t, 3H, J=7.3 Hz), 1.40 (s, 9H), 1.74–1.84 (m, 2H), 2.86–2.96 (m, 2H), 3.66

(dd, 1H, J=10.9, 7.3 Hz), 3.99 (t, 2H, J=7.2 Hz), 4.10 (t, 1H, J=10.9 Hz), 4.55 (m, 1H), 7.29 (d, 2H, J=4.6 Hz), 8.65 (d, 2H, J=4.6 Hz).
IR (CHCl$_3$): 1690, 1655 cm$^{-1}$
EI-MS: m/z 366 (M$^+$).
Elemental Analysis for $C_{20}H_{26}N_6O$
Calculated (%): C, 65.55; H, 7.15; N, 22.93. Found (%): C, 65.40; H, 7.25; N, 22.98.

EXAMPLE 12

7,8-Dihydro-2-(1-methylcyclohexyl)-8-(4-picolyl)-4-(n-propyl)-1H-imidazo[2,1-i]purin-5(4H)-one dihydrochloride (Compound 12)

In a manner similar to that in Example 1, the title compound in the free form was obtained from Compound B7 (300 mg, 0.94 mmol) prepared in Reference Example 18 and Compound A10 (200 mg, 1.32 mmol, 1.4 equivalents) prepared in Reference Example 9. The resulting product was converted into hydrochloride with a 4 mol/L solution of hydrogen chloride in dioxane and it was recrystallized from hexane and ethyl acetate to obtain the title compound (240 mg, 53%) as a white solid.

Melting point: 149–150° C. (hexane/ethyl acetate)
$^1$H-NMR (270 MHz, CDCl$_3$) δ 0.95 (t, 3H, J=7.4 Hz), 1.30 (s, 3H), 1.24–1.76 (m, 10H), 2.08–2.17 (m, 2H), 3.45 (m, 1H), 3.59 (m, 1H), 4.05–4.11 (m, 3H), 4.68 (m, 1H), 5.20 (m, 1H), 8.19 (d, 2H, J=4.6 Hz), 8.89 (d, 2H, J=4.6 Hz).
IR (KBr): 2809, 1716, 1679, 1589, 742 cm$^{-1}$
FAB-MS: m/z 407 (M$^+$+1).
Elemental Analysis for $C_{23}H_{30}N_6O \cdot 2HCl \cdot 2H_2O$
Calculated (%): C, 53.59; H, 7.04; N, 16.30. Found (%): C, 53.48; H, 7.06; N, 16.09.

EXAMPLE 13

7,8-Dihydro-8-(4-picolyl)-4-(n-propyl)-1H-imidazo[2,1-i]purin-5(4H)-one (Compound 13)

6-Methylthio-3-(n-propyl)-7H-purin-2(3H)-one (Compound B8, 6.80 g, 30.3 mmol), which was obtained by the method described in Journal of Heterocyclic Chemistry (J. Heterocycl. Chem.), 30, p. 241, 1993, was dissolved in N,N-dimethylformamide (100 mL). To the solution were added potassium carbonate (8.40 g, 60.8 mmol, 2.0 equivalents) and benzyl bromide (3.90 mL, 33.1 mmol, 1.1 equivalents), and the mixture was stirred at room temperature for 2 hours. After the reaction mixture was concentrated, to the residue was added water, and the resulting crystals were washed with water and diethyl ether and dried under reduced pressure to obtain a 7-benzyl compound (Compound 13a, 7.22 g, 75%). Compound 13a (2.00 g, 6.36 mmol) was dissolved in pyridine (30 mL), to the solution was added Compound A10 (1.90 g, 12.8 mmol, 2.0 equivalents) obtained in Reference Example 9, and the mixture was stirred under reflux with heating for 10 hours. After the pyridine was evaporated, the residue was directly purified by silica gel column chromatography (chloroform:methanol=10:1) to obtain an adduct (940 mg, 35%). To the resulting adduct (940 mg, 2.25 mmol) was added thionyl chloride (5 mL) and the mixture was stirred with heating at 60° C. for 2.5 hours. After the thionyl chloride was evaporated, the residue was neutralized with saturated aqueous sodium hydrogen carbonate and the mixture was extracted with chloroform. The organic layer was washed with saturated aqueous sodium chloride and dried over anhydrous sodium sulfate, and the solvent was evaporated. The residue was purified by silica gel column chromatography (chloroform:methanol=98:2) to obtain a cyclized compound (570 mg, 64%). The resulting cyclized compound (20 mg, 0.05 mmol) was dissolved in methanol (2 mL), to the solution were added 20% palladium hydroxide/carbon (10 mg) and ammonium formate (20 mg, 0.35 mmol, 7.0 equivalents), and then the mixture was refluxed for 4 hours. After the catalyst was removed by filtration, the reaction mixture was concentrated and neutralized with saturated aqueous sodium hydrogen carbonate. The reaction solution was extracted with chloroform, the organic layer was washed with saturated aqueous sodium chloride and dried, and then the solvent was evaporated. The residue was purified by silica gel column chromatography (chloroform:methanol=95:5) to obtain the title compound (10 mg, 23%).

$^1$H-NMR (270 MHz, CDCl$_3$) δ 0.99 (t, 3H, J=7.3 Hz), 1.82 (q, 2H, J=7.3 Hz), 2.94 (m, 2H), 3.84 (dd, 1H, J=11.2, 5.9 Hz), 4.06 (t, 2H, J=7.3 Hz), 4.11 (t, 1H, J=10.9 Hz), 4.30 (m, 1H), 7.15 (d, 2H, J=5.6 Hz), 7.65 (s, 1H), 8.50 (d, 2H, J=5.9 Hz).
EI-MS: m/z 308 (M$^+$).

EXAMPLE 14

2-Cyclopentyl-4-cyclopropylmethyl-7,8-dihydro-8-(4-picolyl)-1H-imidazo[2,1-i]purin-5(4H)-one dihydrochloride (Compound 14)

In a manner similar to that in Example 1, the title compound in the free form (500 mg, 78%) was obtained from Compound B9 (500 mg, 1.71 mmol) prepared in Reference Example 19 and Compound A10 (350 mg, 2.32 mmol, 1.4 equivalents) prepared in Reference Example 9. The resulting product was converted into hydrochloride with a 4 mol/L solution of hydrogen chloride in dioxane and it was recrystallized from ethanol to obtain the title compound (540 mg, 71%) as a white solid.

Melting point: 240–241° C. (ethanol)
$^1$H-NMR (270 MHz, DMSO-d$_6$) δ 0.47–0.50 (m, 4H), 1.25 (m, 1H), 1.76–1.90 (m, 6H), 2.06–2.20 (m, 2H), 3.28–3.38 (m, 3H), 3.92 (d, 2H, J=6.9 Hz), 4.06 (m, 1H), 4.34 (t, 1H, J=9.2 Hz), 4.87 (m, 1H), 7.95 (d, 2H, J=6.3 Hz), 8.86 (d, 2H, J=6.3 Hz).
IR (KBr): 1720, 1673, 1637, 746 cm$^{-1}$
FAB-MS: m/z 391 (M$^+$+1).
Elemental Analysis for $C_{22}H_{26}N_6O \cdot 2HCl \cdot 1.2H_2O$
Calculated (%): C, 54.48; H, 6.32; N, 17.33. Found (%): C, 54.51; H, 6.41; N, 17.14.

EXAMPLE 15

2-(tert-Butyl)-4-cyclopropylmethyl-7,8-dihydro-8-(4-picolyl)-1H-imidazo[2,1-i]purin-5(4H)-one dihydrochloride (Compound 15)

In a manner similar to that in Example 1, the title compound in the free form was obtained from Compound B10 (700 mg, 2.45 mmol) prepared in Reference Example 20 and Compound A10 (500 mg, 3.33 mmol, 1.4 equivalents) prepared in Reference Example 9. The resulting product was converted into hydrochloride with a 4 mol/L solution of hydrogen chloride in dioxane and it was recrystallized from ethanol to obtain the title compound (380 mg, 35%) as a white solid.

Melting point: 205–206° C. (ethanol)

¹H-NMR (270 MHz, DMSO-d₆) δ 0.46–0.55 (m, 4H), 1.37 (m, 1H), 1.44 (s, 9H), 3.34–3.59 (m, 2H), 4.02 (d, 2H, J=7.3 Hz), 4.19 (dd, 1H, J=11.9, 6.3 Hz), 4.51 (t, 1H, J=11.1 Hz), 4.96 (m, 1H), 7.55 (brs, 1H), 8.15 (d, 2H, J=6.3 Hz), 8.76–8.85 (m, 2H), 11.0 (brs, 1H), 13.2 (brs, 1H).

IR (KBr): 2983, 1716, 1673, 1589, 746 cm⁻¹

TOF-MS: m/z 379 (M⁺+1).

Elemental Analysis for $C_{21}H_{26}N_6O \cdot 2HCl \cdot 2.5H_2O$

Calculated (%): C, 50.81; H, 6.70; N, 16.93. Found (%): C, 51.15; H, 6.68; N, 16.76.

EXAMPLE 16

2-Cyclopentyl-4-ethyl-7,8-dihydro-8-(4-picolyl)-1H-imidazo[2,1-i]purin-5(4H)-one dihydrochloride (Compound 16)

In a manner similar to that in Example 1, the title compound in the free form (100 mg, 19%) was obtained from Compound B1 (410 mg, 1.51 mmol) prepared in Reference Example 21 and Compound A10 (310 mg, 2.00 mmol, 1.5 equivalents) prepared in Reference Example 9. The resulting product was converted into hydrochloride with a 4 mol/L solution of hydrogen chloride in dioxane and it was recrystallized from hexane and ethanol to obtain the title compound (60 mg, 9%).

Melting point: 180–181° C. (hexane/ethanol)

¹H-NMR (270 MHz, DMSO-d₆) δ 1.25 (t, 3H, J=6.9 Hz), 1.60–1.90 (m, 6H), 2.00–2.20 (m, 2H), 3.25–3.45 (m, 3H), 3.95–4.15 (m, 3H), 4.32 (t, 1H, J=10.7 Hz), 4.87 (m, 1H), 7.96 (d, 2H, J=5.8 Hz), 8.87 (d, 2H, J=5.8 Hz).

IR (KBr): 1716, 1679, 1583, 1512, 742 cm⁻¹

TOF-MS: m/z 364 (M⁺).

Elemental Analysis for $C_{20}H_{24}N_6O \cdot 2HCl \cdot 2H_2O$

Calculated (%): C, 50.74; H, 6.39; N, 17.75. Found (%): C, 51.15; H, 6.33; N, 17.51.

EXAMPLE 17

1-Benzyl-2-cyclopentyl-7,8-dihydro-8-methylsulfonyloxymethyl-4-(n-propyl)-1H-imidazo[2,1-i]purin-5(4H)-one (Compound 17)

Compound B1 (1.17 g, 4.00 mmol) was dissolved in N,N-dimethylformamide (20 mL), to the solution were added potassium carbonate (607 mg, 4.40 mmol, 1.1 equivalents) and benzyl bromide (523 μL, 4.40 mmol, 1.1 equivalents), and the mixture was stirred at room temperature for 1 hour. To the reaction mixture was further added benzyl bromide (48 μL, 0.40 mmol, 0.1 equivalent), the mixture was stirred at 60° C. for 1 hour, and then methanol was added to the mixture. The reaction mixture was partitioned with ethyl acetate and water, and the organic layer was washed with water, dried over anhydrous magnesium sulfate and concentrated. Then, the residue was purified by silica gel column chromatography (chloroform). To the resulting ocher syrup-like substance was added dl-serinol (547 mg, 6.00 mmol), and the mixture was stirred at 150° C. for 4 hours. The reaction mixture was purified by silica gel column chromatography (chloroform:methanol=98:2 to 90:10) and the resulting substance was recrystallized from chloroform and diethyl ether to obtain white crystals (500 mg). The resulting crystals were dissolved in dichloromethane (5 mL), to the solution were added methanesulfonyl chloride (275 μL, 3.54 mmol) and diisopropylethylamine (923 μL, 5.31 mmol), and the mixture was stirred at room temperature for 2 hours. The reaction mixture was partitioned with chloroform and water, and the resulting organic layer was dried over anhydrous magnesium sulfate. After the organic layer was concentrated, the residue was recrystallized from diethyl ether and hexane to obtain the title compound (500 mg, 26%) as a light brown solid.

¹H-NMR (270 MHz, CDCl₃) δ 0.96 (t, 3H, J=7.6 Hz), 1.73–1.81 (m, 10H), 2.84 (s, 3H), 2.92 (m, 1H), 3.81 (dd, 1H, J=11.2, 7.0 Hz), 3.96 (t, 2H, J=7.3 Hz), 3.99 (m, 1H), 4.22 (dd, 1H, J=10.0, 5.1 Hz), 4.30 (dd, 1H, J=10.0, 4.3 Hz), 4.53 (m, 1H), 5.44 (d, 1H, J=16.5 Hz), 5.53 (d, 1H, J=16.5 Hz), 7.12 (d, 2H, J=6.8 Hz), 7.26–7.35 (m, 3H).

EXAMPLE 18

2-Cyclopentyl-7,8-dihydro-8-methylsulfonyloxymethyl-1-methoxymethyl-4-(n-propyl)-1H-imidazo[2,1-i]purin-5(4H)-one (Compound 18)

Compound B1 (10.2 g, 34.8 mmol) was dissolved in N,N-dimethylformamide (100 mL), to the solution were added potassium carbonate (10.6 g, 76.6 mmol, 2.2 equivalents) and chloromethyl methyl ether (5.30 mL, 70.1 mmol, 2.0 equivalents), and the mixture was stirred at 60° C. for 4 hours. The reaction mixture was partitioned with ethyl acetate and water, and the organic layer was washed with water and dried over anhydrous magnesium sulfate. The organic layer was concentrated, then to the concentrate was added dl-serinol (5.00 g, 36.2 mmol), and the mixture was stirred at 150° C. for 4 hours. The reaction mixture was purified by silica gel column chromatography (ethyl acetate:methanol=95:5 to 75:25) to obtain orange oil (10.0 g). The resulting oil was dissolved in dichloromethane (100 mL), to the solution were added methanesulfonyl chloride (8.12 mL, 104 mmol) and diisopropylethylamine (19.0 mL, 139 mmol), and the mixture was stirred at room temperature for 2 hours. The reaction mixture was partitioned with chloroform and water, and the organic layer was dried over anhydrous magnesium sulfate. The reaction mixture was concentrated and the residue was purified by silica gel column chromatography (ethyl acetate:methanol=100:0 to 90:10) to obtain the title compound (7.48 g, 49%) as an orange solid.

¹H-NMR (270 MHz, CDCl₃) δ 0.96 (t, 3H, J=7.3 Hz), 1.69–2.05 (m, 10H), 3.05 (s, 3H), 3.20 (m, 1H), 3.38 (s, 3H), 3.85 (dd, 1H, J=11.6, 6.5 Hz), 3.94–4.06 (m, 3H), 4.27 (dd, 1H, J=10.5, 5.7 Hz), 4.37 (dd, 1H, J=10.5, 4.3 Hz), 4.59 (m, 1H), 5.59 (s, 2H).

EXAMPLE 19

2-Cyclopentyl-8-(1,3-dioxoisoindolin-2-ylmethyl)-7,8-dihydro-1-methoxymethyl-4-(n-propyl)-1H-imidazo[2,1-i]purin-5(4H)-one (Compound 19)

Compound 18 (500 mg, 0.98 mmol) obtained in Example 18 was dissolved in N,N-dimethylformamide (10 mL), to the solution was added phthalimide potassium salt (485 mg, 2.62 mmol, 2.7 equivalents), and the mixture was stirred at 120° C. for 4 hours. The reaction mixture was partitioned with ethyl acetate and water, and the organic layer was washed with saturated aqueous sodium hydrogen carbonate and dried over anhydrous magnesium sulfate. After the reaction mixture was concentrated, the residue was crystallized from dichloromethane and diethyl ether to obtain the title compound (500 mg, 78%) as white crystals.

¹H-NMR (270 MHz, CDCl₃) δ 0.95 (t, 3H, J=7.6 Hz), 1.59–1.99 (m, 10H), 3.18 (m, 1H), 3.34 (s, 3H), 3.70–3.98

(m, 6H), 4.69 (m, 1H), 5.54 (s, 2H), 7.73 (dd, 2H, J=5.7, 3.2 Hz), 7.87 (dd, 2H, J=5.7, 3.2 Hz).

EXAMPLE 20

8-Aminomethyl-2-cyclopentyl-7,8-dihydro-4-(n-propyl)-1H-imidazo[2,1-i]purin-5(4H)-one dihydrochloride (Compound 20)

Compound 19 (574 mg, 1.31 mmol) obtained in Example 19 was dissolved in methanol (5 mL), to the solution was added hydrazine monohydrate (1 mL), and the mixture was stirred overnight at room temperature. The reaction mixture was partitioned with chloroform and water, and the organic layer was washed with 4 mol/L aqueous sodium hydroxide and dried over anhydrous magnesium sulfate. The organic layer was concentrated, to the concentrate were added a 4 mol/L solution of hydrogen chloride in dioxane (4 mL) and methanol (4 mL), and the mixture was stirred under reflux with heating for 2 hours. The reaction mixture was concentrated, and then the residue was crystallized from methanol and diethyl ether to obtain the title compound (320 mg, 84%) as white crystals.

$^1$H-NMR (270 MHz, DMSO-$d_6$) δ 0.91 (t, 3H, J=7.0 Hz), 1.69–1.78 (m, 8H), 2.06–2.09 (m, 2H), 2.50 (m, 1H), 3.11–3.21 (m, 2H), 3.91–4.09 (m, 2H), 4.20 (dd, 1H, J=12.2, 6.2 Hz), 4.30 (t, 1H, J=11.2 Hz), 4.73 (m, 1H), 8.44 (brs, 3H).

EXAMPLE 21

2-Cyclopentyl-7,8-dihydro-4-(n-propyl)-8-(1-pyrazolylmethyl)-1H-imidazo[2,1-i]purin-5(4H)-one (Compound 21)

Compound 17 (100 mg, 0.21 mmol) obtained in Example 17 was dissolved in N,N-dimethylformamide (1 mL), to the solution were added pyrazole (28 mg, 0.42 mmol, 2.0 equivalents), and cesium carbonate (137 mg, 0.42 mmol, 2.0 equivalents) and the mixture was stirred at 120° C. for 2 hours. The reaction mixture was partitioned with ethyl acetate and water, and the organic layer was washed with water and dried over anhydrous magnesium sulfate. After the organic layer was concentrated, diethyl ether and hexane were added to the concentrate and the resulting white solid (66 mg) was collected by filtration. The resulting product was dissolved in methanol (1 mL), to the solution were added ammonium formate (132 mg, 2.10 mmol) and 20% palladium hydroxide/carbon (30 mg), and then the mixture was stirred under reflux with heating for 3 hours. The reaction mixture was filtered by using Celite and concentrated, then to the concentrate were added ammonium formate (150 mg) and 20% palladium hydroxide/carbon (50 mg), and the mixture was stirred under reflux with heating for 4 hours. The reaction mixture was filtered by using Celite and concentrated, and the residue was purified by silica gel column chromatography (chloroform:methanol=10:1) to obtain the title compound (40 mg, 52%) as a white solid.

Melting point: 138–140° C. (ethyl acetate)

$^1$H-NMR (270 MHz, CDCl$_3$) δ 0.96 (t, 3H, J=7.6 Hz), 1.68–1.81 (m, 8H), 1.98–2.08 (m, 2H), 3.07 (m, 1H), 3.85 (dd, 1H, J=11.9, 6.2 Hz), 3.97–4.07 (m, 3H), 4.20–4.30 (m, 2H), 4.62 (m, 1H), 6.09 (s, 1H), 7.37 (s, 1H), 7.46 (s, 1H).

IR (CHCl$_3$): 1686, 1655 cm$^{-1}$

FAB-MS: m/z 368 (M$^+$+1).

EXAMPLE 22

2-Cyclopentyl-7,8-dihydro-8-(1-imidazolylmethyl)-4-(n-propyl)-1H-imidazo[2,1-i]purin-5(4H)-one (Compound 22)

In a manner similar to that in Example 21, the title compound (10 mg, 13%) was obtained as a white solid from Compound 17 (100 mg, 0.21 mmol) obtained in Example 17 and imidazole (38 mg, 0.42 mmol, 2.0 equivalents).

Melting point: 158–160° C. (methanol/ethyl acetate)

$^1$H-NMR (270 MHz, CDCl$_3$) δ 0.94 (t, 3H, J=7.6 Hz), 1.68–1.78 (m, 8H), 2.01–2.11 (m, 2H), 3.15 (m, 1H), 3.69 (dd, 1H, J=11.3, 7.0 Hz), 3.94 (t, 2H, J=7.6 Hz), 4.03–4.11 (m, 2H), 4.24 (dd, 1H, J=14.0, 4.1 Hz), 4.52 (m, 1H), 6.98 (s, 1H), 7.02 (s, 1H), 7.76 (s, 1H).

IR (CHCl$_3$): 1686, 1655 cm$^{-1}$

FAB-MS: m/z 368 (M$^+$+1).

EXAMPLE 23

2-Cyclopentyl-7,8-dihydro-4-(n-propyl)-8-(1,2,4-triazol-1-ylmethyl)-1H-imidazo[2,1-i]purin-5(4H)-one (Compound 23)

In a manner similar to that in Example 21, the title compound (70 mg, 46%) was obtained as a white solid from Compound 17 (200 mg, 0.42 mmol) obtained in Example 17 and 1,2,4-triazole (57 mg, 0.83 mmol, 2.0 equivalents).

Melting point: 225–230° C. (ethyl acetate/diethyl ether)

$^1$H-NMR (270 MHz, CDCl$_3$) δ 0.95 (t, 3H, J=7.6 Hz), 1.71–1.82 (m, 8H), 2.04–2.14 (m, 2H), 3.15 (m, 1H), 3.88–3.98 (m, 3H), 4.09 (t, 1H, J=10.0 Hz), 4.38 (t, 2H, J=4.3 Hz), 4.69 (m, 1H), 7.91 (s, 1H), 8.24 (s, 1H).

IR (CHCl$_3$): 1687, 1654, 1649 cm$^{-1}$

FAB-MS: m/z 369 (M$^+$+1).

EXAMPLE 24

2-Cyclopentyl-7,8-dihydro-4-(n-propyl)-8-(1-pyrrolylmethyl)-1H-imidazo[2,1-i]purin-5(4H)-one (Compound 24)

Compound 20 (100 mg, 0.26 mmol) obtained in Example 20 and 2,5-dimethoxytetrahydrofuran (67 µL, 0.51 mmol, 2.0 equivalents) were dissolved in N,N-dimethylformamide (2 mL) and the mixture was stirred at 80° C. for 2 hours. The reaction mixture was partitioned with ethyl acetate and water, and the organic layer was washed with water and dried over anhydrous magnesium sulfate. After the organic layer was concentrated, the residue was purified by silica gel column chromatography (ethyl acetate) to obtain the title compound (56 mg, 60%) as a light yellow solid.

Melting point: 135–140° C. (ethyl acetate)

$^1$H-NMR (270 MHz, CDCl$_3$) δ 0.98 (t, 3H, J=7.6 Hz), 1.65–1.94 (m, 8H), 1.99–2.09 (m, 2H), 3.08 (quin, 1H, J=8.1 Hz), 3.66 (m, 1H), 3.86–4.08 (m, 6H), 6.04 (t, 2H, J=2.2 Hz), 6.61 (t, 2H, J=2.2 Hz)

IR (CHCl$_3$): 1689, 1653 cm$^{-1}$

FAB-MS: m/z 367 (M$^+$+1).

EXAMPLE 25

8-(1-Benzimidazolylmethyl)-2-cyclopentyl-7,8-dihydro-4-(n-propyl)-1H-imidazo[2,1-i]purin-5(4H)-one hydrochloride (Compound 25)

Compound 18 (100 mg, 0.23 mmol) obtained in Example 18 was dissolved in N,N-dimethylformamide (1 mL), to the solution were added benzimidazole (32 mg, 0.27 mmol, 1.2 equivalents) and cesium carbonate (149 mg, 0.46 mmol, 2.0 equivalents), and the mixture was stirred at 120° C. for 4 hours. The reaction mixture was partitioned with ethyl acetate and water, and the resulting organic layer was washed with water and dried over anhydrous magnesium sulfate. The organic layer was concentrated, to the residue was added a 4 mol/L solution of hydrogen chloride in dioxane (2 mL), and then the mixture was stirred at 100° C. for 6 hours. The reaction mixture was concentrated, then the solvent was azeotroped with ethanol, and the residue was crystallized from dichloromethane and diethyl ether to obtain the title compound (40 mg, 42%) as a light yellow solid.

Melting point: 185–190° C. (dichloromethane/ether)

$^1$H-NMR (270 MHz, DMSO-$d_6$) δ 0.97 (t, 3H, J=7.0 Hz), 1.71–1.86 (m, 8H), 2.09–2.19 (m, 2H), 3.28 (m, 1H), 3.31–3.63 (m, 2H), 4.08 (t, 2H, J=7.6 Hz), 4.37 (m, 1H), 4.53 (m, 1H), 5.18 (m, 1H), 7.55–7.66 (m, 2H), 7.80–7.93 (m, 2H), 8.27 (s, 1H).

IR (CHCl$_3$): 1720, 1678, 1589 cm$^{-1}$

FAB-MS: m/z 418 (M$^+$+1).

EXAMPLE 26

8-Chloromethyl-2-cyclopentyl-7,8-dihydro-4-(n-propyl)-1H-imidazo[2,1-i]purin-5(4H)-one hydrochloride (Compound 26)

Compound B1 (799 mg, 2.74 mmol) and dl-serinol (846 mg, 9.30 mmol, 3.4 equivalents) were mixed and stirred at 150° C. for 4 hours. To the reaction mixture were added acetone (50 mL) and methanol (1 mL), and the mixture was stirred. Crystals were collected by filtration and washed with acetone to obtain an adduct (Compound 26a, 764 mg, 84%). To Compound 26a (728 mg, 2.15 mmol) was added thionyl chloride (10 mL) and the mixture was stirred with heating at 60° C. for 3.5 hours. After excess thionyl chloride was evaporated, the residue was neutralized with saturated aqueous sodium hydrogen carbonate and the mixture was extracted with chloroform. The organic layer was washed with saturated aqueous sodium chloride and dried over anhydrous magnesium sulfate, and the solvent was evaporated. The residue was purified by silica gel column chromatography (chloroform:methanol=95:5). To the product was added a 4 mol/L solution of hydrogen chloride in methanol and then the mixture was concentrated. The residue was crystallized from ethyl acetate and hexane to obtain the title compound (703 mg, 98%) as a white solid.

$^1$H-NMR (270 MHz, CDCl$_3$) δ 0.97 (t, 3H, J=7.4 Hz), 1.62–1.91 (m, 8H), 2.00–2.13 (m, 2H), 3.17 (quin, 1H, J=7.9 Hz), 3.57 (dd, 1H, J=11.2, 6.9 Hz), 3.70 (dd, 1H, J=11.2, 4.3 Hz), 4.01 (t, 2H, J=7.3 Hz), 4.03 (dd, 1H, J=11.5, 3.0 Hz), 4.14 (dd, 1H, J=11.5, 9.9 Hz), 4.59 (m, 1H).

EI-MS: m/z 335 (M$^+$).

EXAMPLE 27

2-Cyclopentyl-7,8-dihydro-8-phenylaminomethyl-4-(n-propyl)-1H-imidazo[2,1-i]purin-5(4H)-one dihydrochloride (Compound 27)

To Compound 26 (12 mg, 0.04 mmol) obtained in Example 26 were added water (3 mL), aniline (20 mg, 0.24 mmol, 6.0 equivalents) and sodium hydrogen carbonate (62 mg, 0.74 mmol, 18.5 equivalents), and the mixture was stirred with heating at 70° C. for 2 hours. To the reaction solution was added water, the mixture was extracted with ethyl acetate, and the extract was washed with saturated aqueous sodium chloride, dried over anhydrous magnesium sulfate and concentrated. The residue was purified by silica gel column chromatography (chloroform:methanol=95:5), to the product was added a 4 mol/L solution of hydrogen chloride in ethyl acetate, and then the mixture was concentrated. The residue was crystallized from acetone and methanol to obtain the title compound (3 mg, 19%) as a light yellow solid.

$^1$H-NMR (270 MHz, CDCl$_3$) δ 0.97 (t, 3H, J=7.4 Hz), 1.63–1.87 (m, 8H), 1.99–2.11 (m, 2H), 3.15 (quin, 1H, J=7.9 Hz), 3.24 (dd, 1H, J=12.9, 6.9 Hz), 3.39 (dd, 1H, J=12.9, 4.6 Hz), 3.79 (dd, 1H, J=11.2, 6.9 Hz), 4.01 (t, 2H, J=7.4 Hz), 4.10 (dd, 1H, J=11.2, 9.9 Hz), 4.47 (m, 1H), 6.61 (d, 2H, J=7.9 Hz), 6.71 (t, 1H, J=7.3 Hz), 7.13 (t, 2H, J=7.6 Hz).

EI-MS: m/z 392 (M$^+$).

EXAMPLE 28

2-Cyclopentyl-7,8-dihydro-8-piperidinomethyl-4-(n-propyl)-1H-imidazo[2,1-i]purin-5(4H)-one dihydrochloride (Compound 28)

Compound 26 (49 mg, 0.14 mmol) obtained in Example 26 was dissolved in dimethyl sulfoxide (5 mL), to the solution was added piperidine (100 μL, 1.01 mmol, 7.2 equivalents), and the mixture was stirred with heating at 80° C. for 3.5 hours. To the reaction solution was added water, the mixture was extracted with ethyl acetate, and the extract was washed with saturated aqueous sodium chloride, dried over anhydrous sodium sulfate and concentrated. The residue was purified by silica gel column chromatography (chloroform:methanol=95:5), to the product was added a 4 mol/L solution of hydrogen chloride in ethyl acetate, then the mixture was concentrated. The residue was crystallized from acetone to obtain the title compound (31 mg, 48%) as a white solid.

Melting point: 250–255° C. (acetone)

$^1$H-NMR (270 MHz, CDCl$_3$) δ 0.97 (t, 3H, J=7.3 Hz), 1.20–1.30 (m, 2H), 1.35–1.62 (m, 4H), 1.65–1.72 (m, 2H), 1.75–1.92 (m, 6H), 1.99–2.08 (m, 2H), 2.43 (br, 5H), 2.54 (dd, 1H, J=12.5, 6.9 Hz), 3.17 (quin, 1H, J=7.6 Hz), 3.89 (dd, 1H, J=11.3, 6.3 Hz), 4.06 (t, 2H, J=7.5 Hz), 4.15 (dd, 1H, J=11.2, 9.6 Hz), 4.39 (dq, 1H, J=9.6, 6.6 Hz).

IR (KBr): 1716, 1707, 1701, 1684, 1676, 1655, 1589 cm$^{-1}$

EI-MS: m/z 384 (M$^+$).

EXAMPLE 29

2-Cyclopentyl-7,8-dihydro-4-(n-propyl)-8-(1-pyrrolidinylmethyl)-1H-imidazo[2,1-i]purin-5(4H)-one dihydrochloride (Compound 29)

In a manner similar to that in Example 28, the title compound in the free form was obtained from Compound 26

(50 mg, 0.16 mmol) obtained in Example 26 and pyrrolidine (100 µL, 1.20 mmol, 7.5 equivalents), and then to the resulting product was added a 4 mol/L solution of hydrogen chloride in ethyl acetate. The reaction mixture was concentrated, and the residue was crystallized from acetone to obtain the title compound (24 mg, 34%) as a white solid.

$^1$H-NMR (270 MHz, CDCl$_3$) δ 0.97 (t, 3H, J=7.4 Hz), 1.60–1.94 (m, 12H), 2.00–2.08 (m, 2H), 2.56 (br, 5H), 2.74 (dd, 1H, J=12.2, 6.9 Hz), 3.18 (quin, 1H, J=7.6 Hz), 3.90 (dd, 1H, J=11.2, 6.6 Hz), 4.05 (t, 2H, J=7.4 Hz), 4.16 (t, 1H, J=10.3 Hz), 4.36 (dq, 1H, J=6.6, 3.0 Hz).

EI-MS: m/z 370 (M$^+$).

EXAMPLE 30

2-Cyclopentyl-7,8-dihydro-8-morpholinomethyl-4-(n-propyl)-1H-imidazo[2,1-i]purin-5(4H)-one dihydrochloride (Compound 30)

In a manner similar to that in Example 28, the title compound in the free form was obtained from Compound 26 (50 mg, 0.16 mmol) obtained in Example 26 and morpholine (100 µL, 1.14 mmol, 7.1 equivalents), and then to the resulting product was added a 4 mol/L solution of hydrogen chloride in ethyl acetate. The mixture was concentrated and the residue was crystallized from acetone to obtain the title compound (21 mg, 29%) as a light yellow solid.

$^1$H-NMR (270 MHz, CDCl$_3$) δ 0.97 (t, 3H, J=7.4 Hz), 1.61–1.91 (m, 8H), 2.00–2.12 (m, 2H), 2.45 (dd, 1H, J=12.9, 7.3 Hz), 2.53 (br, 4H), 2.62 (dd, 1H, J=12.9, 7.3 Hz), 3.17 (quin, 1H, J=7.6 Hz), 3.70 (br, 4H), 3.88 (dd, 1H, J=11.2, 6.6 Hz), 4.02 (t, 2H, J=7.5 Hz), 4.11 (dd, 1H, J=11.2, 9.9 Hz), 4.40 (dq, 1H, J=9.6, 6.9 Hz).

EI-MS: m/z 386 (M$^+$).

EXAMPLE 31

8-(4-Benzyl-1-piperazinylmethyl)-2-cyclopentyl-7,8-dihydro-4-(n-propyl)-1H-imidazo[2,1-i]purin-5(4H)-one trihydrochloride (Compound 31)

In a manner similar to that in Example 28, the title compound in the free form was obtained from Compound 26 (54 mg, 0.16 mmol) obtained in Example 26 and 1-benzylpiperazine (100 µL, 0.58 mmol, 3.6 equivalents), and then to the resulting product was added a 4 mol/L solution of hydrogen chloride in ethyl acetate. The mixture was concentrated and the residue was crystallized from acetone to obtain the title compound (21 mg, 23%) as a white solid.

$^1$H-NMR (270 MHz, CDCl$_3$) δ 0.97 (t, 3H, J=7.3 Hz), 1.59–1.93 (m, 8H), 2.02–2.13 (m, 2H), 2.40–2.69 (m, 10H), 3.19 (quin, 1H, J=7.8 Hz), 3.49 (s, 2H), 3.88 (dd, 1H, J=11.3, 6.3 Hz), 4.05 (t, 2H, J=7.3 Hz), 4.14 (dd, 1H, J=11.3, 9.9 Hz), 4.39 (m, 1H), 7.24–7.39 (m, 5H).

EI-MS: m/z 475 (M$^+$).

EXAMPLE 32

2-Cyclopentyl-7,8-dihydro-8-(4-phenyl-1-piperazinylmethyl)-4-(n-propyl)-1H-imidazo[2,1-i]purin-5(4H)-one trihydrochloride (Compound 32)

In a manner similar to that in Example 28, the title compound in the free form was obtained from Compound 26 (53 mg, 0.16 mmol) obtained in Example 26 and 1-phenylpiperazine (100 µL, 0.65 mmol, 4.1 equivalents), and to the resulting product was added a 4 mol/L solution of hydrogen chloride in ethyl acetate. The mixture was concentrated and the residue was crystallized from methanol and acetone to obtain the title compound (33 mg, 37%) as a white solid.

Melting point: 190–195° C. (methanol/acetone)

$^1$H-NMR (270 MHz, CDCl$_3$) δ 0.97 (t, 3H, J=7.4 Hz), 1.58–1.89 (m, 8H), 1.99–2.09 (m, 2H), 2.51 (dd, 1H, J=12.9, 6.9 Hz), 2.66 (dd, 1H, J=12.9, 5.9 Hz), 2.55–2.75 (m, 4H), 3.18 (br, 5H), 3.91 (dd, 1H, J=12.2, 6.3 Hz), 4.03 (t, 2H, J=7.4 Hz), 4.14 (dd, 1H, J=12.2, 9.9 Hz), 4.43 (m, 1H), 6.85 (d, 1H, J=7.3 Hz), 6.91 (d, 2H, J=8.8 Hz), 7.27 (dd, 2H, J=8.8, 7.3 Hz).

IR (KBr): 1722, 1709, 1693, 1664, 1587, 1558, 1508 cm$^{-1}$

EI-MS: m/z 461 (M$^+$).

Elemental Analysis for C$_{26}$H$_{35}$N$_7$O.3.0 HCl.1.0 H$_2$O.0.1C$_3$H$_6$O

Calculated (%): C, 53.11; H, 6.88; N, 16.48. Found (%): C, 53.08; H, 6.95; N, 16.52.

EXAMPLE 33

8-(4-Benzylpiperidinomethyl)-2-cyclopentyl-7,8-dihydro-4-(n-propyl)-1H-imidazo[2,1-i]purin-5(4H)-one dihydrochloride (Compound 33)

In a manner similar to that in Example 28, the title compound in the free form was obtained from Compound 26 (53 mg, 0.16 mmol) obtained in Example 26 and 4-benzylpiperidine (100 µL, 0.59 mmol, 3.7 equivalents), and then to the resulting product was added a 4 mol/L solution of hydrogen chloride in ethyl acetate. The mixture was concentrated and the residue was crystallized from acetone to obtain the title compound (41 mg, 48%) as a white solid.

$^1$H-NMR (270 MHz, CDCl$_3$) δ 0.96 (t, 3H, J=7.4 Hz), 1.25 (m, 2H), 1.40–2.15 (m, 14H), 2.40 (dd, 1H, J=11.5, 6.9 Hz), 2.51 (d, 2H, J=6.6 Hz), 2.56 (dd, 1H, J=11.5, 7.4 Hz), 2.85 (d, 2H, J=11.2 Hz), 3.18 (quin, 1H, J=8.2 Hz), 3.87 (dd, 1H, J=11.2, 6.2 Hz), 4.05 (t, 2H, J=7.6 Hz), 4.12 (dd, 1H, J=11.2, 9.5 Hz), 4.36 (quin, 1H, J=6.6 Hz), 7.13 (d, 2H, J=8.2 Hz), 7.20–7.34 (m, 3H).

EI-MS: m/z 474 (M$^+$).

EXAMPLE 34

8-Benzylaminomethyl-2-cyclopentyl-7,8-dihydro-4-(n-propyl)-1H-imidazo[2,1-i]purin-5(4H)-one dihydrochloride (Compound 34)

In a manner similar to that in Example 28, the title compound in the free form was obtained from Compound 26 (40 mg, 0.12 mmol) obtained in Example 26 and benzylamine (100 µL, 0.91 mmol, 7.6 equivalents), and then to the resulting product was added a 4 mol/L solution of hydrogen chloride in ethyl acetate. The mixture was concentrated and the residue was crystallized from acetone to obtain the title compound (9 mg, 16%) as a white solid.

Melting point: 225–235° C. (acetone)

$^1$H-NMR (270 MHz, CDCl$_3$) δ 0.96 (t, 3H, J=7.4 Hz), 1.57–1.91 (m, 8H), 1.97–2.12 (m, 2H), 2.74 (dd, 1H, J=12.1, 6.9 Hz), 2.86 (dd, 1H, J=12.1, 4.9 Hz), 3.15 (quin, 1H, J=7.3 Hz), 3.79 (dd, 1H, J=10.8, 3.3 Hz), 3.82 (d, 2H, J=4.6 Hz), 4.00 (t, 2H, J=7.6 Hz), 4.06 (dd, 1H, J=10.8, 9.9 Hz), 4.37 (m, 1H), 7.21 (m, 5H).

IR (KBr): 1718, 1674, 1655, 1516, 1508, 1458, 1394, 1363 cm$^{-1}$

EI-MS: m/z 406 (M$^+$).

EXAMPLE 35

(R)-1,8-Dibenzyl-2-bromo-7,8-dihydro-4-(n-propyl)-1H-imidazo[2,1-i]purin-5(4H)-one (Compound 35)

To Compound 13a (6.65 g, 21.2 mmol) obtained in Example 13 was added (R)-phenylalaminol (4.80 g, 31.7 mmol, 1.5 equivalents) and the mixture was stirred with heating at 150° C. for 4 hours. The reaction mixture was directly purified by silica gel column chromatography (chloroform:methanol=100:1 to 100:3) to obtain an adduct (2.66 g, 30%). To the resulting adduct (2.66 g, 6.37 mmol) was added thionyl chloride (5 mL) and the mixture was stirred with heating at 60° C. for 2.5 hours. After the thionyl chloride was evaporated, the residue was neutralized with saturated aqueous sodium hydrogen carbonate and the mixture was extracted with chloroform. The organic layer was washed with saturated aqueous sodium chloride and dried over anhydrous sodium sulfate, and the solvent was evaporated. The residue was purified by silica gel column chromatography (chloroform:methanol=100:1) to obtain (R)-1,8-dibenzyl-7,8-dihydro-4-(n-propyl)-1Himidazo[2,1-i]purin-5(4H)-one (Compound 35a, 1.75 g, 69%). Compound 35a (1.75 g, 4.38 mmol) was dissolved in tetrahydrofuran (30 mL), to the solution was added a 1.54 mol/L solution of lithium diisopropylamide (4.38 mL, 6.75 mmol, 1.5 equivalents) in cyclohexane at −78° C., and the mixture was stirred for 1 hour. To the reaction solution was added a solution (10 mL) of carbon tetrabromide (2.18 g, 6.65 mmol, 1.5 equivalents) in tetrahydrofuran, and the mixture was stirred at −78° C. for 1 hour, then warmed to room temperature and stirred for 2 hours. To the reaction solution was added saturated aqueous ammonium chloride and the mixture was extracted with ethyl acetate. The organic layer was washed with saturated aqueous sodium chloride and dried over anhydrous sodium sulfate, and the solvent was evaporated. The residue was purified by silica gel column chromatography (chloroform:methanol=99.5:0.5), the eluent was concentrated, and to the residue were added acetone and diethyl ether. The deposited crystals were collected by filtration and dried under reduced pressure to obtain the title compound (1.51 g, 72%) as white crystals.

Melting point: 200–206° C. (acetone/diethyl ether)

$^1$H-NMR (270 MHz, CDCl$_3$) δ 0.94 (t, 3H, J=7.6 Hz), 1.72 (q, 2H, J=7.6 Hz), 2.75 (dd, 1H, J=13.6, 8.3 Hz), 3.10 (dd, 1H, J=13.6, 5.7 Hz), 3.64 (dd, 1H, J=11.2, 6.9 Hz), 3.84 (dd, 1H, J=11.2, 9.9 Hz), 3.88 (t, 2H, J=7.6 Hz), 4.55 (m, 1H), 5.46 (d, 1H, J=15.2 Hz), 5.53 (d, 1H, J=15.2 Hz), 7.17–7.30 (m, 6H), 7.33–7.42 (m, 4H).

IR (KBr): 1693, 1682, 1666, 1655, 1587, 1520, 1441, 1367 cm$^{-1}$

EI-MS: m/z 478 (M$^+$+1).

Elemental Analysis for C$_{24}$H$_{24}$BrN$_5$O.0.3H$_2$O

Calculated (%): C, 59.58; H, 5.12; N, 14.48. Found (%): C, 59.59; H, 4.98; N, 14.21.

EXAMPLE 36

(R)-8-Benzyl-7,8-dihydro-1-methoxymethyl-2-methylthio-4-(n-propyl)-1H-imidazo[2,1-i]purin-5(4H)-one (Compound 36)

6-Methylthio-3-(n-propyl)-7H-purin-2(3H)-one (Compound B8, 11.8 g, 52.5 mmol), which was obtained by the method described in Journal of Heterocyclic Chemistry (J. Heterocycl. Chem.), 30, p. 241, 1993, was dissolved in N,N-dimethylformamide (200 mL). To the solution was added sodium hydride (1.51 g, 63.0 mmol, 1.2 equivalents) and the mixture was stirred at room temperature for 30 minutes. To the reaction solution was added chloromethyl methyl ether (4.85 mL, 63.9 mmol, 1.2 equivalents) and the mixture was stirred at room temperature for 1 hour. To the reaction solution was added saturated aqueous ammonium chloride, the mixture was extracted with chloroform, and the organic layer was washed with saturated aqueous sodium chloride and dried over anhydrous sodium sulfate. Then, the solvent was evaporated, and to the resulting residue was added diethyl ether. The deposited crystals were collected by filtration to obtain a methoxymethyl adduct. (R)-8-Benzyl-2-bromo-7,8-dihydro-1-methoxymethyl-4-(n-propyl)-1H-imidazo[2,1-i]purin-5(4H)-one (Compound 36a, 2.81 g, 6.52 mmol), which was obtained from the methoxymethyl adduct in a manner similar to that in Example 35, was dissolved in N,N-dimethylformamide (26 mL), to the solution was added an about 15% aqueous solution of methylmercaptan sodium salt (6.10 mL, 13.1 mmol, 2.0 equivalents), and the mixture was stirred at room temperature for three days. To the reaction solution was added water, the mixture was extracted with chloroform, then the organic layer was washed with saturated aqueous sodium chloride and dried over anhydrous sodium sulfate, and the solvent was evaporated. The reaction residue was purified by silica gel column chromatography (chloroform:methanol=98:2) and the eluent was concentrated. To the residue was added acetonitrile, and the deposited crystals were collected by filtration to obtain the title compound (2.17 g, 84%) as white crystals.

Melting point: 110–112° C. (acetonitrile)

$^1$H-NMR (270 MHz, CDCl$_3$) δ 0.94 (t, 3H, J=7.3 Hz), 1.74 (q, 2H, J=7.3 Hz), 2.68 (s, 3H), 2.71 (dd, 1H, J=13.6, 8.6 Hz), 3.14 (dd, 1H, J=13.6, 5.3 Hz), 3.43 (s, 3H), 3.64 (dd, 1H, J=11.2, 6.9 Hz), 3.81 (dd, 1H, J=11.2, 9.9 Hz), 3.93 (t, 2H, J=7.3 Hz), 4.55 (m, 1H), 5.53 (d, 1H, J=10.6 Hz), 5.60 (d, 1H, J=10.6 Hz), 7.18–7.31 (m, 5H).

IR (KBr): 1714, 1693, 1648, 1560, 1541, 1516, 1389, 1320, 1122 cm$^{-1}$

EI-MS: m/z 400 (M$^+$+1).

Elemental Analysis for C$_{20}$H$_{25}$N$_5$O$_2$S

Calculated (%): C, 60.13; H, 6.31; N, 17.53. Found (%): C, 59.95; H, 6.38; N, 17.44.

EXAMPLE 37

(R)-1,8-Dibenzyl-7,8-dihydro-4-(n-propyl)-2-(1-pyrrolidinyl)imidazo-[2,1-i]purin-5(4H)-one (Compound 37)

Compound 35 (500 mg, 1.05 mmol) obtained in Example 35 was dissolved in N,N-dimethylformamide (15 mL), to the solution were added potassium carbonate (430 mg, 3.11 mmol, 3.0 equivalents) and pyrrolidine (260 μL, 3.11 mmol, 3.0 equivalents), and then the mixture was stirred with heating at 100° C. for 3.5 hours. To the reaction solution was added water, the mixture was extracted with ethyl acetate, and the extract was washed with saturated aqueous sodium chloride, dried over anhydrous sodium sulfate and concentrated. The residue was purified by silica gel column chromatography (chloroform:methanol=99:1 to 97:3), and to the residue were added acetone and diethyl ether. The deposited crystals were collected by filtration to obtain the title compound (467 mg, 95%) as white crystals.

Melting point: 124–125° C. (acetone/diethyl ether)

$^1$H-NMR (270 MHz, CDCl$_3$) δ 0.94 (t, 3H, J=7.3 Hz), 1.74 (q, 2H, J=7.3 Hz), 1.87 (quin, 4H, J=3.3 Hz), 2.66 (dd, 1H, J=13.6, 8.3 Hz), 3.04 (dd, 1H, J=13.6, 5.3 Hz), 3.46 (t, 4H, J=6.6 Hz), 3.60 (dd, 1H, J=10.9, 6.6 Hz), 3.76 (dd, 1H, J=10.9, 9.9 Hz), 3.88 (t, 2H, J=7.3 Hz), 4.46 (m, 1H), 5.45 (d, 1H, J=16.8 Hz), 5.57 (d, 1H, J=16.8 Hz), 7.10–7.36 (m, 10H).

IR (KBr): 1687, 1660, 1604, 1549, 1510, 1491, 1454, 1404, 1354, 1259 cm$^{-1}$

EI-MS: m/z 469 (M$^+$+1).

Elemental Analysis for $C_{28}H_{32}N_6O \cdot 0.3H_2O$

Calculated (%): C, 70.95; H, 6.93; N, 17.73. Found (%): C, 70.97; H, 7.07; N, 17.81.

EXAMPLE 38

(R)-8-Benzyl-7,8-dihydro-4-(n-propyl)-2-(1-pyrrolidinyl)-1H-imidazo[2,1-i]purin-5(4H)-one hydrochloride (Compound 38)

Compound 37 (329 mg, 7.03 mmol) obtained in Example 37 was dissolved in methanol (5 mL), to the solution were added ammonium formate (950 mg, 15.0 mmol, 2.0 equivalents) and 20% palladium hydroxide/carbon (50 mg), and then the mixture was stirred under reflux with heating for 3 hours. The reaction mixture was filtered by using Celite and then concentrated, and the residue was purified by silica gel column chromatography (chloroform:methanol=90:10). The solvent was evaporated, then to the residue were added a 4 mol/L solution (4 mL) of hydrogen chloride in dioxane and methanol (4 mL), and the mixture was concentrated. The residue was crystallized from acetone and diethyl ether to obtain the title compound (75 mg, 28%) as white crystals.

Melting point: 248–250° C. (acetone/diethyl ether)

$^1$H-NMR (270 MHz, CDCl$_3$) δ 0.94 (t, 3H, J=7.3 Hz), 1.75 (q, 2H, J=7.3 Hz), 2.03–2.08 (m, 4H), 2.94 (dd, 1H, J=13.8, 7.9 Hz), 3.19 (dd, 1H, J=13.8, 4.6 Hz), 3.63 (t, 4H, J=6.6 Hz), 3.99 (dd, 1H, J=11.5, 6.9 Hz), 4.00 (t, 2H, J=7.3 Hz), 4.12 (dd, 1H, J=11.5, 9.2 Hz), 4.57 (m, 1H), 7.24–7.36 (m, 5H), 9.88 (brs, 1H).

IR (KBr): 1714, 1680, 1628, 1568, 1518, 1458, 1441, 1396, 1348, 1300 cm$^{-1}$

EI-MS: m/z 379 (M$^+$+1).

Elemental Analysis for $C_{21}H_{26}N_6O \cdot HCl \cdot 0.3H_2O$

Calculated (%): C, 60.01; H, 6.62; N, 19.99. Found (%): C, 60.07; H, 6.73; N, 20.09.

EXAMPLE 39

(R)-8-Benzyl-7,8-dihydro-2-morpholino-4-(n-propyl)-1H-imidazo[2,1-i]purin-5(4H)-one (Compound 39)

In a manner similar to that in Example 37, an adduct was obtained from Compound 36a (100 mg, 0.23 mmol) obtained in Example 36 and morpholine (120 μL, 1.38 mmol, 6.0 equivalents). To the resulting adduct were added a 4 mol/L solution (5 mL) of hydrogen chloride in dioxane and methanol (5 mL), and then the mixture was stirred under reflux with heating for 2 hours. The reaction mixture was concentrated, and the residue was crystallized from acetone and diethyl ether to obtain the title compound (33 mg, 32%) as white crystals.

$^1$H-NMR (270 MHz, CDCl$_3$) δ 0.94 (t, 3H, J=7.3 Hz), 1.74 (q, 2H, J=7.3 Hz), 2.94 (dd, 1H, J=13.8, 7.9 Hz), 3.18 (dd, 1H, J=13.8, 4.6 Hz), 3.62 (m, 4H), 3.79 (m, 4H), 3.97 (dd, 1H, J=11.6, 6.6 Hz), 3.98 (t, 2H, J=7.4 Hz), 4.11 (dd, 1H, J=11.6, 9.3 Hz), 4.56 (m, 1H), 7.18–7.34 (m, 5H), 9.87 (brs, 1H).

EI-MS: m/z 394 (M$^+$).

EXAMPLE 40

(R)-8-Benzyl-7,8-dihydro-2-(1-hydroxycyclopentyl)-4-(n-propyl)-1H-imidazo[2,1-i]purin-5(4H)-one (Compound 40)

Compound 35a (9.28 g, 24.1 mmol) obtained in Example 35 was dissolved in tetrahydrofuran (200 mL), to the solution was added a 1.48 mol/L solution of lithium diisopropylamide (73.0 mL, 34.8 mmol, 1.5 equivalents) in cyclohexane at −78° C., and the mixture was stirred for 1 hour. To the reaction solution was added a solution (20 mL) of cyclopentanone (3.80 g, 45.2 mmol, 1.9 equivalents) in tetrahydrofuran, and the mixture was stirred at −78° C. for 1 hour, then warmed to room temperature and stirred for 20 hours. To the reaction solution was added saturated aqueous ammonium chloride and the mixture was extracted with ethyl acetate. The extract was washed with saturated aqueous sodium chloride and dried over anhydrous sodium sulfate, and the solvent was evaporated. The residue was purified by silica gel column chromatography (ethyl acetate) to obtain an adduct (3.32 g, 30%). The resulting adduct, i.e., Adduct 40a (3.04 g, 6.29 mmol), was dissolved in methanol (100 mL), to the solution were added ammonium formate (1.18 g, 18.7 mmol, 3.0 equivalents) and 20% palladium hydroxide/carbon (600 mg), and the mixture was stirred under reflux with heating for 3 hours. The reaction mixture was filtered by using Celite and concentrated, and the residue was purified by silica gel column chromatography (chloroform:methanol=99:1). After the solvent was evaporated, the residue was crystallized from ethyl acetate to obtain the title compound (2.22 g, 90%) as white crystals.

Melting point: 110–115° C. (ethyl acetate)

$^1$H-NMR (270 MHz, CDCl$_3$) δ 0.97 (t, 3H, J=7.4 Hz), 1.73–2.04 (m, 8H), 2.15–2.36 (m, 2H), 2.80 (dd, 1H, J=13.4, 6.3 Hz), 2.88 (dd, 1H, J=13.4, 7.1 Hz), 3.73 (dd, 1H, J=10.4, 6.0 Hz), 3.93–4.16 (m, 4H), 7.10–7.29 (m, 5H).

IR (KBr): 1695, 1653, 1541, 1497, 1454, 1265 cm$^{-1}$

EI-MS: m/z 394 (M$^+$+1).

Elemental Analysis for $C_{22}H_{27}N_5O_2 \cdot 0.1H_2O$

Calculated (%): C, 66.85; H, 6.94; N, 17.72. Found (%): C, 66.83; H, 7.23; N, 17.54.

EXAMPLE 41

(R)-1,8-Dibenzyl-2-formyl-7,8-dihydro-4-(n-propyl)-1H-imidazo[2,1-i]purin-5(4H)-one (Compound 41)

Compound 35a (3.45 g, 8.96 mmol) obtained in Example 35 was dissolved in tetrahydrofuran (100 mL), to the solution was added a 1.50 mol/L solution (9.0 mL) of lithium diisopropylamide (13.5 mmol, 1.5 equivalents) in cyclohexane at −78° C., and the mixture was stirred for 1 hour. To the reaction solution was added a solution (10 mL) of N,N-dimethylformamide (2.83 g, 38.7 mmol, 4.3 equivalents) in tetrahydrofuran, and the mixture was stirred at −78° C. for 1 hour, then warmed to room temperature and stirred for 1 hour. To the reaction solution was added saturated aqueous ammonium chloride and the mixture was extracted with ethyl acetate. The organic layer was washed with saturated aqueous sodium chloride and dried over anhydrous sodium sulfate, and the solvent was evaporated. The residue was purified by silica gel column chromatography (ethyl acetate: n-hexane=33:67 to 50:50). To the residue was added ethyl acetate, and the deposited crystals were collected by filtration to obtain the title compound (3.31 g, 89%) as white crystals.

Melting point: 184–185° C. (ethyl acetate)

$^1$H-NMR (270 MHz, CDCl$_3$) δ 0.96 (t, 3H, J=7.6 Hz), 1.75 (q, 2H, J=7.6 Hz), 2.79 (dd, 1H, J=13.5, 7.9 Hz), 3.15 (dd, 1H, J=13.5, 5.6 Hz), 3.67 (dd, 1H, J=11.3, 7.3 Hz), 3.84–3.96 (m, 3H), 4.64 (m, 1H), 5.91 (d, 1H, J=14.2 Hz), 6.01 (d, 1H, J=14.2 Hz), 7.18–7.46 (m, 10H), 9.81 (s, 1H).

IR (KBr): 1718, 1703, 1693, 1660, 1649, 1572, 1560, 1543, 1467, 1344 cm$^{-1}$

EI-MS: m/z 428 (M$^+$+1).

Elemental Analysis for C$_{25}$H$_{25}$N$_5$O$_2$.0.4H$_2$O

Calculated (%): C, 69.07; H, 5.98; N, 16.11. Found (%): C, 69.09; H, 5.89; N, 15.94.

EXAMPLE 42

(R)-1,8-Dibenzyl-2-chloromethyl-7,8-dihydro-4-(n-propyl)-1H-imidazo[2,1-i]purin-5(4H)-one (Compound 42)

Compound 41 (2.71 g, 6.55 mmol) obtained in Example 41 was dissolved in dichloromethane (25 mL) and ethanol (50 mL), to the solution was added sodium borohydride (2.48 g, 65.6 mmol, 1.0 equivalent), and the mixture was stirred at room temperature for 3 hours. To the reaction solution was added saturated aqueous ammonium chloride and the mixture was extracted with chloroform. The organic layer was washed with saturated aqueous sodium chloride and dried, and then the solvent was evaporated to obtain an alcohol compound (1.76 g). To the alcohol compound was added thionyl chloride (10.0 mL, 51.5 mmol) and the mixture was stirred at 60° C. for 2 hours. The reaction solution was concentrated, then to the residue was added saturated aqueous sodium hydrogen carbonate, and the mixture was extracted with chloroform. The organic layer was washed with saturated aqueous sodium chloride and dried over anhydrous sodium sulfate, and then the solvent was evaporated. The residue was purified by silica gel column chromatography (chloroform:methanol=99.5:0.5), and to the residue was added acetone and diethyl ether. The deposited crystals were collected by filtration to obtain the title compound (1.45 g, 49%) as white crystals.

Melting point: 112–113° C. (acetone/diethyl ether)

$^1$H-NMR (270 MHz, CDCl$_3$) δ 0.96 (t, 3H, J=7.3 Hz), 1.74 (q, 2H, J=7.3 Hz), 2.73 (dd, 1H, J=13.5, 8.2 Hz), 3.10 (dd, 1H, J=13.5, 5.3 Hz), 3.66 (dd, 1H, J=10.9, 6.6 Hz), 3.84 (dd, 1H, J=10.9, 9.9 Hz), 3.90 (t, 2H, J=7.3 Hz), 4.47 (s, 2H), 4.56 (m, 1H), 5.64 (d, 1H, J=15.8 Hz), 5.68 (d, 1H, J=15.8 Hz), 7.16–7.41 (m, 10H).

IR (KBr): 1684, 1672, 1581, 1525, 1454, 1425, 1392, 1336, 1265, 743 cm$^{-1}$

EI-MS: m/z 447 (M$^+$).

Elemental Analysis for C$_{25}$H$_{26}$ClN$_5$O.0.2H$_2$O

Calculated (%): C, 66.50; H, 5.89; N, 15.51. Found (%): C, 66.51; H, 5.84; N, 15.39.

EXAMPLE 43

(R)-8-Benzyl-2-dimethylaminomethyl-7,8-dihydro-4-(n-propyl)-1H-imidazo[2,1-i]purin-5(4H)-one (Compound 43)

Compound 42 (60 mg, 0.134 mmol) obtained in Example 42 was dissolved in tetrahydrofuran (3 mL), to the solution was added a 2 mol/L solution of dimethylamine (200 μL, 0.401 mmol, 3.1 equivalents) in tetrahydrofuran, and the mixture was stirred with heating at 70° C. for 5.5 hours. The reaction solution was concentrated and then directly purified by silica gel column chromatography (chloroform:methanol=99:1 to 97:3), and the title compound (7 mg, 19%) was obtained in a manner similar to the method by which Compound 40 was obtained from Adduct 40a in Example 40.

$^1$H-NMR (270 MHz, CDCl$_3$) δ 0.98 (t, 3H, J=7.3 Hz), 1.81 (q, 2H, J=7.3 Hz), 2.30 (s, 6H), 2.87–2.91 (m, 2H), 3.57 (d, 1H, J=14.2 Hz), 3.64 (d, 1H, J=14.2 Hz), 3.79 (dd, 1H, J=13.3, 6.6 Hz), 4.02 (dd, 1H, J=13.9, 9.9 Hz), 4.06 (t, 2H, J=7.3 Hz), 4.17 (m, 1H), 7.12–7.20 (m, 5H).

EI-MS: m/z 366 (M$^+$).

EXAMPLE 44

(R)-8-Benzyl-7,8-dihydro-2-piperidinomethyl-4-(n-propyl)-1H-imidazo[2,1-i]purin-5(4H)-one (Compound 44)

In a manner similar to that in Example 43, the title compound (18 mg, 33%) was obtained from Compound 42 (60 mg, 0.134 mmol) obtained in Example 42 and piperidine (100 μL, 1.01 mmol, 7.8 equivalents).

$^1$H-NMR (270 MHz, CDCl$_3$) δ 0.96 (t, 3H, J=7.3 Hz), 1.42–1.55 (m, 2H), 1.62–1.70 (m, 4H), 1.82 (q, 2H, J=7.3 Hz), 2.55–2.57 (m, 4H), 2.92 (dd, 1H, J=13.6, 6.6 Hz), 3.08 (dd, 1H, J=13.6, 7.0 Hz), 3.73 (s, 2H), 3.88 (dd, 1H, J=13.6, 7.0 Hz), 4.02–4.13 (m, 3H), 4.43 (m, 1H), 7.19–7.32 (m, 5H).

EI-MS: m/z 406 (M$^+$).

EXAMPLE 45

(R)-8-Benzyl-2-ethoxymethyl-7,8-dihydro-4-(n-propyl)-1H-imidazo[2,1-i]purin-5(4H)-one 0.5 fumarate (Compound 45)

Compound B12 (20.0 g, 70.8 mmol) obtained in Reference Example 22 and (R)-phenylalaminol (16.1 g, 106 mmol, 1.5 equivalents) were stirred at 150° C. for 5 hours. The resulting reaction mixture was directly purified by silica gel column chromatography (chloroform:methanol=99:1 to 95:5) to obtain an adduct (27.1 g, 99%). To the resulting adduct (27.1 g, 70.3 mmol) was added thionyl chloride (50 mL, 685 mmol, 9.7 equivalents) and the mixture was stirred at 60° C. for 1 hour. Excess thionyl chloride was evaporated, to the resulting residue were added chloroform and saturated aqueous sodium hydrogen carbonate, and then the mixture was stirred at room temperature for 1 hour. The reaction mixture was extracted with chloroform, then the organic layer was washed with saturated aqueous sodium chloride and dried over anhydrous sodium sulfate, and the solvent was evaporated. The residue was purified by silica gel column chromatography (chloroform:methanol=99.5:0.5) to obtain the title compound in the free form (Compound 45a, 22.8 g, 88%). To a solution of Compound 45a (22.8 g, 61.9 mmol) in methanol (100 mL) was added fumaric acid (3.47 g, 29.9 mmol, 0.5 equivalent), and the solvent was evaporated. To the residue were added acetone and diethyl ether, and the deposited crystals were collected by filtration to obtain the title compound (18.0 g, 60%) as white crystals.

Further, the title compound in the free form (Compound 45a) was also obtained by the following method. Compound 42 (60 mg, 0.134 mmol) obtained in Example 42 was dissolved in ethanol (2 mL), to the solution was added a 21% solution of sodium ethoxide (100 μL, 0.312 mmol, 2.4 equivalents) in ethanol, and the mixture was stirred with heating at 70° C. for 3 hours. The reaction solution was concentrated and then directly purified by silica gel column chromatography (chloroform:methanol=99:1 to 97:3). Then the title compound in the free form (Compound 45a, 18 mg, 36%) was obtained in a manner similar to the method by which Compound 40 was obtained from Adduct 40a in Example 40.

Melting point: 168–170° C. (acetone/diethyl ether)
$^1$H-NMR (270 MHz, CDCl$_3$) δ 0.96 (t, 3H, J=7.3 Hz), 1.33 (t, 3H, J=6.9 Hz), 1.78 (q, 2H, J=7.3 Hz), 3.00 (dd, 1H, J=13.8, 7.9 Hz), 3.21 (dd, 1H, J=13.8, 4.9 Hz), 3.69 (q, 2H, J=6.9 Hz), 4.03 (dd, 1H, J=11.9, 6.6 Hz), 4.06 (t, 2H, J=6.6 Hz), 4.18 (dd, 1H, J=11.9, 9.6 Hz), 4.69 (s, 2H), 4.70 (m, 1H), 6.88 (s, 2H), 7.18–7.36 (m, 5H), 8.48 (br, 1H).
IR (KBr) 1708, 1691, 1637, 1541, 1456, 1379, 1299 cm$^{-1}$
EI-MS: m/z 368 (M$^+$+1).
Elemental Analysis for C$_{20}$H$_{25}$N$_5$O$_2$·0.5C$_4$H$_4$O$_4$·0.1H$_2$O
Calculated (%): C, 61.84; H, 6.42; N, 16.39. Found (%): C, 61.92; H, 6.49; N, 16.53.

EXAMPLE 46

(R)-8-Benzyl-2-[(4R,5R)-dimethyl-1,3-dioxacyclopentan-2-yl]-7,8-dihydro-4-(n-propyl)-1H-imidazo[2,1-i]purin-5(4H)-one (Compound 46)

Compound 41 (150 mg, 0.351 mmol) obtained in Example 41 was dissolved in toluene (25 mL), to the solution were added (2R,3R)-butanediol (100 mg, 1.11 mmol, 3.2 equivalents) and p-toluenesulfonic acid monohydrate (70 mg, 0.368 mmol, 1.0 equivalent), and then the mixture was refluxed with heating for 3.5 hours. To the reaction solution was added saturated aqueous sodium hydrogen carbonate, the mixture was extracted with chloroform, and the organic layer was washed with saturated aqueous sodium chloride and dried over anhydrous sodium sulfate. The solvent was evaporated to obtain an adduct (156 mg, 0.313 mmol), from which the title compound (48 mg, 33%) was obtained as white crystals in a manner similar to the method by which Compound 40 was obtained from Adduct 40a in Example 40.

Melting point: 169–170° C. (acetone)
$^1$H-NMR (270 MHz, CDCl$_3$) δ 0.99 (t, 3H, J=7.6 Hz), 1.31 (d, 3H, J=5.9 Hz), 1.34 (d, 3H, J=5.9 Hz), 1.89 (q, 2H, J=7.6 Hz), 2.83–2.87 (m, 2H), 3.79 (dq, 1H, J=7.9, 5.9 Hz), 3.86–3.95 (m, 2H), 4.09–4.19 (m, 3H), 4.46 (m, 1H), 6.07 (s, 1H), 7.09–7.19 (m, 5H).
IR (KBr) 1711, 1689, 1670, 1648, 1548, 1456, 1273 cm$^{-1}$
EI-MS: m/z 410 (M$^+$+1).
Elemental Analysis for C$_{22}$H$_{27}$N$_5$O$_3$·0.2H$_2$O
Calculated (%): C, 63.97; H, 6.69; N, 16.95. Found (%): C, 63.92; H, 6.73; N, 17.11.

EXAMPLE 47

(R)-1,8-Dibenzyl-7,8-dihydro-2-methoxycarbonyl-4-(n-propyl)-1H-imidazo[2,1-i]purin-5(4H)-one (Compound 47)

Compound 35a (3.95 g, 9.90 mmol) obtained in Example 35 was dissolved in tetrahydrofuran (100 mL), to the solution was added a 1.50 mol/L solution (9.9 mL) of lithium diisopropylamide (14.9 mmol, 1.5 equivalents) in cyclohexane at −78° C., and then the mixture was stirred for 1 hour. Into the reaction solution was poured carbon dioxide generated from dry ice and the mixture was stirred at room temperature for 1 hour. To the reaction solution was added 1 mol/L aqueous hydrochloric acid and the mixture was extracted with chloroform. The organic layer was washed with saturated aqueous sodium chloride and dried. The solvent was evaporated, and the residue was purified by silica gel column chromatography (chloroform:methanol=95:5 to 10:1). To the residue were added acetone and diethyl ether, and the deposited crystals were collected by filtration to obtain (R)-1,8-dibenzyl-2-carboxy-7,8-dihydro-4-(n-propyl)-1H-imidazo[2,1-i]purin-5(4H)-one (Compound 47a, 1.13 g, 26%). To Compound 47a (740 mg, 1.67 mmol) was added thionyl chloride (10.0 mL, 137 mmol, 82 equivalents) and the mixture was stirred at 60° C. for 2 hours. The reaction solution was concentrated under reduced pressure, and then to the reaction residue was added methanol (3 mL). The mixture was concentrated and the residue was directly purified by silica gel column chromatography (chloroform:methanol=95:5) to obtain the title compound (211 mg, 28%).

$^1$H-NMR (270 MHz, CDCl$_3$) δ 0.94 (t, 3H, J=7.3 Hz), 1.74 (q, 2H, J=7.3 Hz), 2.77 (dd, 1H, J=13.7, 7.8 Hz), 3.06 (dd, 1H, J=13.7, 5.4 Hz), 3.67 (dd, 1H, J=11.1, 7.0 Hz), 3.87 (dd, 1H, J=11.1, 10.0 Hz), 3.92–3.99 (m, 5H), 4.61 (m, 1H), 6.01 (d, 1H, J=14.8 Hz), 6.09 (d, 1H, J=14.8 Hz), 7.16–7.35 (m, 10H).
EI-MS: m/z 458 (M$^+$+1).

EXAMPLE 48

(R)-1,8-Dibenzyl-7,8-dihydro-2-(2-hydroxypropan-2-yl)-4-(n-propyl)-1H-imidazo[2,1-i]purin-5(4H)-one (Compound 48)

Compound 47 (100 mg, 0.218 mmol) obtained in Example 47 was dissolved in tetrahydrofuran (5 mL), to the solution was added a 3.0 mol/L solution (500 μL) of methyl magnesium bromide (1.50 mmol, 6.8 equivalents) in diethyl ether, and the mixture was stirred at room temperature for 1 hour. The reaction solution was concentrated under reduced pressure and then the residue was directly purified by silica gel column chromatography (chloroform:methanol=95:5) to obtain the title compound (60 mg, 60%).

$^1$H-NMR (270 MHz, CDCl$_3$) δ 0.95 (t, 3H, J=7.3 Hz), 1.51 (s, 3H), 1.52 (s, 3H), 1.74 (q, 2H, J=7.3 Hz), 2.62 (dd, 1H, J=13.5, 7.9 Hz), 2.95 (dd, 1H, J=13.5, 5.6 Hz), 3.60 (dd, 1H, J=11.2, 6.9 Hz), 3.77 (dd, 1H, J=11.2, 9.9 Hz), 3.91 (t, 2H, J=7.3 Hz), 4.45 (m, 1H), 5.82 (d, 1H, J=16.2 Hz), 5.89 (d, 1H, J=16.2 Hz), 7.03–7.37 (m, 10H).
EI-MS: m/z 458 (M$^+$+1).

EXAMPLE 49

(R)-8-Benzyl-7,8-dihydro-2-piperidinocarbonyl-4-(n-propyl)-1H-imidazo[2,1-i]purin-5(4H)-one (Compound 49)

Compound 47a (70 mg, 0.158 mmol) obtained in Example 47 was dissolved in chloroform (2 mL), to the solution was added thionyl chloride (40 μL, 0.548 mmol, 3.4 equivalents), and the mixture was stirred at 60° C. for 30 minutes. To the reaction solution was added piperidine (320 μL, 3.24 mmol, 20 equivalents) and the mixture was stirred at room temperature for 30 minutes. The reaction mixture was concentrated and directly purified by silica gel column chromatography (chloroform:methanol=98:2). Thereafter, the title compound (17 mg, 26%) was obtained in a manner similar to the method by which Compound 40 was obtained from Adduct 40a in Example 40.

$^1$H-NMR (270 MHz, CDCl$_3$) δ 0.96 (t, 3H, J=7.4 Hz), 1.50–1.75 (m, 6H), 1.82 (q, 2H, J=7.4 Hz), 2.78 (dd, 1H, J=13.7, 5.5 Hz), 3.06 (dd, 1H, J=13.7, 5.1 Hz), 3.67–4.19 (m, 8H), 5.05 (m, 1H), 7.14–7.27 (m, 5H).

EI-MS: m/z 421 (M$^+$+1).

EXAMPLE 50

(R)-8-Benzyl-7,8-dihydro-2-morpholinocarbonyl-4-(n-propyl)-1H-imidzole[2,1-i]purin-5(4H)-one (Compound 50)

In a manner similar to that in Example 49, the title compound (15 mg, 9%) was obtained from Compound 47a (50 mg, 0.113 mmol) obtained in Example 47 and morpholine (100 µL, 1.15 mmol, 10 equivalents).

$^1$H-NMR (270 MHz, CDCl$_3$) δ 0.97 (t, 3H, J=7.3 Hz), 1.82 (q, 2H, J=7.3 Hz), 2.81 (dd, 1H, J=13.2, 7.9 Hz), 3.03 (dd, 1H, J=13.2, 5.6 Hz), 3.67–3.96 (m, 4H), 3.98–4.25 (m, 8H), 5.04 (m, 1H), 7.10–7.18 (m, 5H).

EI-MS: m/z 423 (M$^+$+1).

EXAMPLE 51

(R)-8-Benzyl-7,8-dihydro-4-(n-propyl)-2-(tetrahydrofuran-2-yl)-1H-imidazo[2,1-i]purin-5(4H)-one D-tartrate (Compound 51)

In a manner similar to that in Example 45, an adduct (1.38 g, 99%) was obtained from Compound B13 (1.00 g, 3.40 mmol) prepared in Reference Example 23 and (R)-phenylalaminol (770 mg, 5.10 mmol, 1.5 equivalents). To a solution of the adduct (1.00 g, 2.52 mmol) in methylene chloride (10 mL) was added methanesulfonyl chloride (390 µL, 5.01 mmol, 2.0 equivalents) and pyridine (200 µL, 2.50 mmol, 1.0 equivalent) and the mixture was stirred at room temperature for 20 hours. To the reaction solution were further added methanesulfonyl chloride (390 µL, 5.01 mmol, 2.0 equivalents) and pyridine (200 µL) and the mixture was stirred for 24 hours. The reaction mixture was concentrated, to the resulting residue was added saturated aqueous sodium hydrogen carbonate, and the mixture was stirred for 1 hour. The reaction mixture was extracted with chloroform, and the resulting organic layer was dried over anhydrous magnesium sulfate. The solvent was evaporated, and the residue was purified by silica gel column chromatography (chloroform:methanol=99:1) to obtain the title compound in the free form. To a methanol solution of the title compound in the free form was added D-tartaric acid for salt formation to obtain the title compound (250 mg, 5%).

Melting point: 148–149° C. (methanol)

$^1$H-NMR (270 MHz, CDCl$_3$) δ 0.94–0.99 (m, 3H), 1.72–1.81 (m, 2H), 2.00–2.18 (m, 3H), 2.40 (m, 1H), 3.02 (m, 1H), 3.21 (m, 1H), 3.92–4.24 (m, 6H), 4.45 (s, 2H), 4.76 (m, 1H), 5.13 (dd, 1H, J=7.9, 5.6 Hz), 7.23–7.31 (m, 5H).

IR (KBr) 1734, 1720, 1711, 1703, 1670 cm$^{-1}$

TOF-MS: m/z 380 (M$^+$+1).

EXAMPLE 52

(R)-8-Benzyl-2-(1-ethoxyethyl)-7,8-dihydro-4-(n-propyl)-1H-imidazo[2,1-i]purin-5(4H)-one 0.5 fumarate (Compound 52)

In a manner similar to that in Example 45, the title compound in the free form was obtained from Compound B14 (500 mg, 1.69 mmol) prepared in Reference Example 24 and (R)-phenylalaminol (380 mg, 2.51 mmol, 1.5 equivalents), and it was subjected to salt formation with fumaric acid to obtain the title compound (77 mg, 4%) as white crystals.

Melting point: 165–170° C. (ethyl acetate/n-hexane)

$^1$H-NMR (270 MHz, CDCl$_3$) δ 0.95 (t, 3H, J=7.3 Hz), 1.28 (t, 3H, J=6.9 Hz), 1.60 (d, 3H, J=6.6 Hz), 1.77 (q, 2H, J=7.3 Hz), 2.98 (dd, 1H, J=13.9, 7.9 Hz), 3.23 (brd, 1H, J=13.9 Hz), 3.57 (q, 2H, J=6.9 Hz), 4.00 (dd, 1H, J=11.9, 6.9 Hz), 4.07 (t, 2H, J=7.3 Hz), 4.14 (t, 1H, J=11.8 Hz), 4.67 (q, 1H, J=6.9 Hz), 6.91 (s, 2H), 7.23–7.32 (m, 5H).

IR (KBr) 1738, 1716, 1699, 1687, 1674, 1651, 1583, 1367, 1271 cm$^{-1}$

EI-MS: m/z 382 (M$^+$+1).

Elemental Analysis for C$_{21}$H$_{27}$N$_5$O$_2$·0.5C$_4$H$_4$O$_4$·0.3H$_2$O

Calculated (%): C, 62.09; H, 6.71; N, 15.74. Found (%): C, 62.20; H, 6.72; N, 15.32.

EXAMPLE 53

(R)-8-Benzyl-7,8-dihydro-4-(n-propyl)-2-(tetrahydropyran-4-yl)-1H-imidazo[2,1-i]purin-5(4H)-one hydrochloride (Compound 53)

In a manner similar to that in Example 45, the title compound in the free form (250 mg, 85%) was obtained from Compound B15 (230 mg, 0.752 mmol) prepared in Reference Example 25 and (R)-phenylalaminol (170 mg, 1.18 mmol, 1.6 equivalents), and it was converted into hydrochloride with a 4 mol/L solution of hydrogen chloride in dioxane. The deposited solid was washed with ethyl acetate to obtain the title compound (120 mg, 37%).

Melting point: 226–227° C. (dioxane)

$^1$H-NMR (270 MHz, CDCl$_3$) δ 0.95 (t, 3H, J=7.4 Hz), 1.70–1.83 (m, 2H), 1.92–2.10 (m, 4H), 3.01 (dd, 1H, J=13.9, 7.9 Hz), 3.12 (m, 1H), 3.23 (dd, 1H, J=13.9, 4.6 Hz), 3.53 (dt, 2H, J=11.6, 2.6 Hz), 4.03–4.12 (m, 5H), 4.23 (dd, 1H, J=11.9, 9.9 Hz), 4.71 (m, 1H), 7.26–7.38 (m, 5H), 11.4 (brs, 1H), 13.9 (brs, 1H).

IR (KBr) 2996, 1703, 1668, 744, 727 cm$^{-1}$

TOF-MS: m/z 394 (M$^+$+1).

Elemental Analysis for C$_{22}$H$_{27}$N$_5$O$_2$·HCl

Calculated (%): C, 61.46; H, 6.56; N, 16.29. Found (%): C, 61.34; H, 6.94; N, 16.16.

EXAMPLE 54

(R)-8-Benzyl-7,8-dihydro-2-(trans-4-hydroxyhexyl)-4-(n-propyl)-1H-imidazo[2,1-i]purin-5(4H)-one hydrochloride (Compound 54)

In a manner similar to that in Example 45, a ketone compound (940 mg, 98%) was obtained from Compound B16 (1.00 g, 3.25 mmol) prepared in Reference Example 26 and (R)-phenylalaminol (740 mg, 4.89 mmol, 1.5 equivalents). The ketone compound (300 mg, 0.741 mmol) was dissolved in methanol (5 mL) and to the solution was added sodium borohydride (28 mg, 0.741 mmol, 1.0 equivalent)

with ice cooling. The ice bath was removed, and the reaction mixture was warmed to room temperature and stirred for 20 hours. To the reaction mixture was added a small amount of acetone, the mixture was stirred, then the solvent was evaporated under reduced pressure, and the residue was partitioned with 2 mol/L aqueous sodium hydroxide and chloroform. The resulting organic layer was dried over anhydrous magnesium sulfate and concentrated. The residue was purified by silica gel column chromatography (chloroform:methanol=95:5) to obtain the title compound in the free form (170 mg, 56%). The free compound (70 mg, 0.172 mmol) was converted into hydrochloride with a 4 mol/L solution of hydrogen chloride in dioxane to obtain the title compound (60 mg, 80%).

Melting point: 115–116° C. (dioxane)
$^1$H-NMR (270 MHz, CDCl$_3$) δ 0.95 (t, 3H, J=7.6 Hz), 1.40–1.83 (m, 6H), 2.11–2.24 (m, 4H), 2.84 (ddd, 1H, J=8.6, 3.3, 3.3 Hz), 3.01 (dd, 1H, J=13.9, 7.9 Hz), 3.23 (dd, 2H, J=13.9, 4.8 Hz), 3.72 (m, 1H), 4.02–4.26 (m, 4H), 4.68 (m, 1H), 7.26–7.64 (m, 5H), 11.3 (brs, 1H), 13.8 (brs, 1H).
IR (KBr) 2937, 1716, 1670, 752 cm$^{-1}$
TOF-MS: m/z 408 (M$^+$+1).
Elemental Analysis for C$_{22}$H$_{29}$N$_5$O$_2$·HCl·2H$_2$O
Calculated (%): C, 57.55; H, 7.14; N, 14.59. Found (%): C, 57.97; H, 7.34; N, 14.43.

EXAMPLE 55

(R)-8-Benzyl-2-(1,3-dioxolane-2-spirocyclopentan-2'-yl)-7,8-dihydro-4-(n-propyl)-1H-imidazo[2,1-i]purin-5(4H)-one (Compound 55)

In a manner similar to that in Example 45, the title compound (720 mg, 39%) was obtained from Compound B17 (1.50 g, 4.29 mmol) prepared in Reference Example 27 and (R)-phenylalaminol (970 mg, 6.44 mmol, 1.5 equivalents).

$^1$H-NMR (270 MHz, CDCl$_3$) δ 0.95 (dt, 3H, J=7.4, 2.7 Hz), 1.72–2.09 (m, 6H), 2.16–2.22 (m, 2H), 2.84 (dd, 1H, J=13.8, 7.5 Hz), 3.06 (m, 1H), 3.37 (m, 1H), 3.65–4.05 (m, 8H), 4.43 (m, 1H), 7.20–7.31 (m, 5H).
IR (KBr) 1714, 1683, 1587, 746, 704 cm$^{-1}$
TOF-MS: m/z 436 (M$^+$+1).

EXAMPLE 56

(R)-8-Benzyl-2-benzyloxymethyl-7,8-dihydro-4-(n-propyl)-1H-imidazo[2,1-i]purin-5(4H)-one 0.5 fumarate (Compound 56)

In a manner similar to that in Example 45, the title compound in the free form (109 mg) was obtained from Compound B18 (250 mg, 0.726 mmol) prepared in Reference Example 28 and (R)-phenylalaminol (130 mg, 0.860 mmol, 1.2 equivalents), and the title compound (62 mg, 18%) was obtained as white crystals from the free compound and fumaric acid.

Melting point: 130–132° C. (ethyl acetate)
$^1$H-NMR (270 MHz, CDCl$_3$) δ 0.96 (t, 3H, J=7.3 Hz), 1.78 (q, 2H, J=7.3 Hz), 2.99 (dd, 1H, J=13.8, 7.6 Hz), 3.19 (dd, 1H, J=13.8, 5.0 Hz), 4.01 (dd, 1H, J=11.6, 6.3 Hz), 4.06 (t, 2H, J=7.3 Hz), 4.19 (dd, 1H, J=11.9, 9.9 Hz), 4.65 (m, 1H), 4.70 (s, 4H), 6.91 (s, 2H), 7.22–7.46 (m, 10H).
IR (KBr) 1716, 1675, 1654, 1578, 1454, 1365 cm$^{-1}$
EI-MS: m/z 430 (M$^+$+1).
Elemental Analysis for C$_{25}$H$_{27}$N$_5$O$_2$·0.5C$_4$H$_4$O$_4$·0.3H$_2$O
Calculated (%): C, 65.79; H, 6.05; N, 14.21. Found (%): C, 65.60; H, 6.02; N, 14.76.

EXAMPLE 57

(R)-8-Benzyl-7,8-dihydro-2-(α-methoxybenzyl)-4-(n-propyl)-1H-imidazo[2,1-i]purin-5(4H)-one 0.5 fumarate (Compound 57)

In a manner similar to that in Example 45, the title compound in the free form (111 mg) was obtained from Compound B19 (176 mg, 0.511 mmol) prepared in Reference Example 29 and (R)-phenylalaminol (120 mg, 0.794 mmol, 1.5 equivalents), and the title compound (20 mg, 8%) was obtained as white crystals from the free compound and fumaric acid.

Melting point: 160–162° C. (acetone/diethyl ether)
$^1$H-NMR (270 MHz, CDCl$_3$) δ 0.99 (t, 3H, J=7.2 Hz), 1.75 (q, 2H, J=7.2 Hz), 2.99 (dd, 1H, J=13.8, 7.9 Hz), 3.21 (dd, 1H, J=13.9, 5.6 Hz), 3.49 (s, 3H), 4.07 (dd, 1H, J=11.6, 6.3 Hz), 4.14 (t, 2H, J=13.9 Hz), 4.19 (dd, 1H, J=11.9, 9.9 Hz), 4.65 (m, 1H), 5.60 (s, 1H), 7.23 (s, 2H), 7.28–7.40 (m, 8H), 7.60 (d, 2H, J=6.9 Hz).
IR (KBr) 1722, 1713, 1691, 1678, 1666, 1643, 1581, 1365 cm$^{-1}$
EI-MS: m/z 430 (M$^+$).
Elemental Analysis for C$_{25}$H$_{27}$N$_5$O$_2$·0.5C$_4$H$_4$O$_4$·0.5H$_2$O
Calculated (%): C, 65.30; H, 6.09; N, 14.10. Found (%): C, 65.38; H, 6.20; N, 14.19.

EXAMPLE 58

(R)-8-Benzyl-7,8-dihydro-2-(2-methoxyethyl)-4-(n-propyl)-1H-imidazo[2,1-i]purin-5(4H)-one hydrochloride (Compound 58)

In a manner similar to that in Example 45, the title compound in the free form was obtained from Compound B20 (750 mg, 2.66 mmol) prepared in Reference Example 30 and (R)-phenylalaminol (610 mg, 4.03 mmol, 1.5 equivalents), and it was converted into hydrochloride with a 4 mol/L solution of hydrogen chloride in dioxane to obtain the title compound (820 mg, 76%).

Melting point: 150–151° C. (ethyl acetate/hexane)
$^1$H-NMR (270 MHz, CDCl$_3$) δ 0.95 (t, 3H, J=7.6 Hz), 1.72–1.83 (m, 2H), 3.00 (dd, 1H, J=13.9, 7.9 Hz), 3.14 (t, 2H, J=5.9 Hz), 3.24 (dd, 1H, J=13.9, 4.6 Hz), 3.47 (s, 3H), 3.81 (t, 2H, J=5.9 Hz), 4.06 (t, 2H, J=7.3 Hz), 4.07 (dd, 1H, J=6.9, 5.9 Hz), 4.21 (dd, 1H, J=11.9, 9.9 Hz), 4.71 (m, 1H), 7.25–7.36 (m, 5H), 11.8 (brs, 1H), 13.6 (brs, 1H).
IR (KBr) 2832, 1714, 1678, 744, 725 cm$^{-1}$
TOF-MS: m/z 368 (M$^+$+1).
Elemental Analysis for C$_{20}$H$_{25}$N$_5$O$_2$·HCl
Calculated (%): C, 59.47; H, 6.49; N, 17.34. Found (%): C, 59.43; H, 6.71; N, 17.09.

EXAMPLE 59

(R)-8-Benzyl-2-(2-carboxylethyl)-7,8-dihydro-4-(n-propyl)-1H-imidazo[2,1-i]purin-5(4H)-one (Compound 59)

To Compound B21 (1.00 g, 3.78 mmol) obtained in Reference Example 31 and (R)-phenylalaminol (860 mg, 5.67 mmol, 1.5 equivalents) was added pyridine (10 mL) and the mixture was refluxed with heating for 9 hours. The solvent was evaporated under reduced pressure, then to the residue was added water, and the mixture was partitioned with chloroform. The resulting aqueous layer was concentrated to the solid state under reduced pressure, ethanol was added, and then the mixture was filtered. The resulting filtrate was concentrated to obtain a crude product. The resulting product was desalted by using HP-22 to obtain (R)-8-(2-carboxyethyl)-6-[2-(1-hydroxy-3-phenylpropan-2-yl)amino]-3-(n-propyl)-7H-purin-2(3H)-one (1.05 g, 70%). The resulting carboxylic acid (1.00 g, 2.51 mmol) was added to a solution which was obtained by addition of thionyl chloride (732 µL, 10.0 mmol, 4.0 equivalents) to cooled methanol (50 mL), and then the mixture was warmed to room temperature and stirred for 15 hours. The reaction mixture was concentrated and partitioned with saturated aqueous sodium hydrogen carbonate and ethyl acetate. The resulting organic layer was dried over anhydrous magnesium sulfate, and the solvent was evaporated under reduced pressure. The resulting residue was purified by silica gel column chromatography (chloroform:methanol=100:0 to 95:5) to obtain (R)-6-[2-(1-hydroxy-3-phenylpropan-2-yl)amino]-8-(2-methoxycarboxyethyl)-3-(n-propyl)-7H-purin-2(3H)-one (500 mg, 48%). To the resulting ester compound (250 mg, 0.61 mmol) was added thionyl chloride (1 mL) and the mixture was stirred at 60° C. for 2 hours. Excess reagents were evaporated under reduced pressure, to the reaction mixture were added ethyl acetate and saturated aqueous sodium hydrogen carbonate, and then the mixture was stirred. The reaction mixture was partitioned, and the resulting organic layer was dried over anhydrous magnesium sulfate. The solvent was evaporated, and the resulting residue was purified by silica gel column chromatography (chloroform:methanol=99:1) to obtain (R)-8-benzyl-7,8-dihydro-2-(2-methoxycarboxyethyl)-4-(n-propyl)-1H-imidazo[2,1-i]-purin-5(4H)-one (260 mg, 99%). To the ester compound (180 mg, 0.46 mmol) was added methanol (4 mL) and 2 mol/L aqueous sodium hydroxide (2 mL) and the mixture was stirred at room temperature for 12 hours. The reaction mixture was adjusted to pH 3 with 4 mol/L hydrochloric acid. The deposited solid was collected by filtration to obtain the title compound (140 mg, 80%).

Melting point: 274–276° C. (methanol/water)
$^1$H-NMR (270 MHz, DMSO-$d_6$) δ 0.86 (t, 3H, J=7.3 Hz), 1.60–1.68 (m, 2H), 2.66 (t, 2H, J=7.3 Hz), 2.81–3.01 (m, 4H), 3.63 (dd, 1H, J=11.0, 6.8 Hz), 3.80–3.96 (m, 3H), 4.51 (m, 1H), 7.18–7.30 (m, 5H).
IR (KBr) 1720, 1705, 1686 cm$^{-1}$
FAB-MS: m/z 382 (M$^+$+1).
Elemental Analysis for $C_{20}H_{23}N_5O_3$·1.8$H_2O$
Calculated (%): C, 58.04; H, 6.48; N, 16.92. Found (%): C, 58.24; H, 6.11; N, 17.14.

EXAMPLE 60

(S)-8-(tert-Butyl)-7,8-dihydro-2-(1-methylsulfonylpiperidin-4-yl)-4-(n-propyl)-1H-imidazo[2,1-i]purin-5(4H)-one (Compound 60)

In a manner similar to that in Example 45, the title compound (3 mg, 14%) was obtained from Compound B22 (19 mg, 0.049 mmol) prepared in Reference Example 32 and (S)-tert-butylalaminol (9 mg, 0.077 mmol, 1.5 equivalents).
$^1$H-NMR (270 MHz, CDCl$_3$) δ 0.99 (t, 3H, J=7.6 Hz), 1.07 (s, 9H), 1.74–1.85 (m, 2H), 1.95–2.17 (m, 2H), 2.18–2.27 (m, 2H), 2.83 (s, 3H), 2.78–3.03 (m, 4H), 3.81–3.98 (m, 2H), 4.01–4.30 (m, 5H), 11.4 (brs, 1H).
TOF-MS: m/z 437 (M$^+$+1).

EXAMPLE 61

(R)-8-Benzyl-2-(1-tert-butoxycarbonylpiperidin-4-yl)-7,8-dihydro-4-(n-propyl)-1H-imidazo[2,1-i]purin-5(4H)-one hydrochloride (Compound 61)

In a manner similar to that in Example 45, the title compound in the free form was obtained from Compound B23 (1.00 g, 2.46 mmol) prepared in Reference Example 33 and (R)-phenylalaminol (557 mg, 3.69 mmol, 1.5 equivalents), and it was converted into hydrochloride with a 4 mol/L solution of hydrogen chloride in dioxane to obtain the title compound (580 mg, 48%).

Melting point: 204–205° C. (diisopropyl ether/hexane)
$^1$H-NMR (270 MHz, CDCl$_3$) δ 0.95 (t, 3H, J=7.4 Hz), 1.47 (s, 9H), 1.72–1.80 (m, 4H), 2.09–2.15 (m, 2H), 2.84–3.05 (m, 3H), 3.01 (dd, 1H, J=14.2, 7.6 Hz), 3.23 (dd, 1H, J=4.6, 14.2 Hz), 4.03–4.27 (m, 6H), 4.73 (m, 1H), 7.22–7.37 (m, 5H), 11.3 (brs, 1H), 13.9 (brs, 1H).
IR (KBr) 2941, 1720, 1682, 744 cm$^{-1}$
EI-MS: m/z 492 (M$^+$).
Elemental Analysis for $C_{27}H_{36}N_6O_3$·HCl·0.2$H_2O$
Calculated (%): C, 60.88; H, 7.08; N, 15.78. Found (%): C, 60.85; H, 7.21; N, 15.47.

EXAMPLE 62

(R)-2-[trans-4-(Aminomethyl)cyclohexyl]-8-benzyl-7,8-dihydro-4-(n-propyl)-1H-imidazo[2,1-i]purin-5(4H)-one (Compound 62)

In a manner similar to that in Example 45, an adduct was obtained from Compound B24 prepared in Reference Example 34 and (R)-phenylalaminol, and the adduct (600 mg, 1.11 mmol) was dissolved in methanol (5 mL). To the solution were added palladium hydroxide (600 mg, 10% on carbon) and ammonium formate (400 mg, 10.8 mmol, 10.0 equivalents), and the mixture was heated to 60° C. and stirred for 2 hours. The reaction mixture was cooled to room temperature and filtered by using Celite, and the resulting filtrate was concentrated. To the residue were added a small amount of water and sodium hydrogen carbonate and then the mixture was extracted with chloroform. The organic layer was dried over anhydrous magnesium sulfate, concentrated and purified by silica gel column chromatography (chloroform:methanol:ammonia=84:8:8) to obtain the title compound (150 mg, 32%).

Melting point: 70–71° C. (chloroform/methanol)
$^1$H-NMR (270 MHz, CDCl$_3$) δ 0.88–1.39 (m, 2H), 0.98 (t, 3H, J=7.4 Hz), 1.54–2.17 (m, 9H), 2.54 (d, 2H, J=6.6 Hz), 2.66 (m, 1H), 2.82–2.88 (m, 2H), 3.72 (dd, 1H, J=11.0, 6.8 Hz), 3.95–4.16 (m, 4H), 7.16–7.20 (m, 5H).
IR (KBr) 2927, 1695, 1660, 746, 702 cm$^{-1}$
TOF-MS: m/z 421 (M$^+$+1).

EXAMPLE 63

(R)-2-[trans-4-(Acetamidomethyl)cyclohexyl]-8-benzyl-7,8-dihydro-4-(n-propyl)-1H-imidazo[2,1-i]purin-5(4H)-one hydrochloride (Compound 63)

Compound 62 (50 mg, 0.119 mmol) obtained in Example 62 was dissolved in methylene chloride (500 µL), to the solution were added acetic anhydride (11 µL, 0.119 mmol, 1.0 equivalent) and pyridine (10 µL, 0.120 mmol, 1.0 equivalent), and the mixture was stirred at room temperature for 1.5 hours. To the reaction mixture was added saturated aqueous sodium hydrogen carbonate and the mixture was extracted with ethyl acetate. The resulting organic layer was dried over anhydrous magnesium sulfate, and the solvent was evaporated. The residue was purified by silica gel column chromatography (chloroform:methanol=100:0 to 98:2) to obtain the title compound in the free form (50 mg). The free compound was converted into hydrochloride with a 4 mol/L solution of hydrogen chloride in dioxane and the product was recrystallized from ethanol to obtain the title compound (51 mg, 86%).

$^1$H-NMR (270 MHz, CDCl$_3$) δ 0.98 (t, 3H, J=7.4 Hz), 1.01–1.09 (m, 2H), 1.58–2.18 (m, 9H), 2.00 (s, 3H), 2.68 (m, 1H), 2.78–2.88 (m, 2H), 3.10–3.17 (m, 2H), 3.75 (dd, 1H, J=10.3, 5.8 Hz), 3.94–4.07 (m, 4H), 5.82 (brt, 1H), 7.13–7.17 (m, 5H), 7.60 (brs, 1H).

IR (KBr) 3244, 2925, 1716, 1668, 1637, 752 cm$^{-1}$

TOF-MS: m/z 463 (M$^+$+1).

Elemental Analysis for C$_{26}$H$_{34}$N$_6$O$_2$.HCl.1.5H$_2$O

Calculated (%): C, 59.36; H, 7.28; N, 15.98. Found (%): C, 59.42; H, 7.20; N, 15.63.

EXAMPLE 64

(R)-8-Benzyl-2-ethylthiomethyl-7,8-dihydro-4-(n-propyl)-1H-imidazo[2,1-i]purin-5(4H)-one 0.5 fumarate (Compound 64)

In a manner similar to that in Example 45, the title compound in the free form was obtained from Compound B25 (1.00 g, 3.36 mmol) prepared in Reference Example 35 and (R)-phenylalaminol (770 mg, 5.09 mmol, 1.5 equivalents), and the title compound (139 mg, 10%) was obtained as white crystals from the free compound and fumaric acid.

Melting point: 178–180° C. (methanol/acetone)

$^1$H-NMR (270 MHz, CDCl$_3$) δ 0.96 (t, 3H, J=7.3 Hz), 1.31 (t, 3H, J=7.6 Hz), 1.78 (q, 2H, J=7.3 Hz), 2.66 (q, 2H, J=7.6 Hz), 3.00 (dd, 1H, J=13.8, 7.9 Hz), 3.22 (dd, 1H, J=13.8, 4.9 Hz), 3.87 (s, 2H), 4.04 (dd, 1H, J=11.6, 6.6 Hz), 4.07 (t, 2H, J=7.3 Hz), 4.19 (dd, 1H, J=11.6, 9.6 Hz), 4.70 (m, 1H), 6.88 (s, 2H), 7.24–7.36 (m, 5H).

IR (KBr) 1713, 1680, 1655, 1574, 1362, 1273 cm$^{-1}$

EI-MS: m/z 384 (M$^+$+1).

Elemental Analysis for C$_{20}$H$_{25}$N$_5$OS.0.5C$_4$H$_4$O$_4$.0.1H$_2$O

Calculated (%): C, 59.60; H, 6.18; N, 15.80. Found (%): C, 59.44; H, 6.08; N, 16.05.

EXAMPLE 65

(R)-8-Benzyl-2-ethylsulfonylmethyl-7,8-dihydro-4-(n-propyl)-1H-imidazo[2,1-i]purin-5(4H)-one 0.5 fumarate (Compound 65)

Compound 64 (593 mg, 1.55 mmol) obtained in Example 64 was dissolved in methanol (20 mL) and water (5 mL), to the solution was added OXONE® (3.80 g, 6.18 mmol, 4.0 equivalents), and the mixture was stirred at room temperature for 4 hours. To the reaction mixture was added saturated aqueous sodium hydrogen carbonate and the mixture was extracted with ethyl acetate. The resulting organic layer was dried over anhydrous magnesium sulfate, and the solvent was evaporated. The residue was purified by silica gel column chromatography (chloroform:methanol=100:0 to 98:2) to obtain the title compound in the free form. The title compound (311 mg, 49%) was obtained as white crystals from the free compound and fumaric acid.

Melting point: 180–182° C. (ethyl acetate)

$^1$H-NMR (270 MHz, CDCl$_3$) δ 0.96 (t, 3H, J=7.3 Hz), 1.46 (t, 3H, J=7.3 Hz), 1.75 (q, 2H, J=7.3 Hz), 3.03 (dd, 1H, J=13.9, 7.3 Hz), 3.16 (dd, 1H, J=13.9, 5.6 Hz), 3.24 (q, 2H, J=7.6 Hz), 4.06 (dd, 1H, J=11.9, 4.6 Hz), 4.08 (t, 2H, J=7.3 Hz), 4.26 (dd, 1H, J=11.9, 9.6 Hz), 4.46 (s, 2H), 4.70 (m, 1H), 6.84 (s, 2H), 7.23–7.37 (m, 5H).

IR (KBr) 1720, 1687, 1657, 1560, 1315, 1119 cm$^{-1}$

EI-MS: m/z 416 (M$^+$+1).

Elemental Analysis for C$_{20}$H$_{25}$N$_5$O$_3$S.0.5C$_4$H$_4$O$_4$.0.4H$_2$O

Calculated (%): C, 54.74; H, 5.77; N, 14.33. Found (%): C, 54.76; H, 5.85; N, 14.51.

EXAMPLE 66

(R)-1,8-Dibenzyl-5-chloro-2-cyclopentyl-7,8-dihydro-1H-imidazo[2,1-i]purine (Compound 66)

To Compound C2 (1.87 g, 4.05 mmol) obtained in Reference Example 37 was added thionyl chloride (15.0 mL, 207 mmol, 51 equivalents) and the mixture was stirred with heating at 60° C. for 1 hour. The reaction solution was concentrated under reduced pressure, the solvent was azeotroped with toluene, to the residue were carefully added chloroform and saturated sodium hydrogen carbonate, and the mixture was stirred at room temperature for 30 minutes. The reaction mixture was extracted with chloroform, then the organic layer was washed with saturated aqueous sodium chloride and dried over anhydrous sodium sulfate, and the solvent was evaporated. The residue was purified by silica gel column chromatography (chloroform:methanol=90:10) to obtain the title compound (1.87 g, 99%).

Melting point: 124–125° C. (ethyl acetate)

$^1$H-NMR (270 MHz, CDCl$_3$) δ 1.51–1.63 (m, 2H), 1.67–1.98 (m, 6H), 2.73 (dd, 1H, J=13.5, 8.3 Hz), 3.01 (quin, 1H, J=8.0 Hz), 3.08 (dd, 1H, J=13.5, 5.1 Hz), 3.83 (dd, 1H, J=11.2, 6.9 Hz), 4.04 (dd, 1H, J=11.2, 10.2 Hz), 4.57 (m, 1H), 5.53 (d, 1H, J=15.9 Hz), 5.62 (d, 1H, J=15.9 Hz), 7.10–7.38 (m, 10H).

IR (KBr) 1684, 1498, 1454, 1377, 1333 cm$^{-1}$

EI-MS: m/z 444 (M$^+$+1).

EXAMPLE 67

(R)-8-Benzyl-2-cyclopentyl-7,8-dihydro-5-(n-propylamino)-1H-imidazo[2,1-i]purine (Compound 67)

In a manner similar to that in Example 66, (R)-8-benzyl-5-chloro-2-cyclopentyl-7,8-dihydro-1H-imidazo[2,1-i]purine (Compound 67a) was obtained from Compound C10 prepared in Reference Example 44. To Compound 67a (200 mg, 0.244 mmol) was added n-propylamine (2 mL) and the mixture was stirred under reflux with heating for 3 hour. The reaction mixture was concentrated, and the residue was purified by silica gel column chromatography (chloroform: methanol=95:5, chloroform: a 7 mol/L ammonia/methanol solution=95:5) to obtain the title compound (183 mg, 99%) as an ocher solid.

Melting point: 108–110° C. (chloroform/methanol)

$^1$H-NMR (270 MHz, CDCl$_3$) δ 0.89 (t, 3H, J=7.6 Hz), 1.58–1.95 (m, 8H), 2.07–2.15 (m, 2H), 2.91 (dd, 1H, J=14.0, 6.2 Hz), 2.97 (dd, 1H, J=14.0, 7.6 Hz), 3.22 (q, 1H, J=8.4 Hz), 3.40 (t, 2H, J=7.3 Hz), 4.08 (m, 1H), 4.29–4.41 (m, 2H), 7.11–7.27 (m, 5H).

IR (CHCl$_3$) 3018, 1693, 1574, 1556, 1367 cm$^{-1}$

EI-MS: m/z 377 (M$^+$+1).

EXAMPLE 68

(R)-8-Benzyl-2-cyclopentyl-7,8-dihydro-5-(2-piperidinoethylamino)-1H-imidazo[2,1-i]purine (Compound 68)

Compound 67a (100 mg, 0.240 mmol) obtained in Example 67 was dissolved in tetrahydrofuran (2 mL), and to the solution were added 2-piperidinoethylamine (61 μL, 0.480 mmol, 2.0 equivalents) and N,N-diisopropylethylamine (344 μL, 0.960 mmol, 4.0 equivalents) and the mixture was stirred at 80° C. for 2 hours. The reaction mixture was concentrated, and then the residue was purified by silica gel column chromatography (chloroform:methanol=90:10, chloroform: a 7 mol/L ammonia/methanol solution=90:10). To the product was added diisopropyl ether, and the deposited crystals were collected by filtration and dried to obtain the title compound (110 mg, 94%) as white crystals.

Melting point: 154–156° C. (diisopropyl ether)
$^1$H-NMR (270 MHz, CDCl$_3$) δ 1.48–2.06 (m, 14H), 2.38–2.46 (m, 4H), 2.56 (t, 2H, J=5.9 Hz), 2.84 (dd, 1H, J=13.8, 8.1 Hz), 3.14–3.24 (m, 2H), 3.49 (t, 2H, J=5.9 Hz), 3.71 (dd, 1H, J=10.0, 6.8 Hz), 3.92 (t, 1H, J=10.0 Hz), 4.53 (m, 1H), 7.20–7.26 (m, 5H).
IR (CHCl$_3$) 1682, 1568, 1556, 1531 cm$^{-1}$
EI-MS: m/z 446 (M$^+$+1)

EXAMPLE 69

(R)-8-Benzyl-2-cyclopentyl-7,8-dihydro-5-(1-pyrrolidinyl)-1H-imidazo[2,1-i]purine (Compound 69)

In a manner similar to that in Example 67, the title compound (50 mg, 36%) was obtained as an ocher solid from Compound 67a (296 mg, 0.361 mmol) and pyrrolidine (2 mL).

Melting point: 202–204° C. (chloroform/methanol)
$^1$H-NMR (270 MHz, CDCl$_3$) δ 1.69–2.00 (m, 10H), 2.12–2.19 (m, 2H), 3.00 (dd, 1H, J=13.8, 7.8 Hz), 2.95–3.31 (m, 2H), 3.54–3.62 (m, 4H), 4.27 (dd, 1H, J=10.5, 6.2 Hz), 4.48 (t, 1H, J=10.5 Hz), 4.67 (m, 1H), 7.24–7.35 (m, 5H).
IR (CHCl$_3$) 1713, 1681, 1556, 1520 cm$^{-1}$
EI-MS: m/z 389 (M$^+$+1)

Example 70

(R)-8-Benzyl-2-(tert-butyl)-5-ethoxy-7,8-dihydro-1H-imidazo[2,1-i]purine (Compound 70)

In a manner similar to that in Example 66, a cyclized compound was obtained from Compound C8 prepared in Reference Example 43, to a solution of the cyclized compound (4.88 g, 14.3 mmol) in ethanol (30 mL) was added a 21% solution of sodium ethoxide (30 mL, 93.0 mmol, 6.5 equivalents) in ethanol, and then the mixture was stirred with heating at 70° C. for 3 hours. The reaction solution was concentrated, and the deposited crystals were collected by filtration and recrystallized from ethyl acetate to obtain the title compound (2.67 g, 54%) as white crystals.

Melting point: 220–222° C. (ethyl acetate)
$^1$H-NMR (270 MHz, CDCl$_3$) δ 1.37 (t, 3H, J=7.3 Hz), 1.41 (s, 9H), 2.80 (dd, 1H, J=13.9, 7.9 Hz), 3.11 (dd, 1H, J=13.9, 6.3 Hz), 3.71 (dd, 1H, J=11.3, 7.3 Hz), 3.99 (dd, 1H, J=11.3, 9.9 Hz), 4.48 (q, 2H, J=7.3 Hz), 4.55 (m, 1H), 7.24–7.35 (m, 5H).
IR (KBr) 1678, 1668, 1655, 1558, 1539, 1431, 1350 cm$^{-1}$
EI-MS: m/z 351 (M$^+$).
Elemental Analysis for C$_{20}$H$_{25}$N$_5$O.0.2H$_2$O
Calculated (%): C, 67.66; H, 7.21; N, 19.72. Found (%): C, 67.70; H, 7.37; N, 19.62.

EXAMPLE 71

(R)-8-Benzyl-2-cyclopentyl-7,8-dihydro-5-(3-methylthiopropyloxy)-1H-imidazo[2,1-i]purine (Compound 71)

To a solution of Compound 67a (240 mg, 0.585 mmol) obtained in Example 67 in tetrahydrofuran (2 mL) were added 2-methylthiopropanol (1 mL) and sodium hydride (containing 34% mineral oil, 88 mg, 2.34 mmol), then Compound 67a (240 mg, 0.585 mmol) was further added to the mixture, and stirring was continued at 100° C. for 4 hours. To the reaction mixture was added ethyl acetate, and the mixture was washed twice with water and dried over magnesium sulfate. The reaction mixture was concentrated, and the residue was purified by silica gel column chromatography (chloroform:methanol=99:1) to obtain the title compound (100 mg, 40%) as an ocher foamy solid.

$^1$H-NMR (270 MHz, CDCl$_3$) δ 1.68–2.18 (m, 10H), 2.11 (s, 3H), 2.60 (t, 2H, J=6.8 Hz), 2.97 (dd, 1H, J=13.8, 7.8 Hz), 3.22 (dd, 1H, J=13.8, 4.9 Hz), 3.31 (m, 1H), 4.05 (dd, 1H, J=11.9, 6.8 Hz), 4.25 (t, 1H, J=11.3 Hz), 4.61 (t, 2H, J=6.5 Hz), 4.64 (m, 1H), 7.23–7.34 (m, 5H)
IR (CHCl$_3$) 1702, 1579, 1538, 1417, 1371 cm$^{-1}$
EI-MS: m/z 424 (M$^+$+1)

EXAMPLE 72

(R)-8-Benzyl-2-cyclopentyl-7,8-dihydro-5-(3-methylsulfonylpropyloxy)-1H-imidazo[2,1-i]purine (Compound 72)

In a manner similar to that in Example 65, the title compound (25 mg, 29%) was obtained as an ocher foamy solid from Compound 71 (80 mg, 0.190 mmol) obtained in Example 71.

$^1$H-NMR (270 MHz, CDCl$_3$) δ 1.67–2.06 (m, 8H), 2.30–2.38 (m, 2H), 2.83 (dd, 1H, J=7.0, 14.0 Hz), 2.94 (s, 3H), 3.06 (m, 1H), 3.12–3.23 (m, 3H), 3.80 (dd, 1H, J=7.0, 11.3 Hz), 4.03 (t, 1H, J=10.8 Hz), 4.40 (m, 1H), 4.61 (t, 2H, J=6.5 Hz), 7.20–7.37 (m, 5H)
IR (CHCl$_3$) 1693, 1681, 1539, 1311, 1136 cm$^{-1}$
EI-MS: m/z 456 (M$^+$+1)

EXAMPLE 73

(R)-8-Benzyl-2-(tert-butyl)-7,8-dihydro-5-methylthio-1H-imidazo[2,1-i]purine (Compound 73)

In a manner similar to that in Example 66, the title compound (1.12 g, 36%) was obtained as white crystals from Compound C9 (3.30 g, 8.90 mmol) prepared in Reference Example 43.

Melting point: 171–174° C. (acetone/diethyl ether)
$^1$H-NMR (270 MHz, CDCl$_3$) δ 1.42 (s, 9H), 2.63 (s, 3H), 2.82 (dd, 1H, J=13.8, 7.9 Hz), 3.11 (dd, 1H, J=13.8, 5.8 Hz), 3.73 (dd, 1H, J=10.2, 6.9 Hz), 4.00 (t, 1H, J=10.2 Hz), 4.59 (dq, 2H, J=9.9, 6.9 Hz), 7.23–7.36 (m, 5H).
IR (KBr) 1670, 1518, 1501, 1408, 1344 cm$^{-1}$
EI-MS: m/z 354 (M$^+$+1).
Elemental Analysis for C$_{19}$H$_{23}$N$_5$S.0.2H$_2$O Calculated (%): C, 63.91; H, 6.60; N, 19.61. Found (%): C, 63.70; H, 6.54; N, 19.89.

EXAMPLE 74

(R)-8-Benzyl-2-cyclopentyl-5-ethyl-7,8-dihydro-1H-imidazo[2,1-i]purine (Compound 74)

Compound 67a (82 mg, 0.20 mmol) obtained in Example 67 was dissolved in tetrahydrofuran (1 mL), to the solution was added a 1 mol/L solution (2 mL) of ethyl magnesium bromide in tetrahydrofuran, and the mixture was stirred at 60° C. for 1 hour. To the reaction mixture was added water and the mixture was stirred. Ethyl acetate was added to the mixture and the organic layer was washed with water and dried over magnesium sulfate. The organic layer was concentrated and to the residue were added dichloromethane and diisopropyl ether. The deposited crystals were collected by filtration to obtain the title compound (40 mg, 58%) as a white solid.

Melting point: 187–189° C. (dichloromethane/diisopropyl ether)

$^1$H-NMR (270 MHz, CDCl$_3$) δ 1.37 (t, 3H, J=7.6 Hz), 1.64–2.10 (m, 8H), 2.62 (q, 2H, J=7.6 Hz), 2.77 (dd, 1H, J=13.8, 5.9 Hz), 2.95 (dd, 1H, J=13.8, 6.8 Hz), 3.23 (q, 1H, J=8.4 Hz), 3.79 (m, 1H), 4.02–4.09 (m, 2H), 7.10–7.13 (m, 5H).

IR (CHCl$_3$) 1680, 1539, 1417, 1338 cm$^{-1}$

EI-MS: m/z 348 (M$^+$+1)

EXAMPLE 75

(R)-8-Benzyl-5-cyano-2-cyclopentyl-7,8-dihydro-1H-imidazo[2,1-i]purine (Compound 75)

Compound 67a (217 mg, 0.529 mmol) obtained in Example 67 was dissolved in N,N-dimethylformamide (4 mL), to the solution were added cesium carbonate (245 mg, 0.750 mmol, 1.5 equivalents) and potassium cyanide (39 mg, 0.600 mmol, 1.2 equivalents), and the mixture was stirred at 100° C. for 4 hours. To the reaction mixture was added water, and the deposited crystals were collected by filtration to obtain the title compound (125 mg, 73%) as a yellow solid.

Melting point: 140–142° C. (water)

$^1$H-NMR (270 MHz, CDCl$_3$) δ 1.65–2.07 (m, 8H), 2.79–2.94 (m, 2H), 3.19 (q, 1H, J=8.4 Hz), 3.94–4.04 (m, 2H), 4.27 (m, 1H), 7.11–7.19 (m, 5H).

IR (CHCl$_3$) 2246, 1664, 1454, 1421, 1388 cm$^{-1}$

EI-MS: m/z 345 (M$^+$+1)

EXAMPLE 76

(R)-8-Benzyl-2-cyclopentyl-7,8-dihydro-5-(1H-tetrazol-5-yl)-1H-imidazo[2,1-i]purine (Compound 76)

Compound 75 (69 mg, 0.200 mmol) obtained in Example 75 was dissolved in 1-methyl-2-pyrrolidinone (1 mL), to the solution were added sodium azide (52 mg, 0.800 mmol, 4.0 equivalents) and ammonium chloride (42 mg, 0.800 mmol, 4.0 equivalents), and the mixture was stirred at 120° C. for 2 hours. To the reaction mixture was added water, and the deposited crystals were collected by filtration to obtain the title compound (64 mg, 83%) as a white solid.

Melting point: 268–270° C. (water)

$^1$H-NMR (270 MHz, DMSO-d$_6$) δ 1.69–2.08 (m, 8H), 3.07 (dd, 1H, J=13.8, 4.9 Hz), 3.12 (dd, 1H, J=13.8, 7.3 Hz), 3.28 (m, 1H), 4.76 (m, 1H), 4.88 (m, 1H), 5.03 (m, 1H), 7.22–7.35 (m, 5H), 10.9 (brs, 1H), 13.8 (brs, 1H)

IR (CHCl$_3$) 1703, 1556, 1410, 1385 cm$^{-1}$

EI-MS: m/z 388 (M$^+$+1)

EXAMPLE 77

(R)-8-Benzyl-4-carboxymethyl-2-cyclopentyl-7,8-dihydro-1H-imidazo[2,1-i]purin-5(4H)-one hydrochloride (Compound 77)

Compound 66 (1.87 g, 4.21 mmol) obtained in Example 66 was dissolved in 1,4-dioxane (30 mL), to the solution was added 2 mol/L aqueous sodium hydroxide (15 mL), and the mixture was stirred with heating at 70° C. for 3 hours. The reaction solution was concentrated under reduced pressure, and then the residue was neutralized by addition of concentrated hydrochloric acid. The deposited crystals were collected by filtration, washed with water and dried to obtain (R)-1,8-dibenzyl-2-cyclopentyl-7,8-dihydro-1H-imidazo[2,1-i]purin-5(4H)-one (Compound 77a, 1.61 g, 90%). Compound 77a (500 mg, 1.08 mmol) was dissolved in N,N-dimethylformamide (5 mL), to the solution were added potassium carbonate (192 mg, 1.41 mmol, 1.2 equivalents) and bromoacetic acid methyl ester (140 μL, 1.41 mmol, 1.2 equivalents), and the mixture was stirred at room temperature for 12 hours. The reaction solution was concentrated under reduced pressure, water was added to the concentrate, the mixture was extracted with chloroform, and the extract was washed with saturated aqueous sodium chloride, dried over anhydrous sodium sulfate and concentrated. The residue was purified by silica gel column chromatography (ethyl acetate:n-hexane=90:10) to obtain (R)-1,8-dibenzyl-2-cyclopentyl-7,8-dihydro-4-methoxycarbonylmethyl-1H-imidazo[2,1-i]purin-5(4H)-one (Compound 77b, 400 mg, 69%). From Compound 77b (850 mg, 1.71 mmol), (R)-8-benzyl-2-cyclopentyl-7,8-dihydro-4-methoxycarbonylmethyl-1H-imidazo[2,1-i]purin-5(4H)-one (Compound 77c, 220 mg, 29%) was obtained in a manner similar to the method by which Compound 40 was obtained from Adduct 40a in Example 40. Compound 77c (200 mg, 0.49 mmol) was dissolved in a mixed solvent of tetrahydrofuran (1 mL) and water (1 mL), to the solution was added lithium hydroxide hydrate (0.04 g, 0.98 mmol), and the mixture was stirred at room temperature for 2.5 hours. The reaction mixture was adjusted to pH 3 with 1 mol/L hydrochloric acid, and the resulting solid was washed with ethanol and collected by filtration to obtain the title compound (180 mg, 93%).

Melting point: 280° C. (decomposition)

$^1$H-NMR (270 MHz, DMSO-d$_6$) δ 1.59–1.96 (m, 8H), 2.85 (m, 1H), 2.97 (m, 1H), 3.05 (m, 1H), 3.54 (m, 1H), 3.88 (t, 1H, J=9.9 Hz), 4.48 (s, 2H), 4.45–4.54 (m, 1H), 7.20–7.31 (m, 5H).

IR (KBr) 1716, 1704, 1687 cm$^{-1}$

FAB-MS: m/z 394 (M$^+$+1).

Elemental Analysis for $C_{21}H_{23}N_5O_3 \cdot 2H_2O$

Calculated (%): C, 58.73; H, 6.34; N, 16.31. Found (%): C, 58.90; H, 6.25; N, 16.33.

EXAMPLE 78

((R)-8-Benzyl-2-cyclopentyl-4,5,7,8-tetrahydro-5-oxo-1H-imidazo[2,1-i]purine-4-yl)-n-propylacetamide (Compound 78)

Compound 77(50 mg, 0.127 mmol) obtained in Example 77 was dissolved in water (1 mL) and 1,4-dioxane (1 mL), to the solution were added n-propylamine (14 μL, 0.176 mmol, 1.4 equivalents) and 1-ethyl-3-(3-dimethylaminopropyl)carbodiimide hydrochloride (24 mg, 0.127 mmol, 1.0 equivalent), and the mixture was stirred at room temperature for 4 days. The reaction solution was extracted with chloroform, and the extract was washed with saturated aqueous sodium chloride, dried over anhydrous magnesium sulfate and concentrated. The residue was purified by silica gel column chromatography (chloroform:methanol=98:2 to 90:10) to obtain the title compound (25 mg, 45%).

$^1$H-NMR (270 MHz, CDCl$_3$) δ 0.90 (t, 3H, J=7.3 Hz), 1.49–1.59 (m, 2H), 1.63–2.02 (m, 8H), 2.78 (d, 2H, J=5.6 Hz), 3.06 (m, 1H), 3.24 (t, 2H, J=7.3 Hz), 3.67 (dd, 1H, J=10.2, 7.0 Hz), 3.84 (m, 1H), 3.94 (t, 1H, J=10.2 Hz), 4.71 (s, 2H), 6.38 (s, 1H), 7.08–7.21 (m, 5H).

IR (KBr) 3301, 2913, 1697, 1685, 1662, 1654 cm$^{-1}$

TOF-MS: m/z 435 (M$^+$+1)

EXAMPLE 79

(R)-8-Benzyl-2-cyclopentyl-7,8-dihydro-4-[3-(2-oxazolidinon-3-yl)propyl]-1H-imidazo[2,1-i]purin-5(4H)-one 0.5 fumarate (Compound 79)

Compound 77a (130 mg, 0.332 mmol) obtained in Example 77 was dissolved in N,N-dimethylformamide (1 mL), to the solution was added potassium carbonate (138 mg, 1.00 mmol, 3.0 equivalents), and the mixture was stirred at room temperature for 1 hour. To the reaction mixture was added a solution of 3-(3-chloropropyl)-2-oxazolidinone (122 mg, 0.750 mmol, 2.3 equivalents), which was prepared by the method described in EP747356A (International Patent Publication in Japanese No. 8-337570), in N,N-dimethylformamide (1 mL) and then the mixture was stirred at room temperature for 12 hours. The solvent was evaporated, and then to the residue was added water and the mixture was extracted with chloroform. The organic layer was washed with saturated brine, dried over anhydrous magnesium sulfate and purified by silica gel column chromatography (chloroform:methanol=100:5) to obtain an adduct (170 mg, 99%). Then, debenzylation was carried out in a manner similar to the method by which Compound 40 was obtained from Adduct 40a in Example 40. To the resulting residue were added fumaric acid and methanol, and the mixture was concentrated. To the residue were added acetone and diethyl ether for crystallization to obtain the title compound (30 mg, 39%) as white crystals.

Melting point: 210–212° C. (acetone/diethyl ether)

$^1$H-NMR (270 MHz, CDCl$_3$) δ 1.70–1.90 (m, 2H), 1.90–2.00 (m, 4H), 2.04 (m, 2H), 2.10–2.25 (m, 2H), 2.97 (dd, 1H, J=13.8, 8.6 Hz), 3.27 (m, 2H), 3.36 (t, 2H, J=6.7 Hz), 3.62 (dd, 2H, J=8.9, 7.1 Hz), 4.03 (dd, 1H, J=11.9, 6.7 Hz), 4.14 (m, 3H), 4.35 (dd, 2H, J=8.9, 7.1 Hz), 4.71 (m, 1H), 7.20–7.35 (m, 5H), 8.52 (s, 2H).

IR (KBr) 1738, 1722, 1672, 1581, 1371 cm$^{-1}$

Elemental Analysis for $C_{25}H_{30}N_6O_3 \cdot 0.5C_4H_4O_4 \cdot 0.5H_2O$

Calculated (%): C, 61.23; H, 6.28; N, 15.87. Found (%): C, 61.38; H, 6.35; N, 15.86.

EXAMPLE 80

(R)-2-Cyclopentyl-8-(4-fluorobenzyl)-7,8-dihydro-4-(2-hydroxyethyl)-1H-imidazo[2,1-i]purin-5(4H)-one hydrochloride (Compound 80)

To Compound C3 obtained in Reference Example 38 was added thionyl chloride, and a cyclized compound was obtained in a manner similar to that in Example 66. From the resulting cyclized compound, a hydrolyzed compound was obtained in a manner similar to the method by which Compound 77a was obtained from the Compound 66 in Example 77. From the resulting hydrolyzed compound (590 mg, 1.33 mmol) and 2-(2-bromoethoxy)tetrahydro-2H-pyran (400 μL, 2.65 mmol, 2.0 equivalents), an adduct (0.56 g, 74%) was obtained in a manner similar to that in Example 79, and the residue was dissolved in methanol (10 mL). To the mixture was added p-toluenesulfonic acid monohydrate and the mixture was stirred with heating at 60° C. for 2 hours. The reaction solution was concentrated and directly purified by silica gel column chromatography (chloroform:methanol=98:2 to 97:3). Then, the title compound in the free form was obtained in a manner similar to the method by which Compound 40 was obtained from Adduct 40a in Example 40. To the resulting free compound were added a 4 mol/L solution of hydrogen chloride in dioxane (2 mL) and methanol (2 mL), the mixture was concentrated, and the residue was crystallized from acetone and diethyl ether to obtain the title compound (210 mg, 49%) as a white solid.

Melting point: 165–167° C. (acetone/diethyl ether)

$^1$H-NMR (270 MHz, CDCl$_3$) δ 1.60–1.72 (m, 2H), 1.74–1.91 (m, 4H), 1.92–2.10 (m, 2H), 2.83 (d, 2H, J=6.2 Hz), 3.07 (quin, 1H, J=7.6 Hz), 3.73 (dd, 2H, J=10.2, 5.6 Hz), 3.91–4.09 (m, 3H), 4.32 (t, 2H, J=4.3 Hz), 6.84–6.90 (m, 2H), 7.07–7.18 (m, 2H).

IR (KBr) 1716, 1701, 1695, 1684, 1589, 1508, 1219 cm$^{-1}$

EI-MS: m/z 398 (M$^+$+1).

Elemental Analysis for $C_{21}H_{24}FN_5O_2 \cdot 1.0HCl \cdot 0.5H_2O$

Calculated (%): C, 56.95; H, 5.92; N, 15.81. Found (%): C, 56.99; H, 6.01; N, 15.49.

EXAMPLE 81

(R)-8-Benzyl-2-cyclopentyl-7,8-dihydro-4-(2-hydroxy-2-methylpropyl)-1H-imidazo[2,1-i]purin-5(4H)-one hydrochloride (Compound 81)

Compound 77c (670 mg, 1.65 mmol) obtained in Example 77 was dissolved in tetrahydrofuran (7 mL), to the solution was added methyl magnesium bromide (2.75 mL, a 3.0 mol/L solution in diethyl ether, 5.0 equivalents) under ice cooling, and the mixture was stirred at the same temperature for 2 hours. To the reaction mixture was added saturated aqueous ammonium chloride, and the mixture was warmed to room temperature and stirred for 10 minutes. The reaction mixture was extracted with chloroform, and the resulting organic layer was washed with saturated aqueous sodium hydrogen carbonate and saturated brine and dried over anhydrous magnesium sulfate. The solvent was evaporated, and the residue was purified by silica gel column chromatography (chloroform:methanol=99:1). The product was converted into hydrochloride with a 4 mol/L solution of hydrogen chloride in dioxane, and then, after the solvent was evaporated, the product was recrystallized from ethyl acetate to obtain the title compound (460 mg, 68%).

$^1$H-NMR (270 MHz, CDCl$_3$) δ 1.23 (s, 3H), 1.25 (s, 3H), 1.67–1.93 (m, 8H), 2.96–3.09 (m, 1H), 3.26 (d, 2H, J=6.2 Hz), 3.93–4.34 (m, 4H), 4.72 (m, 1H), 7.19–7.39 (m, 5H).

IR (KBr) 2968, 1685, 1662, 1654, 1546, 1496 cm$^{-1}$

TOF-MS: m/z 408 (M$^+$+1)

Elemental Analysis for $C_{23}H_{29}N_5O_2 \cdot HCl$

Calculated (%): C, 61.97; H, 6.83; N, 15.71. Found (%): C, 61.95; H, 6.90; N, 15.45.

EXAMPLE 82

(R)-8-Benzyl-2-cyclopentyl-7,8-dihydro-4-(3-hydroxypropyl)-1H-imidazo[2,1-i]purin-5(4H)-one hydrochloride (Compound 82)

An adduct (190 mg, 0.340 mmol) obtained from Compound 77a prepared in Example 0.77 and 2-(3-bromopropoxy)tetrahydro-2H-pyran was dissolved in methanol (5 mL), to the solution were added palladium hydroxide (20 mg, 10% on carbon) and ammonium formate (230 mg, 3.42 mmol), and the mixture was stirred at 50° C. for 3 hours. The reaction mixture was filtered by using a filtration aid, and the resulting filtrate was concentrated. To the residue were added water and chloroform for extraction, and the resulting organic layer was dried over anhydrous magnesium sulfate. The solvent was evaporated, and the resulting residue was purified by preparative silica gel thin layer chromatography (chloroform:methanol=95:5) to obtain a debenzylated compound (0.11 g). The product was dissolved in tetrahydrofuran (1 mL), to the solution was added 1 mol/L hydrochloric acid (1 mL), and the mixture was stirred at room temperature for 4 hours. The reaction mixture was adjusted to pH 7 with saturated aqueous sodium hydrogen carbonate and the mixture was extracted with ethyl acetate. The resulting organic layer was dried over anhydrous magnesium sulfate, and the solvent was evaporated. The resulting oil was purified by preparative silica gel thin layer chromatography (chloroform:methanol=95:5) to obtain the title compound in the free form. The resulting oil was dissolved in dioxane (1 mL) and converted into hydrochloride by addition of a 4 mol/L solution of hydrochloric acid in dioxane. The solvent was evaporated under reduced pressure, and the residue was crystallized from ethyl acetate and hexane to obtain the title compound (40 mg, 27%).

Melting point: 187–188° C. (ethyl acetate/hexane)

$^1$H-NMR (270 MHz, CDCl$_3$) δ 1.64–2.07 (m, 10H), 2.70–2.82 (m, 2H), 3.08 (m, 1H), 3.53 (brt, 2H, J=5.3 Hz), 3.64–3.71 (m, 2H), 3.95 (m, 1H), 4.26 (t, 2H, J=5.6 Hz), 7.07–7.17 (m, 5H).

IR (KBr) 2787, 1718, 1683, 744, 727, 696 cm$^{-1}$

FAB-MS: m/z 384 (M$^+$+1).

Elemental Analysis for C$_{22}$H$_{26}$N$_5$O$_2$.HCl.0.5H$_2$O

Calculated (%): C, 60.34; H, 6.44; N, 15.99. Found (%): C, 60.10; H, 6.68; N, 15.54.

EXAMPLE 83

(R)-8-Benzyl-2-(tert-butyl)-7,8-dihydro-4-(3-hydroxypropyl)-1H-imidazo[2,1-i]purin-5(4H)-one hydrochloride (Compound 83)

A cyclized compound was obtained by using Compound C6 prepared in Reference Example 41 in a manner similar to that in Example 66, from which (R)-1,8-dibenzyl-2-(tert-butyl)-7,8-dihydro-1H-imidazo[2,1-i]purin-5(4H)-one (Compound 83a) was obtained in a manner similar to the method by which Compound 77a was obtained from the Compound 66 in Example 77. Then the title compound was obtained in a manner similar to that in Example 82.

$^1$H-NMR (270 MHz, CDCl$_3$) δ 1.36 (s, 9H), 1.90 (m, 2H), 2.89 (dd, 1H, J=13.8, 6.8 Hz), 2.99 (dd, 1H, J=13.8, 7.3 Hz), 3.47 (t, 2H, J=5.5 Hz), 3.82 (dd, 1H, J=11.3, 6.6 Hz), 4.10 (dd, 1H, J=11.3, 9.7 Hz), 4.22 (t, 2H, J=5.7 Hz), 4.47 (m, 1H), 4.70 (brs, 2H), 7.16–7.34 (m, 5H).

EI-MS: m/z 382 (M$^+$+1).

EXAMPLE 84

1-((R)-8-Benzyl-2-cyclopentyl-4,5,7,8-tetrahydro-5-oxo-1H-imidazo[2,1-i]purin-4-yl)butan-3-one ethylene acetal (Compound 84)

In a manner similar to that in Example 79, the title compound (400 mg, 76%) was obtained from Compounds 77a (500 mg) prepared in Example 77 and 2-(2-bromoethyl)-2-methyl-1,3-dioxolane.

Melting point: 200–201° C. (ethyl acetate)

$^1$H-NMR (270 MHz, CDCl$_3$) δ 1.38 (s, 3H), 1.72–1.88 (m, 6H), 2.10–2.18 (m, 4H), 2.99 (dd, 1H, J=13.8, 7.6 Hz), 3.24 (dd, 1H, J=13.8, 4.5 Hz), 3.28 (m, 1H), 3.89–3.95 (m, 4H), 4.06 (dd, 1H, J=11.9, 6.8 Hz), 4.16–4.25 (m, 3H), 4.71 (m, 1H), 7.23–7.36 (m, 5H), 11.4 (brs, 1H).

IR (KBr) 1718, 1683, 1591 cm$^{-1}$

TOF-MS: m/z 450 (M$^+$+1).

Elemental Analysis for C$_{25}$H$_{31}$N$_5$O$_3$.0.5H$_2$O

Calculated (%): C, 65.48; H, 7.03; N, 15.27. Found (%): C, 65.28; H, 7.06; N, 15.10.

EXAMPLE 85

(R)-8-Benzyl-2-cyclopentyl-7,8-dihydro-4-(3-hydroxy-3-methylbutyl)-1H-imidazo[2,1-i]purin-5(4H)-one hydrochloride (Compound 85)

Compound 84 (1.20 g, 2.67 mmol) obtained in Example 84 was dissolved in acetone (50 mL), to the solution was added p-toluenesulfonic acid hydrate (60 mg, 0.320 mmol, 0.12 equivalent), and the mixture was stirred with heating at 80° C. for 3 hours. The solvent was evaporated under reduced pressure, to the residue were added tetrahydrofuran (32 mL) and 1 mol/L hydrochloric acid (32 mL), and the mixture was stirred at room temperature for 1 hour. The solvent was evaporated, the residue was adjusted to pH 8 with saturated aqueous sodium hydrogen carbonate, and the mixture was extracted with chloroform. The resulting organic layer was washed with saturated aqueous sodium chloride and dried over anhydrous magnesium sulfate. The solvent was evaporated under reduced pressure, and the resulting residue was purified by silica gel column chromatography (chloroform) to obtain a ketone compound (400 mg, 37%). The ketone compound (400 mg, 0.990 mmol) was dissolved in tetrahydrofuran (14 mL), to the solution was added methyl magnesium bromide (2.43 mL, a 1.0 mol/L solution in tetrahydrofuran) under ice cooling, and the mixture was stirred at the same temperature for 2 hours. To the reaction mixture was added saturated aqueous ammonium chloride, and the mixture was warmed to room temperature and stirred for 10 minutes. The reaction mixture was extracted with chloroform, and the resulting organic layer was washed with saturated aqueous sodium hydrogen carbonate and saturated aqueous sodium chloride and dried over anhydrous magnesium sulfate. The solvent was evaporated, and the residue was purified by silica gel column chromatography (chloroform:methanol=95:5) to obtain the title compound in the free form. The free compound was converted into hydrochloride with a 4 mol/L solution of hydrogen chloride in dioxane, and, after the solvent was evaporated, recrystallization was carried out from ethyl acetate to obtain the title compound (230 mg, 51%).

Melting point: 206–207° C. (ethyl acetate)

$^1$H-NMR (270 MHz, CDCl$_3$) δ 1.28 (s, 6H), 1.72–1.93 (m, 8H), 2.04–2.20 (m, 2H), 3.00 (dd, 1H, J=13.8, 7.6 Hz), 3.23 (dd, 1H, J=13.8, 4.7 Hz), 3.28 (m, 1H), 4.07 (dd, 1H, J=12.0, 6.5 Hz), 4.17–4.29 (m, 3H), 4.73 (m, 1H), 7.21–7.36 (m, 5H), 11.5 (brs, 1H).

IR (KBr) 2981, 1718, 1654 cm$^{-1}$

TOF-MS: m/z 422 (M$^+$+1).

Elemental Analysis for $C_{24}H_{31}N_5O_2 \cdot HCl \cdot 0.8H_2O$

Calculated (%): C, 61.02; H, 7.17; N, 14.82. Found (%): C, 61.09; H, 7.27; N, 14.82.

EXAMPLE 86

(R)-8-Benzyl-2-(tert-butyl)-7,8-dihydro-4-(3-hydroxy-3-methylbutyl)-1H-imidazo[2,1-i]purin-5 (4H)-one hydrochloride (Compound 86)

In a manner similar to that in Example 79, a dioxolane compound was obtained from Compound 83a obtained in Example 83 and 2-(2-bromoethyl)-2-methyl-1,3-dioxolane. Then, the title compound (40 mg, 55%) was obtained from the dioxolane compound (90 mg, 0.220 mmol) in a manner similar to that in Example 85.

$^1$H-NMR (270 MHz, CDCl$_3$) δ 1.22 (s, 6H), 1.37 (s, 9H), 1.94 (t, 2H, J=6.4 Hz), 2.86 (dd, 1H, J=13.5, 7.0 Hz), 3.00 (dd, 1H, J=13.5, 6.8 Hz), 3.79 (dd, 1H, J=11.3, 6.8 Hz), 4.03 (dd, 1H, J=11.3, 9.7 Hz), 4.23 (t, 2H, J=6.4 Hz), 4.41–4.52 (m, 3H), 7.17–7.37 (m, 5H).

EI-MS: m/z 410 (M$^+$+1).

EXAMPLE 87

(R)-9-Benzyl-2-ethoxymethyl-6,7,8,9-tetrahydro-4-(n-propyl)-1H-pyrimidino[2,1-i]purin-5(4H)-one (Compound 87)

In a manner similar to that in Example 45, the title compound (22 mg, 18%) was obtained from Compound B12 (95 mg, 0.340 mmol) prepared in Reference Example 22 and Compound A12 (90 mg, 0.561 mmol, 1.6 equivalents) prepared in Reference Example 11.

$^1$H-NMR (270 MHz, CDCl$_3$) δ 0.98 (t, 3H, J=7.4 Hz), 1.24 (t, 3H, J=7.1 Hz), 1.84 (q, 2H, J=7.4 Hz), 1.85 (m, 1H), 2.11 (m, 1H), 2.77 (dd, 1H, J=13.7, 7.9 Hz), 2.97 (dd, 1H, J=13.7, 6.6 Hz), 3.64 (q, 2H, J=7.1 Hz), 3.77–3.95 (m, 2H), 4.14 (t, 2H, J=7.6 Hz), 4.28 (m, 1H), 4.58 (d, 1H, J=11.2 Hz), 4.63 (d, 1H, J=11.2 Hz), 7.17–7.34 (m, 5H).

EI-MS: m/z 382 (M$^+$+1).

EXAMPLE 88

8-Benzyl-2-ethoxymethyl-6,7,8,9-tetrahydro-4-(n-propyl)-1H-pyrimidino[2,1-i]purin-5(4H)-one fumarate (Compound 88)

In a manner similar to that in Example 45, the title compound in the free form was obtained from Compound B12 (200 mg, 0.710 mmol) prepared in Reference Example 22 and Compound A13 (220 mg, 1.33 mmol, 1.9 equivalents) prepared in Reference Example 12. The title compound (25 mg, 4%) was obtained as white crystals from the resulting free compound and fumaric acid.

Melting point: 152–157° C. (ethyl acetate/n-hexane)

$^1$H-NMR (270 MHz, CDCl$_3$) δ 0.98 (t, 3H, J=7.3 Hz), 1.28 (t, 3H, J=6.9 Hz), 1.81 (q, 2H, J=7.3 Hz), 2.40 (m, 1H), 2.70–2.85 (m, 2H), 3.25 (dd, 1H, J=14.2, 9.6 Hz), 3.45 (dd, 1H, J=13.8, 9.9 Hz), 3.66 (dd, 1H, J=14.2, 6.9 Hz), 3.67 (t, 2H, J=6.9 Hz), 4.14 (t, 2H, J=7.4 Hz), 4.44 (brd, 1H, J=11.6 Hz), 4.67 (s, 2H), 6.87 (s, 4H), 7.16–7.37 (m, 5H).

IR (KBr): 1713, 1662, 1605, 1568, 1379, 1362, 1296, 1265, 1111 cm$^{-1}$

EI-MS: m/z 382 (M$^+$+1).

Elemental Analysis for $C_{21}H_{27}N_5O_2 \cdot 1.0C_4H_4O_4$

Calculated (%): C, 60.35; H, 6.28; N, 14.08. Found (%): C, 60.57; H, 6.79; N, 14.12.

EXAMPLE 89

2-Cyclopentyl-6,7,8,9-tetrahydro-4-(n-propyl)-8-(3-pyridyl)-1H-pyrimidino[2,1-i]purin-5(4H)-one (Compound 89)

In a manner similar to that in Example 45, the title compound (42 mg, 12%) was obtained from Compound BI (200 mg, 0.680 mmol) and Compound A14 (210 mg, 1.40 mmol, 2.0 equivalents) prepared in Reference Example 13.

Melting point: 190–195° C. (acetone/diethyl ether)

$^1$H-NMR (270 MHz, CDCl$_3$) δ 0.97 (t, 3H, J=7.3 Hz), 1.61–1.89 (m, 8H), 2.09 (q, 2H, J=7.3 Hz), 3.14–3.30 (m, 2H), 3.51–3.81 (m, 3H), 4.04–4.10 (m, 2H), 4.60 (brd, 1H, J=6.9 Hz), 7.32 (dd, 1H, J=7.9, 4.8 Hz) 7.55 (brd, 1H, J=7.9 Hz), 8.55–8.59 (m, 2H).

IR (KBr): 1686, 1645, 1605, 1564, 1504 cm$^{-1}$

EI-MS: m/z 379 (M$^+$+1).

Elemental Analysis for $C_{21}H_{26}N_6O \cdot 0.3H_2O$

Calculated (%): C, 65.71; H, 6.98; N, 21.89. Found (%): C, 65.59; H, 6.91; N, 21.73.

FORMULATION EXAMPLE 1

Tablet

A tablet having the following formulation is prepared in a conventional manner.

| Composition | |
|---|---|
| Compound 2 | 20 mg |
| Lactose | 143.4 mg |
| Potato starch | 30 mg |
| Hydroxypropylcellulose | 6 mg |
| Magnesium stearate | 0.6 mg |
| | 200 mg |

FORMULATION EXAMPLE 2

Injection

Injection having the following formulation is prepared in a conventional manner.

| Composition | |
|---|---|
| Compound 9 | 2 mg |
| Purified soybean oil | 200 mg |
| Purified yolk lecithin | 24 mg |
| Glycerol for injection | 50 mg |
| Distilled water for injection | 1.72 ml |
| | 2.00 ml |

TEST EXAMPLE 1

Acute Toxicity Test

A test compound was orally administered to dd mice [male, body weight: 20±1 g (n=3)]. Mortality rate after seven days was measured to determine minimum lethal dose (MLD). As a result, MLD of Compound 2 was not less than 500 mg/kg (mice, po), which revealed safety of the compound of the present invention.

TEST EXAMPLE 2

Insulin Secretion Promoting Activity for Cultured β Cells

The established pancreas β-cell, MIN6 cell, reported by Miyazaki et al. (Endocrinology, vol. 127, pp. 126–131, 1990) exhibits insulin content and insulin secretion amount by stimulation with glucose similar to those of pancreas β-cells in living bodies, and well preserves characteristics of pancreas β-cells in living bodies from a viewpoint that it shows increase of insulin secretion in a glucose concentration-dependent manner (the above reference and Diabetologia, vol. 36, pp. 1139–1145, 1993). Further, the insulin secretion of the MIN6 cell is promoted in response to sulfonylurea agents such as glibenclamide, which are used as a medicament for treatment of diabetes (Cellular Signalling, vol. 5, pp. 777–786, 1993).

Culture of the MIN6 cells above and insulin secretion test utilizing the MIN6 cells were performed according to the methods described in Diabetologia, vol. 36, pp. 1139–1145, 1993. The effect of a compound on the insulin secretion in the presence of 14.5 mmol/L glucose was determined by measuring insulin amounts in cell culture supernatants collected as follows. MIN6 cells cultured on a 24-well plate were washed twice by using 1 mL of Buffer A (119 mmol/L sodium chloride, 4.74 mmol/L potassium chloride, 2.54 mmol/L calcium chloride, 1.19 mmol/L magnesium sulfate, 1.19 mmol/L potassium dihydrogenphosphate, 10 mmol/L 2-[4-(2-hydroxyethyl)-1-piperazinyl]ethanesulfonic acid, 0.1% bovine serum albumin, pH 7.3) containing 2 mmol/L glucose, and then were incubated in 1 mL of Buffer A containing 2 mmol/L glucose at 37° C. for 45 minutes. After the incubation, the culture supernatant was changed to Buffer A (0.9 mL) containing a test compound at various concentrations and 2 mmol/L glucose, and the cells were further incubated at 37° C. for 15 minutes. The MIN6 cells were stimulated with glucose by the addition of Buffer A (0.1 mL) containing 127 mmol/L glucose to the culture (final glucose concentration: 14.5 mmol/L). After the stimulation, the cells were further incubated at 37° C. for 45 minutes, and then the culture supernatant was collected.

Separately, the effect of a compound on the insulin secretion in the presence of 5 mmol/L glucose was determined by measuring insulin amounts in cell culture supernatants collected as follows. MIN6 cells cultured on a 24-well plate were washed twice by using 1 mL of Buffer A containing 5 mmol/L glucose, and then the culture supernatant was changed to Buffer A (0.9 mL) containing a test compound at various concentrations and 5 mmol/L glucose. Then, the cells were incubated at 37° C. for 45 minutes (final glucose concentration: 5 mmol/L), and the culture supernatant was collected.

After the culture supernatant was diluted with a phosphate buffer containing 1% bovine serum albumin, 0.1% Tween 20, 0.12% disodium ethylenediaminetetraacetate (EDTA) and 0.1% sodium azide, antibody-reactive insulin secreted in the culture supernatant was quantified by enzyme immunoassay or radio immunoassay. The insulin level was indicated as the amount of human insulin (ng/mL). The results are indicated as averages (avg) for 3 to 4 samples with standard erroe values (se).

The results are shown in Table 2.

TABLE 2

(In the presence of 14.5 mmol/L of glucose)

| Compound No. | Drug concentration (μmol/L) | Insulin secretion amount (ng/ml) avg | se |
|---|---|---|---|
| None | — | 148.4 | 4.8 |
| 2 | 1.0 | 203.6 | 13.9 |
| 9 | 1.0 | 197.6 | 17.9 |
| 10 | 1.0 | 196.8 | 4.6 |
| 14 | 1.0 | 177.9 | 2.6 |
| 21 | 1.0 | 182.1 | 5.3 |
| 24 | 1.0 | 200.0 | 5.1 |
| 40 | 1.0 | 191.2 | 3.1 |
| 45 | 1.0 | 178.8 | 8.4 |
| 51 | 1.0 | 180.8 | 4.5 |
| 56 | 1.0 | 189.0 | 3.5 |
| 64 | 1.0 | 204.9 | 5.9 |
| 70 | 1.0 | 174.9 | 9.6 |
| 71 | 1.0 | 211.0 | 1.7 |
| 73 | 1.0 | 176.6 | 3.9 |
| 81 | 1.0 | 195.4 | 7.4 |
| 85 | 1.0 | 197.1 | 11.1 |
| AY4166 | 10 | 195.1 | 4.3 |
| Glibenclamide | 0.1 | 177.8 | 3.3 |

(In the presence of 5 mmol/L of glucose)

| Compound No. | Drug concentration (mmol/L) | Insulin secretion amount (ng/ml) avg | se |
|---|---|---|---|
| None | — | 51.2 | 11.3 |
| 2 | 10 | 86.3 | 8.2 |
| 9 | 10 | 74.0 | 7.6 |
| 10 | 10 | 74.9 | 3.8 |
| 14 | 10 | 66.4 | 2.6 |
| 21 | 10 | 74.8 | 5.5 |
| 24 | 10 | 71.8 | 8.7 |
| 40 | 10 | 56.7 | 2.4 |
| 45 | 10 | 69.9 | 4.9 |
| 51 | 10 | 79.2 | 2.7 |
| 56 | 10 | 56.2 | 2.1 |
| 64 | 10 | 61.2 | 2.0 |
| 70 | 10 | 57.0 | 2.5 |
| 71 | 10 | 107.7 | 9.1 |
| 73 | 10 | 63.3 | 2.2 |
| 81 | 10 | 83.1 | 2.3 |
| 85 | 10 | 53.6 | 1.1 |
| AY-4166 | 10 | 170.8 | 4.2 |
| Glibenclamide | 0.1 | 156.8 | 8.4 |

As shown in Table 2, it was revealed that the compounds of the present invention had insulin secretion action. Whilst, as shown in Table 2, in the presence of glucose at a low concentration (5 mmol/L), these compounds did not show marked secretion promoting action even at a 10 times higher concentration. Glibenclamide (Pharmacotherapy, vol. 5, p. 43, 1985) and AY-4166 (Yakuri To Rinsho [Pharmacology and Clinic], vol 7, p. 121, 1997) used as controls for comparison showed marked secretion promoting action even at a low glucose concentration.

TEST EXAMPLE 3

Hyperglycemia Suppressing Action After Glucose Loading in Normal Rats

Wistar male rats (body weight: about 280 g) were used for the experiment after starvation for 24 hours. A test compound was orally administered to the rats 15 minutes before oral administration of glucose (2 g/kg). Blood was collected from a tail vein before the administration of the test compound and 30, 60, 120 and 180 minutes after the glucose loading, and blood glucose level was measured by using a simplified blood sugar level measuring apparatus.

The results are shown in Table 3.

TABLE 3

| Compound | Dose (mg/kg, po) | n | Plasma Glucose Concentration (mg/dl) | | | | |
| --- | --- | --- | --- | --- | --- | --- | --- |
| | | | 0 | 30 | 60 | 120 | 180 |
| Control | — | 6 | 82 ± 3.7 | 169 ± 7.2 | 167 ± 8.0 | 93 ± 4.5 | 83 ± 3.7 |
| 2 | 14 | 6 | 91 ± 2.1 | 144 ± 6.6* | 156 ± 5.7 | 90 ± 5.7 | 82 ± 4.2 |

Significance; *$P < 0.05$ (Student's t-test or Aspin-Welch test)

As clearly shown in Table 3, the compound of the present invention was found to have hyperglycemia suppressing action 30 minutes after the glucose loading. However, the compound exhibited no hypoglycemic action during the fasted state.

Industrial Applicability

According to the present invention, condensed purine derivatives, which have glucose concentration-dependent insulin secretion promoting action and hypoglycemic action and are useful as an antidiabetic agent or the like, are provided.

What is claimed is:

1. A condensed purine derivative represented by Formula (I):

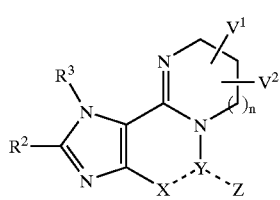

wherein X—Y—Z represents $R^1$N—C=O (in the formula, $R^1$ represents a hydrogen atom, a substituted or unsubstituted lower alkyl group, a substituted or unsubstituted mono-cycloalkyl group, a substituted or unsubstituted (mono-cycloalkyl)-substituted lower alkyl group, a substituted or unsubstituted aryl group, or a substituted or unsubstituted aromatic heterocyclic group) or N=C—W, $R^2$ represents a substituted or unsubstituted lower alkyl group, a substituted or unsubstituted mono-cycloalkyl group, a substituted or unsubstituted (mono-cycloalkyl)-substituted lower alkyl group, a substituted or unsubstituted aralkyl group, a substituted or unsubstituted aryl group, a substituted or unsubstituted aromatic heterocyclic group, a substituted or unsubstituted alicyclic heterocyclic group, a halogen atom, a lower alkylthio group, —$NR^7R^8$ (in the formula, $R^7$ and $R^8$ have the same meanings as $R^4$ and $R^5$ mentioned above, respectively), —$CO_2H$, a lower alkoxycarbonyl group, —COHal (in the formula, Hal represents a halogen atom), —$CONR^9R^{10}$ (in the formula, $R^9$ and $R^{10}$ have the same meanings as $R^4$ and $R^5$ mentioned above, respectively) or —CHO, $R^3$ represents a hydrogen atom, a lower alkyl group, mono-cycloalkyl group, a (mono-cycloalkyl)-substituted lower alkyl group, a substituted or unsubstituted aralkyl group, or a lower alkoxyalkyl group, n represents an integer of from 0 to 3, $V^1$ represents a hydrogen atom, a substituted or unsubstituted lower alkyl group, a substituted or unsubstituted mono-cycloalkyl group, a substituted or unsubstituted (mono-cycloalkyl)-substituted lower alkyl group, a substituted or unsubstituted aralkyl group, a substituted or unsubstituted aryl group, or a substituted or unsubstituted aromatic heterocyclic group, $V^2$ represents a substituted lower alkyl group, a substituted mono-cycloalkyl group, a substituted (mono-cycloalkyl)-substituted lower alkyl group, or a substituted or unsubstituted aromatic heterocyclic group, and when $V^1$ represents a hydrogen atom, a lower alkyl group, a mono-cycloalkyl group, a (mono-cycloalkyl)-substituted lower alkyl group, a substituted or unsubstituted aralkyl group, or a substituted or unsubstituted aryl group, and (a) X—Y-Z represents $R^{1a}$N—C=O (in the formula, $R^{1a}$ represents any of the groups in the definition of the aforementioned $R^1$ excluding a substituted lower alkyl group, a substituted mono-cycloalkyl group and a substituted (mono-cycloalkyl)-substituted lower alkyl group), and $R^2$ represents a substituted lower alkyl group, a substituted mono-cycloalkyl group, a substituted or unsubstituted aralkyl group, an unsubstituted alicyclic heterocyclic group, a halogen atom, a lower alkylthio group, —$NR^7R^8$ (in the formula, $R^7$ and $R^8$ have the same meanings as defined above, respectively), —$CO_2H$, a lower alkoxycarbonyl group, —COHal (in the formula, Hal has the same meaning as defined above), —$CONR^9R^{10}$ (in the formula, $R^9$ and $R^{10}$ have the same meanings as those defined above, respectively) or —CHO, (b) X—Y-Z represents $R^1$N—C=O (in the formula, $R^1$ has the same meaning as defined above), and $R^3$ represents a lower alkoxyalkyl group, (c) X—Y-Z represents $R^{1b}$N—C=O (in the formula, $R^{1b}$ represents a substituted lower alkyl group, a substituted mono-cycloalkyl group or a substituted (mono-cycloalkyl)-substituted lower alkyl group), (d) X—Y-Z represents N=C—W (in the formula, W has the same meaning as defined above), and $R^2$ represents a substituted or unsubstituted lower alkyl group, a substituted or unsubstituted mono-cycloalkyl group, a substituted or unsubstituted (mono-cycloalkyl)-substituted lower alkyl group, a substituted or unsubstituted aralkyl group, a substituted or unsubstituted aryl group, a substituted or unsubstituted aromatic heterocyclic group, a substituted or unsubstituted alicyclic heterocyclic group, a halogen atom, a lower alkylthio group, —NR$^7$R$^8$ (in the formula, R$^7$ and R$^8$ have the same meanings as defined above, respectively), —CO$_2$H, a lower alkoxycarbonyl group, —COHal (in the formula, Hal has the same meaning as defined above), —CONR$^9$R$^{10}$ (in the formula, R$^9$ and R$^{10}$ have the same meanings as defined above, respectively) or —CHO, or (e) X—Y-Z represents N=C—W (in the formula, W has the same meaning as defined above), and R$^3$ represents a lower alkyl group, a monocycloalkyl group, a (mono-cycloalkyl)-substituted lower alkyl group, a substituted or unsubstituted aralkyl group, or a lower alkoxyalkyl group, V$^2$ may represent a lower alkyl group, a mono-cycloalkyl group, a (mono-cycloalkyl)-substituted lower alkyl group, a substituted or unsubstituted aralkyl group, or a substituted or unsubstituted aryl group; or a pharmacologically acceptable salt thereof;

wherein the substituent(s) of the substituted aryl group, the substituted aralkyl group, the substituted aromatic heterocyclic group, and the substituted alicyclic heterocyclic group may be the same or different in number of 1 to 3, and are selected from a group consisting of a substituted or unsubstituted lower alkyl group, a substituted or unsubstituted mono-cycloalkyl group, a substituted or unsubstituted aryl group, a substituted or unsubstituted aryloxy group, a substituted or unsubstituted aroyl group, a substituted or unsubstituted aralkyl group, a substituted or unsubstituted aralkyloxy group, a substituted or unsubstituted lower alkenyl group, a substituted or unsubstituted lower alkynyl group, a substituted or unsubstituted lower alkoxy group, a substituted or unsubstituted lower alkoxycarbonyl group, a substituted or unsubstituted lower alkylthio group, a substituted or unsubstituted lower alkylsulfonyl group, a substituted or unsubstituted lower alkanoyl group, a mono- or di-lower alkyl-substituted carbamoyl group, a mono- or di-lower alkyl-substituted amino group, a halogen atom, a carboxyl group, a hydroxyl group, a nitro group, an amino group and a cyano group; wherein the substituent(s) of the substituted lower alkyl group, the substituted mono-cycloalkyl group, the substituted aryl group, the substituted aryloxy group, the substituted aroyl group, the substituted aralkyl group, the substituted aralkyloxy group, the substituted lower alkenyl group, the substituted lower alkynyl group, the substituted lower alkoxy group, the substituted lower alkoxycarbonyl group, the substituted lower alkylthio group, the substituted lower alkylsulfonyl group and the substituted lower alkanoyl group may be the same or different in number of 1 to 3, and are selected from a group consisting of a hydroxyl group, a halogen atom, a carboxyl group, a sulfo group, a phosphono group, and an ester derived from the group selected from a carboxyl group, a sulfo group and a phosphono group; and the substituent(s) of the substituted lower alkyl, the substituted mono-cycloalkyl and the substituted (mono-cycloalkyl)-substituted lower alkyl group may be the same or different in number of 1 to 3, and are selected from a group consisting of a lower alkoxy group, a hydroxyl group, a cyano group, an azido group, a carboxyl group, a phosphono group, an ester derived from the group selected from a carboxyl group, a sulfo group and a phosphono group, a lower alkylthio group, a lower alkylaminocarbonyl group, a lower alkoxycarbonyl group, a substituted or unsubstituted aromatic heterocyclic group, a substituted or unsubstituted alicyclic heterocyclic group, —NR$^{11}$R$^{12}$ (in the formula, R$^{11}$ and R$^{12}$ may be the same or different and each represents a hydrogen atom, a lower alkyl group, a monocycloalkyl group, a lower alkanoyl group, an aryl group, an aralkyl group or an aralkyloxy group, or R$^{11}$ and R$^{12}$ may bind to each other to form a heterocyclic group together with the adjacent nitrogen atom, which is a 5- or 6-membered monocyclic heterocyclic group containing at least one nitrogen atom (said monocyclic heterocyclic group may contain a nitrogen atom other than the above, an oxygen atom, or a sulfur atom), or a bicyclic or tricyclic condensed heterocyclic group comprising 3- to 8-membered rings and containing at least one nitrogen atom (said condensed heterocyclic group may contain a nitrogen atom other than the above, an oxygen atom, or a sulfur atom)), a halogen atom, an arylsulfonyloxy group, a lower alkylsulfonyl group, a lower alkylsulfonyloxy group and a trifluoromethanesulfonyloxy group; wherein the substituent(s) of the substituted aromatic heterocyclic group and the substituted alicyclic heterocyclic group have the same meanings as those mentioned above.

2. The condensed purine derivative or a pharmacologically acceptable salt thereof according to claim 1, wherein X—Y-Z represents R$^1$N—C=O (in the formula, R$^1$ has the same meaning as defined above).

3. The condensed purine derivative or a pharmacologically acceptable salt thereof according to claim 2, wherein R$^1$ and R$^2$ each represent a substituted or unsubstituted lower alkyl group, a substituted or unsubstituted mono-cycloalkyl group, or a substituted or unsubstituted (mono-cycloalkyl)-substituted lower alkyl group and R$^3$ represents a hydrogen atom.

4. The condensed purine derivative or a pharmacologically acceptable salt thereof according to claim 2, wherein at least one of V$^1$ and V$^2$ represents a substituted or unsubstituted aromatic heterocyclic group-substituted lower alkyl group, a substituted or unsubstituted alicyclic heterocyclic group-substituted lower alkyl group, or a —NR$^{11}$R$^{12}$ (in the formula, R$^{11}$ and R$^{12}$ have the same meanings as defined above, respectively)-substituted lower alkyl group.

5. The condensed purine derivative or a pharmacologically acceptable salt thereof according to claim 3, wherein at least one of V$^1$ and V$^2$ represents a substituted or unsubstituted aralkyl group.

6. The condensed purine derivative or a pharmacologically acceptable salt thereof according to claim 1, wherein X—Y-Z represents N=C—W (in the formula, W has the same meaning as defined above).

7. The condensed purine derivative or a pharmacologically acceptable salt thereof according to claim 6, wherein R$^2$ represents a substituted or unsubstituted lower alkyl group, a substituted or unsubstituted mono-cycloalkyl group, or a substituted or unsubstituted (mono-cycloalkyl)-substituted lower alkyl group.

8. The condensed purine derivative or a pharmacologically acceptable salt thereof according to claim 6, wherein at least one of $V^1$ and $V^2$ represents a substituted or unsubstituted aralkyl group.

9. The condensed purine derivative or a pharmacologically acceptable salt thereof according to claim 1, wherein n is 0.

10. A pharmaceutical composition which comprises the condensed purine derivative or a pharmacologically acceptable salt thereof according to claim 1 as an active ingredient and a pharmacologically acceptable carrier.

11. A method for therapeutic treatment of non-insulin dependent diabetes (NIDDM), which comprises administering a therapeutically effective amount of the condensed purine derivative or a pharmacologically acceptable salt thereof according to claim 1.

12. A method for decreasing blood sugar level, which comprises administering a blood sugar level decreasing effective amount of the condensed purine derivative or a pharmacologically acceptable salt thereof according to claim 1.

13. A method for promoting insulin secretion, which comprises administering an insulin secreting promoting effective amount of the condensed purine derivative or a pharmacologically acceptable salt thereof according to claim 1.

14. A method for prophylactic treatment of non-insulin dependent diabetes (NIDDM), which comprises administering a prophylactically effective amount of the condensed purine derivative or a pharmacologically acceptable salt thereof according to claim 1.

* * * * *

UNITED STATES PATENT AND TRADEMARK OFFICE
CERTIFICATE OF CORRECTION

PATENT NO.       : 7,005,430 B2
APPLICATION NO.  : 10/149423
DATED            : February 28, 2006
INVENTOR(S)      : K. Ueno et al.

It is certified that error appears in the above-identified patent and that said Letters Patent is hereby corrected as shown below:

On the cover of the printed patent, at Item (57), Abstract, " 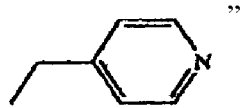 "
should be -- 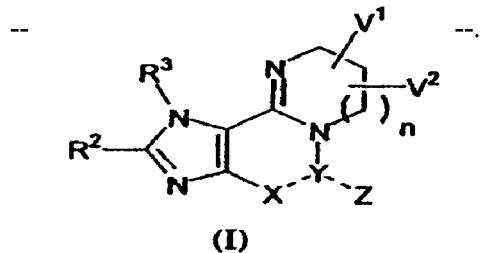 --.

In the Abstract, Specification, and Claims:

At item (57), Abstract, "X—Y-Z" should be --X-Y-Z--;
At column 3, line 13, "X—Y-Z" should be --X-Y-Z--;
At column 3, line 55, "X—Y-Z" should be --X-Y-Z--;
At column 3, line 67, "X—Y-Z" should be --X-Y-Z--;
At column 4, line 3, "X—Y-Z" should be --X-Y-Z--;
At column 4, line 4, "X—Y-Z" should be --X-Y-Z--;
At column 4, line 17, "X—Y-Z" should be --X-Y-Z--;
At column 4, line 26, "X—Y-Z" should be --X-Y-Z--;
At column 4, line 43, "X—Y-Z" should be --X-Y-Z--;
At column 9, line 17, "X—Y-Z" should be --X-Y-Z--;
At column 10, line 11, "X—Y-Z" should be --X-Y-Z--;
At column 10, line 25, "X—Y-Z" should be --X-Y-Z--;
At column 10, line 27, "X—Y-Z" should be --X-Y-Z--;
At column 10, line 31, "X—Y-Z" should be --X-Y-Z--;
At column 10, line 46, "X—Y-Z" should be --X-Y-Z--;
At column 12, line 51, "X—Y-Z" should be --X-Y-Z--;
At column 15, line 7, "X—Y-Z" should be --X-Y-Z--;
At column 16, line 46, "X—Y-Z" should be --X-Y-Z--;

UNITED STATES PATENT AND TRADEMARK OFFICE
CERTIFICATE OF CORRECTION

PATENT NO. : 7,005,430 B2 Page 2 of 5
APPLICATION NO. : 10/149423
DATED : February 28, 2006
INVENTOR(S) : K. Ueno et al.

It is certified that error appears in the above-identified patent and that said Letters Patent is hereby corrected as shown below:

At column 21, line 55, "$X^1$—$Y^1$-$Z^1$" should be --$X^1$-$Y^1$-$Z^1$--;
At column 21, line 67, "X—Y-Z" should be --X-Y-Z--;
At column 22, line 41, "$X^1$—$Y^1$-$Z^1$" should be --$X^1$-$Y^1$-$Z^1$--;
At column 23, line 14, "$X^1$—$Y^1$-$Z^1$" should be --$X^1$-$Y^1$-$Z^1$--;
At column 23, line 50, "$X^1$—$Y^1$-$Z^1$" should be --$X^1$-$Y^1$-$Z^1$--;
At column 24, line 30, "X—Y-Z" should be --X-Y-Z--;
At column 25, line 30, "X—Y-Z" should be --X-Y-Z--;
At column 103, claim 1, line 53, "X—Y-Z" should be --X-Y-Z--;
At column 104, claim 1, line 42, "X—Y-Z" should be --X-Y-Z--;
At column 104, claim 1, line 57, "X—Y-Z" should be --X-Y-Z--;
At column 104, claim 1, line 60, "X—Y-Z" should be --X-Y-Z--;
At column 104, claim 1, line 64, "X—Y-Z" should be --X-Y-Z--;
At column 105, claim 1, line 13, "X—Y-Z" should be --X-Y-Z--;
At column 106, claim 2, line 36, "X—Y-Z" should be --X-Y-Z--;
At column 106, claim 6, line 60, "X—Y-Z" should be --X-Y-Z--.

At column 1, line 50 of the printed patent, " 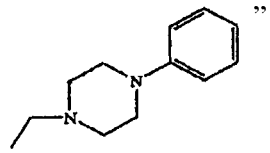 "

should be -- 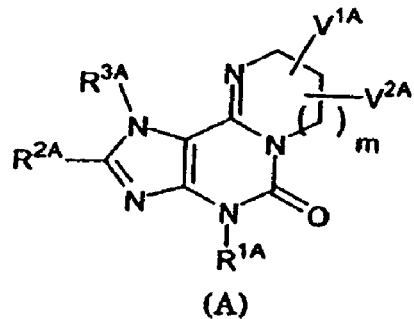 --.

UNITED STATES PATENT AND TRADEMARK OFFICE
CERTIFICATE OF CORRECTION

PATENT NO. : 7,005,430 B2
APPLICATION NO. : 10/149423
DATED : February 28, 2006
INVENTOR(S) : K. Ueno et al.

It is certified that error appears in the above-identified patent and that said Letters Patent is hereby corrected as shown below:

At column 2, line 10 of the printed patent, " 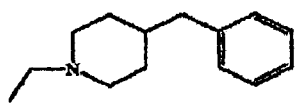 "

should be -- 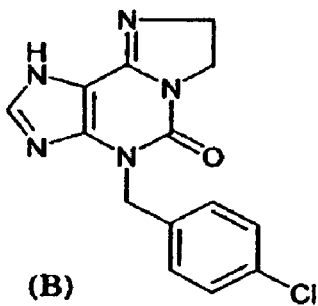 --.

At column 2, line 25 of the printed patent, " 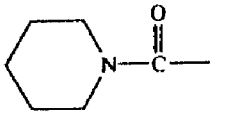 " should be

-- 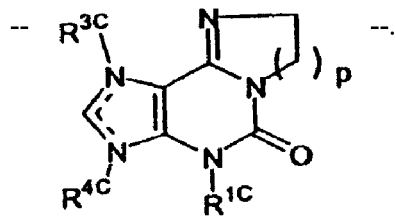 --.

UNITED STATES PATENT AND TRADEMARK OFFICE
CERTIFICATE OF CORRECTION

PATENT NO. : 7,005,430 B2
APPLICATION NO. : 10/149423
DATED : February 28, 2006
INVENTOR(S) : K. Ueno et al.

It is certified that error appears in the above-identified patent and that said Letters Patent is hereby corrected as shown below:

At column 2, line 40 of the printed patent, " 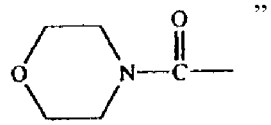 "

should be -- 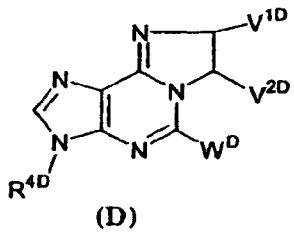 --.

At column 3, line 5 of the printed patent, " 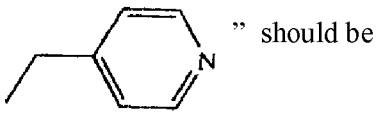 " should be

-- 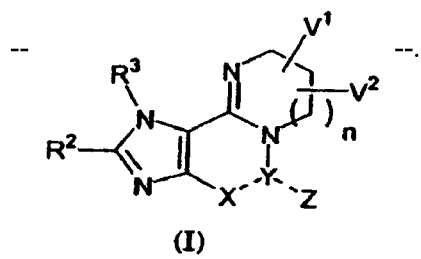 --.

UNITED STATES PATENT AND TRADEMARK OFFICE
CERTIFICATE OF CORRECTION

PATENT NO.         : 7,005,430 B2
APPLICATION NO. : 10/149423
DATED              : February 28, 2006
INVENTOR(S)        : K. Ueno et al.

It is certified that error appears in the above-identified patent and that said Letters Patent is hereby corrected as shown below:

At column 103, line 60 (claim 1, line 20), after "N=C-W" insert --[in the formula, W represents a halogen atom, a substituted or unsubstituted aromatic heterocyclic group, a substituted or unsubstituted alicyclic heterocyclic group, $-NR^4R^5$ (in the formula, $R^4$ and $R^5$ may be the same or different and each represents a hydrogen atom, a substituted or unsubstituted lower alkyl group, a substituted or unsubstituted mono-cycloalkyl group, a substituted or unsubstituted (mono-cycloalkyl)-substituted lower alkyl group, a substituted or unsubstituted aryl group, or a substituted or unsubstituted aralkyl group, or $R^4$ and $R^5$ may bind to each other to form a heterocyclic group together with the adjacent nitrogen atom), $-OR^6$ (in the formula, $R^6$ represents a substituted or unsubstituted lower alkyl group, a substituted or unsubstituted mono-cycloakyl group, a substituted or unsubstituted (mono-cycloalkyl)-substituted lower alkyl group, a substituted or unsubstituted aryl group, or a substituted or unsubstituted aralkyl group), $-SR^{6a}$ (in the formula, $R^{6a}$ has the same meaning as $R^6$ mentioned above), a substituted or unsubstitute lower alkyl group, a substituted or unsubsituted mono-cycloalkyl group, a substituted or unsubstituted (mono-cycloalkyl)-substituted lower alkyl group, or a cyano group]--.

Signed and Sealed this

Twenty-fourth Day of June, 2008

JON W. DUDAS
*Director of the United States Patent and Trademark Office*